US012161299B2

(12) United States Patent
Minami et al.

(10) Patent No.: US 12,161,299 B2
(45) Date of Patent: Dec. 10, 2024

(54) COVER MEMBER AND TREATMENT INSTRUMENT

(71) Applicant: OLYMPUS CORPORATION, Hachioji (JP)

(72) Inventors: Hiroshi Minami, Tokyo (JP); Masami Oshida, Kanagawa (JP); Masato Inoue, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 164 days.

(21) Appl. No.: 17/943,577

(22) Filed: Sep. 13, 2022

(65) Prior Publication Data

US 2023/0000324 A1 Jan. 5, 2023

Related U.S. Application Data

(63) Continuation of application No. PCT/JP2020/019692, filed on May 18, 2020.

(51) Int. Cl.
*A61B 1/018* (2006.01)
*A61B 17/32* (2006.01)

(52) U.S. Cl.
CPC ...... *A61B 1/018* (2013.01); *A61B 17/320068* (2013.01)

(58) Field of Classification Search
CPC ............ A61B 1/018; A61B 17/320068; A61B 2017/00477; A61B 2090/08021
See application file for complete search history.

(56) References Cited

U.S. PATENT DOCUMENTS

| 5,906,628 A | * | 5/1999 | Miyawaki ...... A61B 17/320092 606/171 |
| 2014/0235946 A1 | * | 8/2014 | Smith .................. A61B 90/361 156/303.1 |
| 2015/0148829 A1 | | 5/2015 | Kimball et al. |
| 2020/0107703 A1 | * | 4/2020 | Quinn ................ A61B 1/00142 |

FOREIGN PATENT DOCUMENTS

| AU | 2005258423 | * | 1/2006 |
| JP | H10-5237 A | | 1/1998 |
| JP | H11-89851 | * | 4/1999 |
| JP | H11-89851 A | | 4/1999 |
| JP | 4398493 B2 | | 1/2010 |
| JP | 2017-508482 A | | 3/2017 |

OTHER PUBLICATIONS

Jul. 14, 2020 International Search Report issued in International Patent Application No. PCT/JP2020/019692.

* cited by examiner

*Primary Examiner* — Alexei Bykhovski
(74) *Attorney, Agent, or Firm* — Oliff PLC

(57) ABSTRACT

A cover member includes: a sheath that is formed in a cylindrical shape for receiving a shaft; and a tubular portion that is attached to a distal end of the sheath. The tubular portion being formed such that an outer dimension of a distal end portion of the tubular portion in a first direction is smaller than an outer dimension of a proximal end portion of the tubular portion in the first direction and/or an outer dimension of the distal end portion in a second direction is smaller than an outer dimension of the proximal end portion in the second direction.

12 Claims, 41 Drawing Sheets

COVER MEMBER AND TREATMENT INSTRUMENT

CROSS-REFERENCE TO RELATED APPLICATION

This application is a continuation of International Application No. PCT/JP2020/019692, filed on May 18, 2020, the entire contents of which are incorporated herein by reference.

BACKGROUND

1. Technical Field

The present disclosure relates to a cover member and a treatment instrument.

2. Related Art

In the related art, a treatment instrument that applies an energy to a site subject to treatment in a living tissue (hereinafter, target site), and thereby treats the target site has been known.

For example, the known treatment instrument can be an ultrasound treatment instrument, and can have a vibration transmission member that transmits ultrasonic vibration from a proximal end to a distal end. This vibration transmission member is inserted in a cylindrical sheath with its distal end exposed to the outside. To a distal end of the sheath, a cap to prevent a contact with the vibration transmission member is attached.

SUMMARY

In some embodiments, provided is a cover member that extends in a longitudinal axis direction from a distal end toward a proximal end of the cover member and can receive a shaft provided with an end effector for treating a living tissue at a distal end of the shaft. The cover member includes: sheath that is formed in a cylindrical shape for receiving the shaft; and a tubular portion that is attached to a distal end of the sheath. The tubular portion is formed such that an outer dimension of a distal end portion of the tubular portion in a first direction perpendicular to the longitudinal axis direction is smaller than an outer dimension of a proximal end portion of the tubular portion in the first direction and/or an outer dimension of the distal end portion in the second direction perpendicular to the first direction and the longitudinal axis direction, is smaller than an outer dimension of the proximal end portion in the second direction.

In some embodiments, a treatment instrument includes: a shaft including an end effector for treating a living tissue at a distal end of the shaft; and a cover member including a tubular portion that extends along a longitudinal axis direction from a distal end portion toward a proximal end portion of the tubular portion. The shaft can be inserted into an inside of the tubular portion in a state in which the end effector protrudes out from a distal end of the tubular portion. The tubular portion is formed such that an outer dimension of the distal end portion in a first direction perpendicular to the longitudinal axis direction is smaller than an outer dimension of the proximal end portion in the first direction and/or an outer dimension of the distal end portion in a second direction, perpendicular to the first direction and the longitudinal axis direction, is smaller than an outer dimension of the proximal end portion in the second direction.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 13 is a diagram illustrating a distal end portion of the treatment-instrument main unit according to the exemplary embodiment;

DETAILED DESCRIPTION

Hereinafter, forms to implement the disclosure (hereinafter, embodiments) will be explained with reference to the drawings. Embodiments explained below are not intended to limit the disclosure. Furthermore, in description of the drawings, like reference symbols are assigned to like parts.

Schematic Configuration of Treatment System

Figure 1:
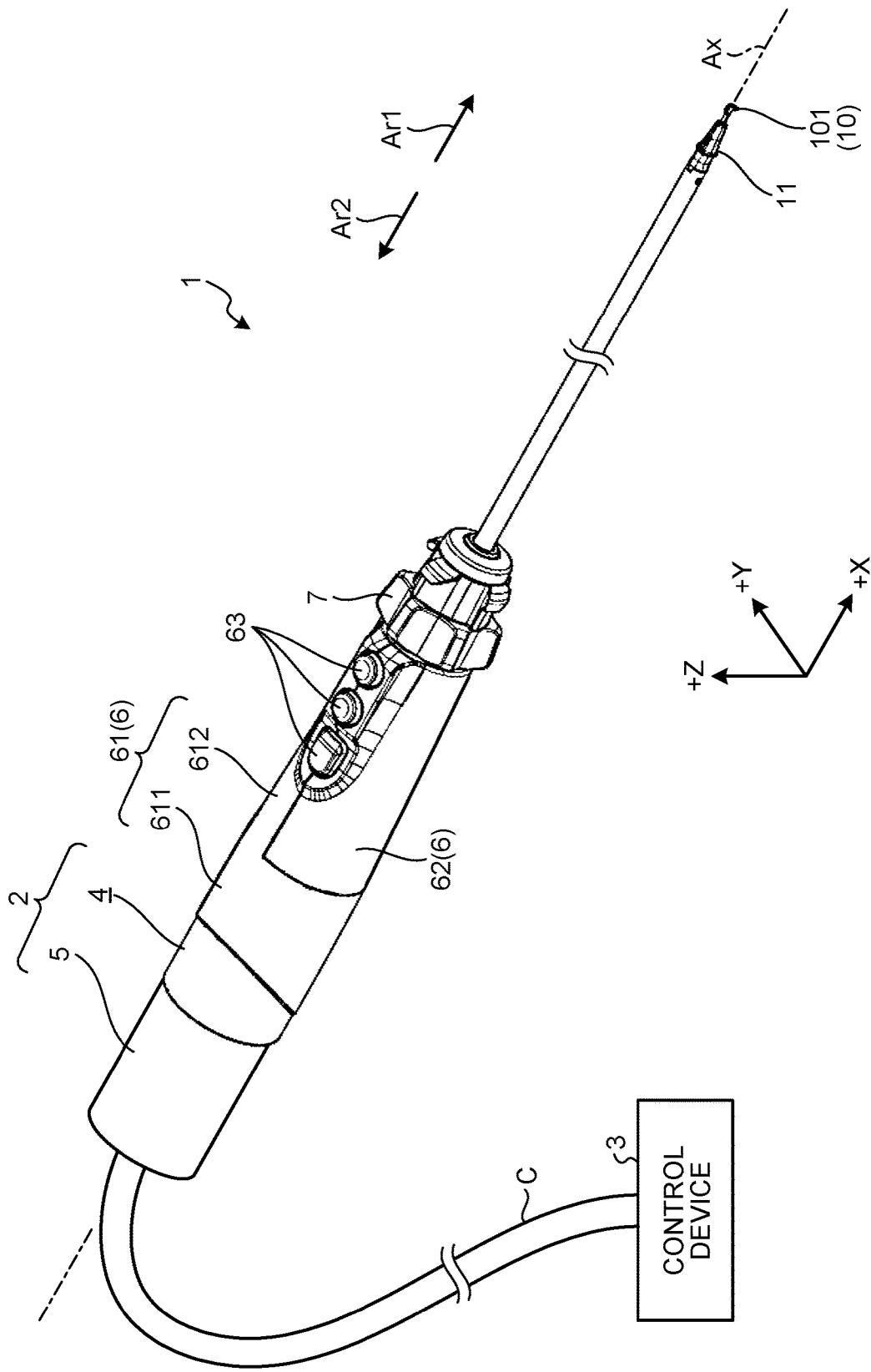
FIG. 1 is a diagram illustrating a treatment system according to an exemplary embodiment.

FIG. 1 is a diagram illustrating a treatment system 1 according to an exemplary embodiment.

The treatment system 1 applies a treatment energy to a site to be treated in a living tissue (hereinafter, treatment site), and thereby, treats the treatment site. In the present embodiment, as the treatment energy, an ultrasonic energy and a high frequency energy are used. Moreover, examples of the treatment include coagulation and incision of a target site. This treatment system 1 includes, as illustrated in FIG. 1, a treatment instrument and a control device Configuration of Treatment Instrument The treatment instrument 2 is an ultrasound treatment instrument that applies least an ultrasonic energy to a target site, and that thereby treats the treatment site. This treatment instrument 2 includes a treatment-instrument main unit 4 and an ultrasound transducer 5.

The treatment-instrument main unit 4 is a component applies a treatment energy to a target site. This treatment-instrument main unit 4 includes, as illustrated in FIG. 1, a housing 6, a rotating knob 7, a sheath 8 (refer to FIG. 2), a holding portion 9 (refer to FIG. 2 FIG. 3), a vibration transmission member 10, and a cap 11.

Figure 2:
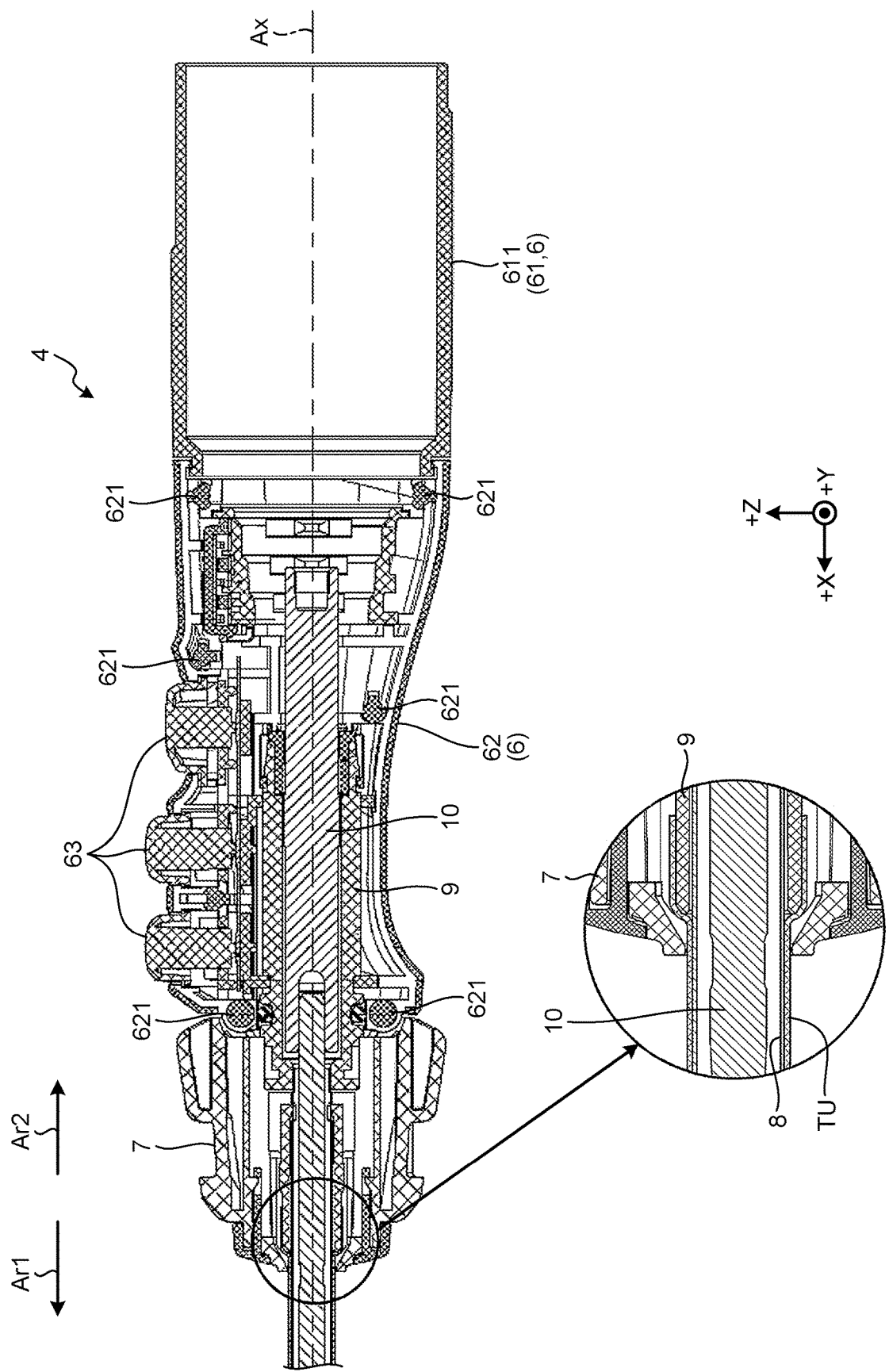
FIG. 2 is a diagram illustrating an inner part of a housing.
Figure 3:
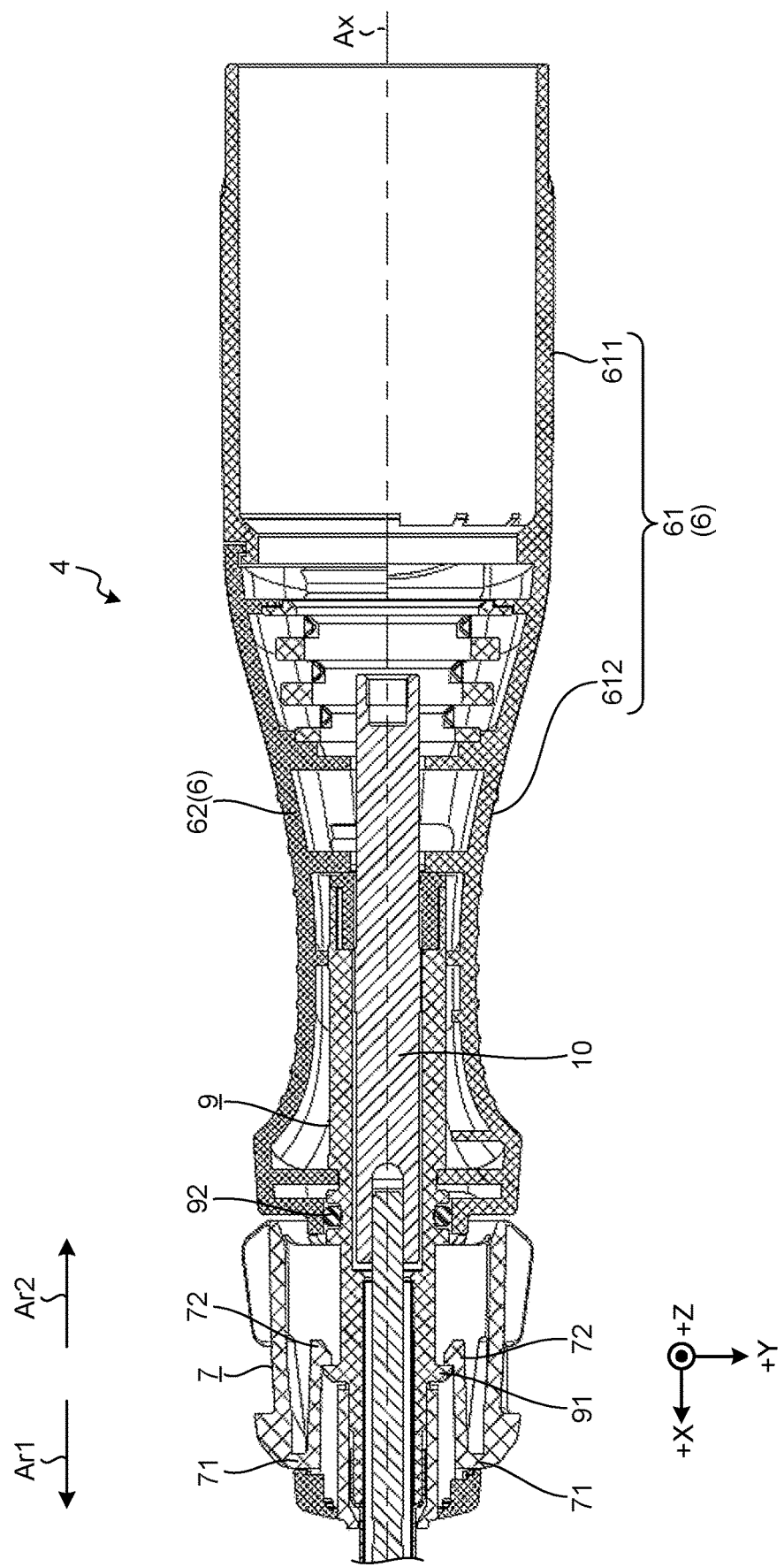
FIG. 3 is a diagram illustrating the inner part of the housing.

FIG. 2 and FIG. 3 are diagrams illustrating an inner part of the housing.

In FIG. 2 and FIG. 3 explained below, XYZ coordinate axes in FIG. 1 are used. The X axis is an axis parallel to a center axis Ax of the sheath 8. The center axis Ax corresponds to a longitudinal axis. Moreover, in the following, one side along the center axis Ax is denoted as a distal end side Ar1, and the other side is denoted as a proximal end side Ar2.

FIG. 2 is a cross-section of the treatment-instrument main unit 4 cut along an XZ plane including the center axis Ax. Moreover, FIG. 3 is a cross-section of the treatment instrument main unit 4 cut along an XY plane including the center axis Ax.

The housing 6 has a substantially cylindrical shape coaxial with the center axis Ax. The housing 6 supports the entire treatment-instrument main unit 4 In the present embodiment, the housing 6 is constituted of a first and a second housings 61, 62 as illustrated in FIG. 1 to FIG. 3.

The first housing 61 includes, as illustrated in FIG. 1 to FIG. 3, a proximal-end-side housing portion 611, a distal-end-side housing portion 612 (FIG. 1, FIG. 3).

The proximal end side housing portion 611 is positioned on the proximal end side Ar2 relative to the distal-end-side housing portion 612, and has a cylindrical shape coaxial with the center axis Ax. In the proximal-end-side housing portion 611, the ultrasound transducer 5 is inserted.

The distal-end-side housing portion 612 is a portion that is formed integrally with an end portion of the proximal-end-side housing portion 611 on the distal end side Ar1, and has a substantially semicircular shape on a cross-section cut along a plane perpendicular to the center axis Ax.

The second housing 62 has a substantially semicircular shape on a cross-section cut along a plane perpendicular to the center axis Ax. At an edge of this second housing 62 plural bosses 621 that respectively protrude along the Y axis are arranged as illustrated in FIG. 2. The second housing 62 is attached tr the distal-end-side housing portion 612 by press-fitting the bosses 621 into plural concave portions (not illustrated) arranged at the edge the distal-end-side housing portion 612. That proximal-end-side housing portion 611 in which the ultrasound transducer 5 is inserted thereinside, bosses or e like are not arranged.

Moreover, in the housing 6, a switch 63 that is arranged exposed to the outside, and that accepts a treatment start operation or the like performed by an operator is provided as illustrated in FIG. 1 or FIG. 2. The switch 63 outputs an operation signal according to the treatment start operation to the control device 3 through an electric cable C (FIG. 1) that electrically connects the treatment instrument 2 and the control device 3.

The rotating knob 7 has a substantially cylindrical shape coaxial with the center axis Ax and is arranged in the housing 6 on the distal end side Ar1 as illustrated in FIG. 1 to FIG. 3. This rotating knob 7 accepts a rotation operation performed by the operator. The rotation operation is an operation to rotate the vibration transmission member 10 about the center axis Ax. The rotating knob 7 and the vibration transmission member 10 rotate about the center axis Ax by the rotation operation.

The sheath 8 is a cylindrical pipe made from a material, such as metal. To the sheath 8, the vibration transmission member 10 is inserted.

A structure of an end portion of the sheath 8 on the end side Ar1 will be described later in "About Distal End Portion of Treatment-Instrument Main Unit".

The holding portion 9 is made from, for example, resin material having electrical insulation, and has a substantially cylindrical shape coaxial with the center axis Ax. This holding portion 9 is housed rotatably about the center axis Ax in the housing 6 in such a manner that an end portion on the distal end side Ar1 protrudes out from the housing 6 as illustrated in FIG. 2 or FIG. 3. The holding portion 9 holds the vibration transmission member 10 in a state in which the vibration transmission member 10 is inserted thereinside. Furthermore, the holding portion 9 holds the sheath 8 in such a manner that an end portion of the sheath 8 on the proximal end side Ar2 is inserted therein from the distal end side Ar1.

On an outer peripheral surface of the holding portion 9, as illustrated in FIG. 3, a flange portion 91 jutting out toward the outside is arranged on the distal end side Ar1. Moreover, on an inner peripheral surface of the rotating knob 7, a base portion 71 that protrudes toward the center axis Ax and a claw portion 72 that protrudes from the base portion 71 toward the proximal end side Ar2, and that is capable of elastic deformation in a direction of diameter of the rotating knob 7 about the base portion 71 as the base point are arranged on the distal end side Ar1 as illustrated n FIG. 3. The rotating knob 7 is attached to the holding portion 9 as the end portion of the holding portion 9 on the distal end side Ar1 is inserted from the proximal end side Ar2, and the claw portion 72 engages with the flange portion 91. That is, the rotating knob 7 is attached to the holding portion 9 by the snap-fit mechanism. Therefore, it becomes possible to arrange the switch 63 close to the rotating knob 7 compared to a structure in which the rotating knob 7 is attached to the housing 6.

According to a rotation operation to the rotating knob 7 by an operator, the holding portion 9 rotates with the rotating knob 7 about the center axis Ax. Moreover, the vibration transmission member 10 and the sheath 8 rotate with the holding portion 9 about the center axis Ax because ey are attached to the holding portion 9.

On the outer peripheral surface of the holding portion 9, an O-ring 92 (FIG. 3) having elasticity attached to prevent unintended rotation of the rotation knob 7, the holding portion 9, the vibration transmission member 10, and the sheath 8 about the center axis Ax. The O-ring 92 abuts on an inner peripheral surface of the housing 6. That is, by using friction between the O-ring 92 and the housing 6, unintended rotation of the rotating knob 7 and the like about the center axis Ax is prevented.

The cap 11 is made from a resin material, such as polyetheretherketone (PEEK) having electric insulation, and has a substantially cylindrical shape surrounding the center axis Ax. The cap 11 is attached to the distal end of the sheath 8.

The sheath 8 and the cap 11 correspond to a cover member. Moreover, the cap 11 corresponds to a tubular portion.

Details of the shape of the cap 11 will be explained in "About Distal End Portion of Treatment Instrument" described later.

The vibration transmission member 10 corresponds to a shaft. This vibration transmission member 10 is made from an electrically conductive material, and has a long shape extending along the center axis Ax. Moreover, the vibration transmission member 10 is inserted in the sheath 8, the holding portion 9, and the cap 11 in state in which an end portion 101 (hereinafter, denoted as end effector 101) on the distal end side Ar1 is exposed to the outside, and is fixed to the holding portion 9. Furthermore, the end portion of the vibration transmission member 10 on the proximal end side Ar2 is connected to a bolt-clamped Langevin transducer (BLT) constituting the ultrasound transducer 5. The vibration transmission member 10 transmits an ultrasonic vibrations generated by the ELT from the end portion on the proximal end side Ar2 to the end portion on the distal end side Ar1. In the present embodiment, the ultrasonic vibration is a vertical vibration vibrating in a direction along the center axis Ax.

Details of the shape of the end effector 101 will be explained in "About Distal End Portion of Treatment Instrument" described later.

The ultrasound transducer 5 is inserted into the proximal-end-side housing portion 611 from the proximal end side Ar2 of the proximal-end-side housing portion 611, and is detachably connected to the proximal-end-side housing portion 611. This ultrasound transducer 5 has a BLT that generates an ultrasonic vibration according to a supply of a driving signal, which is an alternating current, although specific illustration thereof is omitted.

Configuration of Control Device

To the control device 3, the treatment instrument 2 is detachably connected by the electric cable C. The control device 3 overall controls operation of the treatment instrument 2 as described below, according to an operation signal (instrument start operation) input from the switch 63 through the electric cable C.

The control device 3 outputs a driving signal to the BLT constituting the ultrasound transducer 5 through the electric cable C, Thus, the BLT generates an ultrasonic vibration (vertical vibration). Moreover, the end effector 101 vibrates at a desired amplitude by the vertical vibration. To the target site in contact with the end effector 101, the ultrasonic vibration is applied from the end effector 101. In other words, an ultrasonic energy is applied to the target site from the end effector 101.

Furthermore, the control device 3 is connected to a return electrode (not illustrated) by an electric cable (not illustrated). The return electrode is attached to a surface of a subject. The control device 3 outputs a high frequency signal, which is a high frequency electric power, to a portion between the vibration transmission member 10 and the return electrode through the electric cable C. Thus, a high frequency electric current flows through the target site positioned between the end effector 101 and the return electrode. In other words, a high frequency energy is applied to the target site from the end effector 101, About Distal End Portion of Treatment Instrument Next, a distal end portion of the treatment-instrument main unit 4 will be explained.

Figure 4:
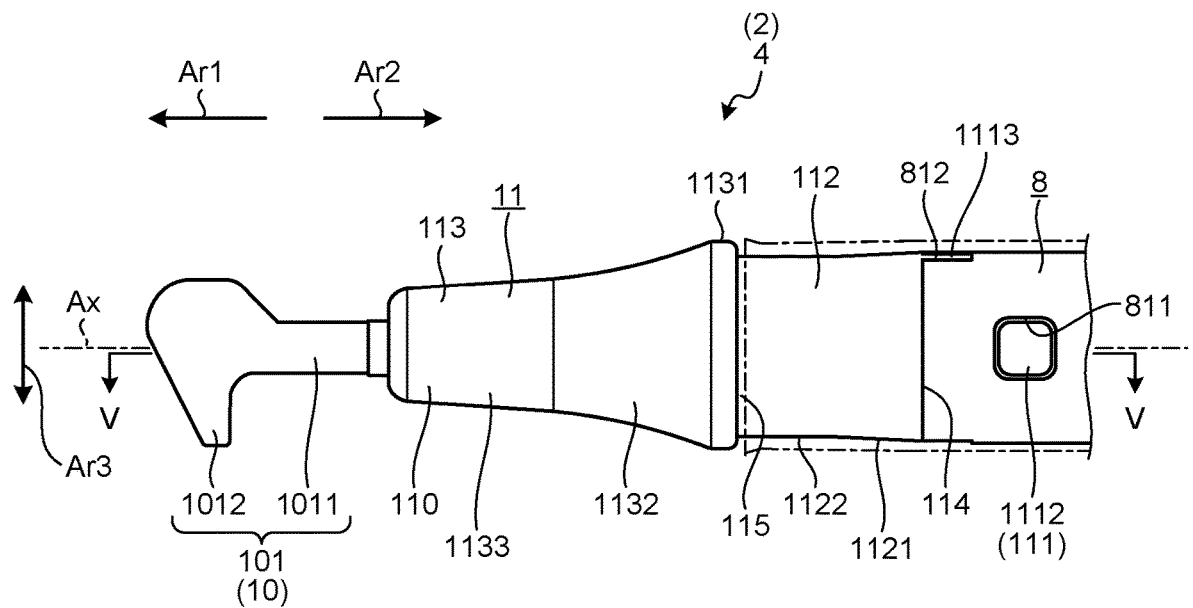
FIG. 4 is a diagram illustrating a distal end portion of a treatment-instrument main unit.
Figure 5:
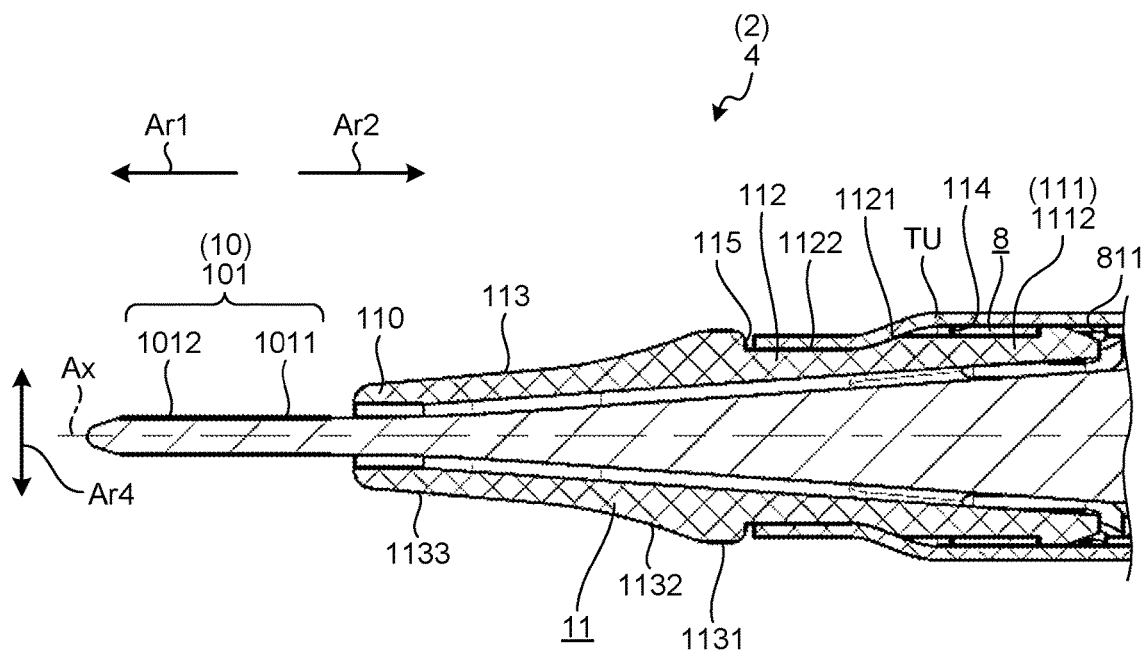
FIG. 5 is a diagram illustrating the distal end portion of the treatment-instrument main unit.

FIG. 4 and FIG. 5 are diagrams illustrating the distal end portion of the treatment-instrument main unit Specifically, FIG. 4 illustrates an external view of the distal end portion of the treatment-instrument main unit 4. In FIG. 4, for convenience of explanation, a tube TU is illustrated with an alternate long and short dash line. FIG. 5 illustrates a cross-section taken along a line v-v in FIG. 4.

In FIG. 4 and FIG. 5, two directions perpendicular to the center axis Ax are denoted as first direction Ar3 and second direction Ar4. The first direction Ar3 is a vertical direction in FIG. 4, The second direction Ar4 is a vertical direction in FIG. 5.

First, the shape of the end effector 101 will be explained.

The end effector 101 includes, as illustrated in FIG. 4, a pillar portion 1011 that extends along the center axis Ax, and a hook portion 1012 that protrudes along the first direction Ar3 (downward in FIG. 4) substantially perpendicular to the pillar portion 1011 from an end portion of the pillar portion 1011 on the distal end side Ar1.

That is, an outer dimension of the hook portion 1012 in the first direction Ar3 is larger than the outer dimension of the pillar portion 1011 in the first direction Ar3. Moreover, the outer dimension of the hook portion 1012 in the second direction Ar4 is smaller than the outer dimension in the first direction Ar3.

Next, a structure of the cap 11 will be explained.

Figure 6:
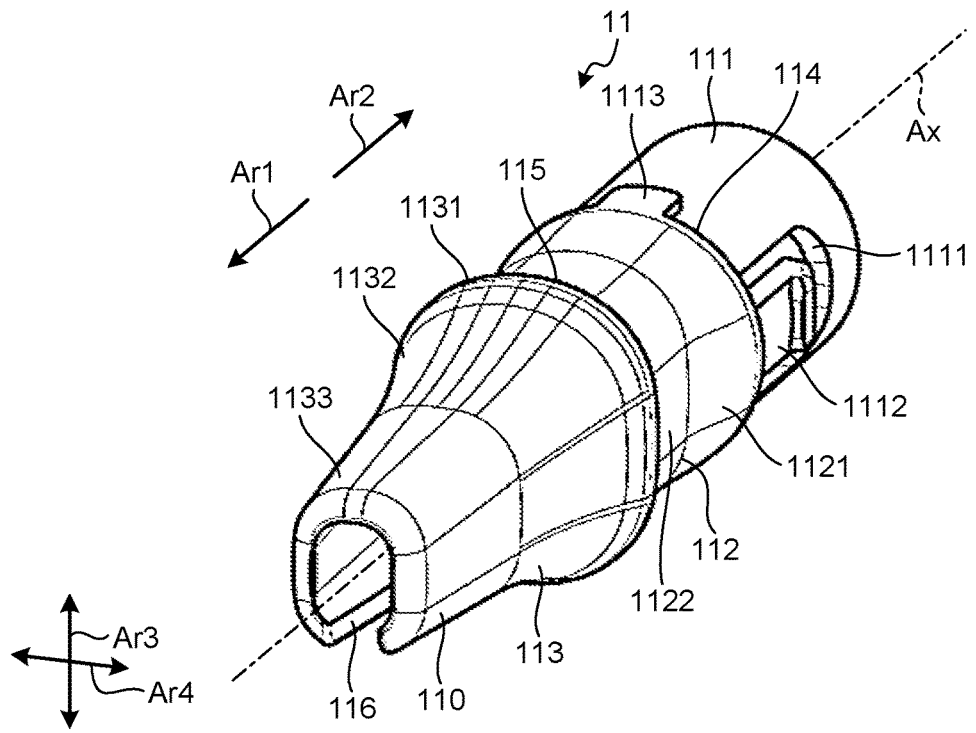
FIG. 6 is a diagram illustrating a cap.
Figure 7:
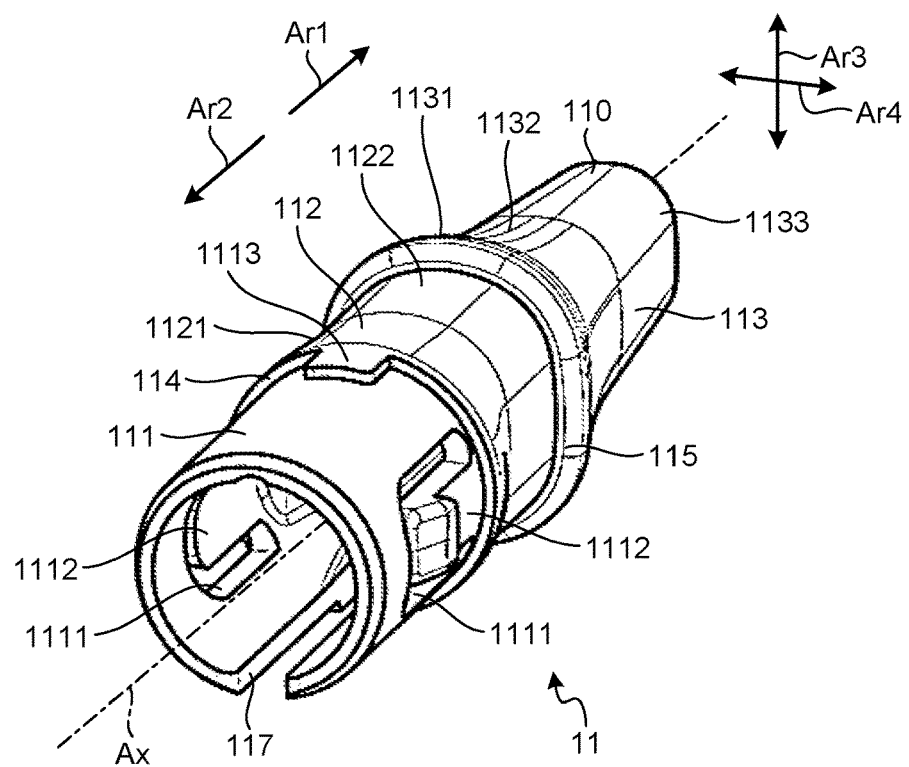
FIG. 7 is a diagram illustrating a cap.

FIG. 6 and FIG. 7 are diagrams illustrating the cap 11.

The cap 11 includes an engaging portion 111, connecting portion 112, and an exposed portion 113 as illustrated in FIG. 4 to FIG. 7.

The engaging portion 111 has a cylindrical s ape coaxial with center axis Ax. In the present embodiment, the outer dimension of the engaging portion 111 is a little smaller than the inner dimension of the sheath 8. Moreover, respective inner dimensions of the engaging portion 111, the connecting portion 112, and the exposed portion 113 are smaller than the outer dimension of the hook portion 1012 in the first direction Ar3.

In this engaging portion 111, a pair of notch portions 1111 that respectively pierce through from the outer peripheral surface to the inner peripheral surface are arranged as illustrated in FIG. 6 or FIG. 7. These pair of notch portions 1111 respectively have a U-shape, Inside the U-shape of the notch portion 1111, a claw portion 1112 that extends from the distal end side Ar1 to the proximal end side Ar2, and that is capable of elastic deformation in a direction of diameter of the engaging portion 111 about a based portion of the distal end side Ar1 as a base point is formed. The pair of the notch portions 1111 (pair of the claw portions 1112) are arranged at rotationally symmetric positions by 180° about the center axis Ax.

The connecting portion 112 is a portion connecting an end portion in the engaging portion 111 on the distal end side Ar1 and an end portion in the exposed portion 113 on the proximal end side Ar2, and as a substantially cylindrical shape surrounding the center axis Ax. In the connecting portion 112, an end portion on the proximal end side Ar2 connected to the engaging portion 111 has an outer diameter larger than the engaging portion 111. That is, on an outer peripheral surface of the cap 11, a first step portion 114 (FIG. 4 to FIG. 7) is arranged between the connecting portion 112 and the engaging portion 111.

On the outer peripheral surface of the engaging portion 111, a positioning portion 1113 (FIG. 4, FIG. FIG. 7) that juts out and extends from the first step portion 114 toward the proximal end side Ar2 is arranged.

Moreover, the outer peripheral surface of the connecting portion. 112 is formed by a first slant surface 1121 and a first distal-end outer-peripheral surface 1122 continuously arranged from the proximal end side Ar2 toward the distal end side Ar1 as illustrated in FIG. 4 to FIG. 7.

The first slant surface 1121 is a surface in which a diameter dimension decreases toward the distal end side Ar1 from a position abutting on the first step portion 114.

The first distal-end outer-peripheral surface 1122 is a surface that linearly extends toward the distal end side Ar1 along the center axis Ax from a position abutting on the first slant surface 1121.

The exposed portion 113 has a substantially cylindrical shape surrounding the center axis Ax, and is arranged at an end portion of the connecting portion 112 on the distal end side Ar1. In this exposed portion 113, an end portion on the proximal end side Ar2 connected to the connecting portion 112 has a larger outer diameter dimension than the first distal-end outer-peripheral surface 1122. That is, on the outer peripheral surface of the cap 11, a second step portion 115 (FIG. 4 to FIG. 7) is arranged between the exposed portion 113 and the connecting portion 112. The outer peripheral surface of the exposed portion 113 has a protruded surface 1131 that juts out toward the outside in the direction of diameter of the exposed portion 113. This protruded surface 1131 is a surface abutting on the second step portion 115 and corresponds to a protruded portion.

Moreover, the outer peripheral surface of the exposed portion 113 is formed, as illustrated in FIG. 4 to FIG. 7, by the protruded surface 1131, a second slant surface 1132, and a second distal-end outer-peripheral surface 1133 arranged continuously from the proximal end side Ar2 toward the distal end side Ar1.

The protruded surface 1131 is a surface that linearly extends toward the distal end side Ar1 along the center axis Ax from a position abutting on the second step portion 115.

The second slant surface 1132 is a surface in which a diameter dimension decreases toward the distal end side from a position abutting on the protruded surface 1131.

The second distal-end outer-peripheral surface 1133 a surface that substantially linearly extends toward the distal end side Ar1 along the center axis from a position abutting on the second slant surface 1132.

An outer diameter dimension of a distal end portion 110 (FIG. 4 to FIG. 7) having the second distal-end outer-peripheral surface 1133 is smaller than an outer diameter dimension of the engaging portion 111 corresponding to a proximal end portion. Moreover, the outer diameter dimension of the distal end portion 110 is smaller than an outer dimension of the hook portion 1012 in the first direction Ar3 as illustrated in FIG. 4. The distal end portion 110 is made thin, and has a function of providing a field of view for an operator that uses the treatment-instrument main unit 4, or the like.

In the cap 11 explained above, a first slit 116 (FIG. 6) and a second slit 117 (FIG. 7) are arranged on one end side (lower side in FIG. 6, FIG. in the first direction Ar3.

The first slit 116 is a slit that is linearly cut along the center axis from a distal end of the cap 11 to a portion before the protruded surface 1131.

The second slit 117 is a slit that is linearly cut along the center axis Ax from a proximal end of the cap 11 to a portion before the first distal-end outer-peripheral surface 1122.

Width dimensions of the first and the second slits 116 and 117 are a little larger than the outer dimension of the hook portion 1012 in the second direction Ar4.

Finally, a structure of an end portion of the sheath 8 on the distal end side Ar1 will be explained.

In the end portion of the sheath 8 on the distal end side Ar1, a pair of engagement opening portions 811 (FIG. 4, FIG. 5) that respectively pierce through from an outer peripheral surface to an inner peripheral surface, and with which the pair of claw portions 1112 are respectively engaged are arranged.

Furthermore, in the sheath 8, a positioning notch portion 812 (FIG. 4) that is cut toward the proximal end side Art from the distal end, and in which the positioning portion 1113 is inserted is arranged.

On an outer peripheral surface of the sheath 8 and the like, the tube TU (FIG. 4, FIG. 5) is attached.

This tube TU is a heat shrinkable tube made from a resin material having electric insulation.

Manufacturing Method of Treatment Instrument.

Next, a manufacturing method of the treatment instrument 2 will be explained.

Figure 8:
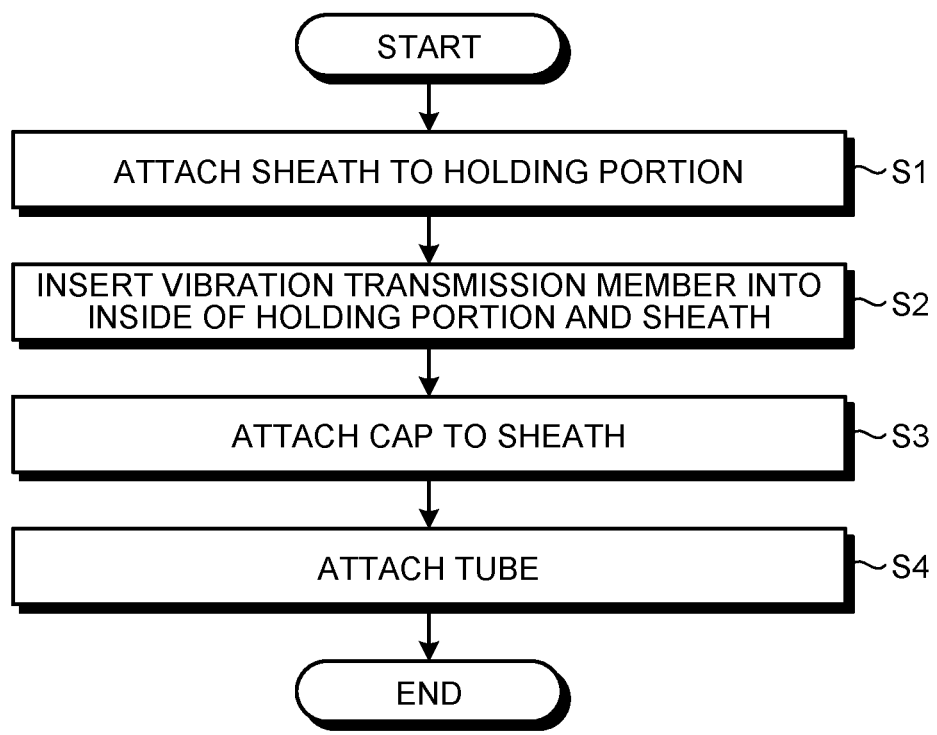
FIG. 8 is a flowchart illustrating a manufacturing method of the treatment instrument.

FIG. 8 is a flowchart illustrating the manufacturing method of the treatment instrument 2. FIG. 9 to FIG. 16 are diagrams explaining the manufacturing method of the treatment instrument 2. FIG. 12 to FIG. 16 are cross-sections of the vibration transmission member 10 and the like cut along a plane including a point of the hook portion 1012 (end portion on a lower side in FIG. 12 to FIG. 16) and the center axis Ax.

Figure 9:
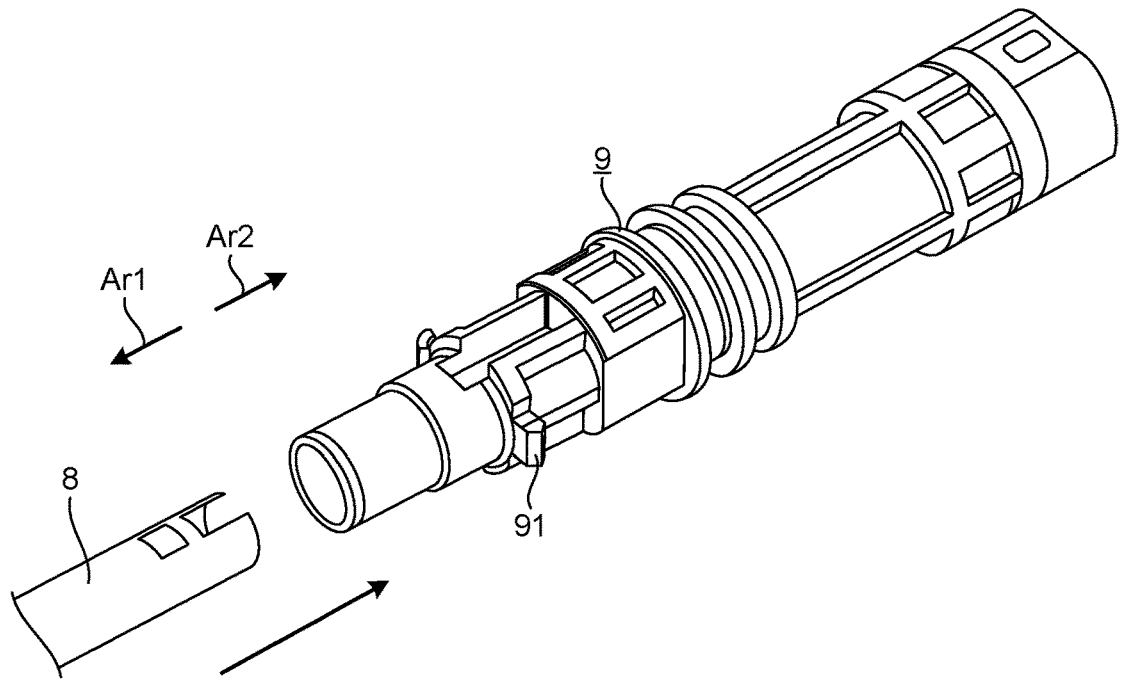
FIG. 9 is a diagram explaining the manufacturing method of the treatment instrument.
Figure 10:
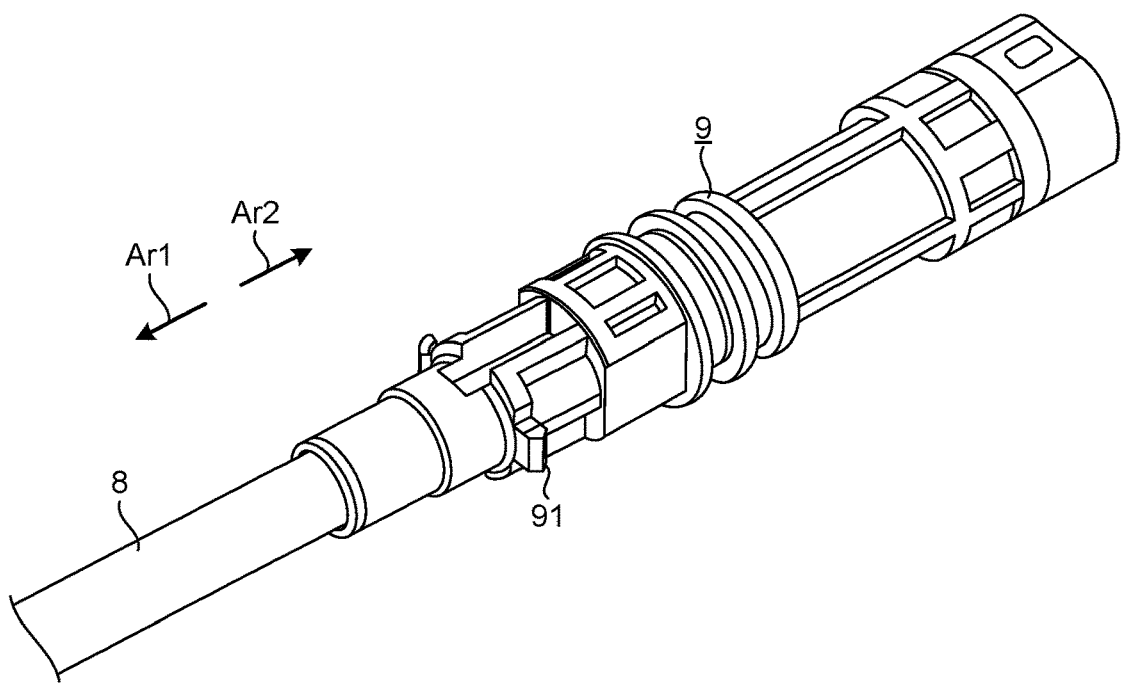
FIG. 10 is a diagram explaining the manufacturing method of the treatment instrument.

First, an operator inserts an end portion of the sheath 8 on the proximal end side Ar2 into the inside of the holding portion 9 from the distal end side Ar1 of the holding portion 9 as illustrated in FIG. 9 (step S1). Thus, the sheath 6 is attached to the holding portion 9 as illustrated in FIG. 10.

Figure 11:
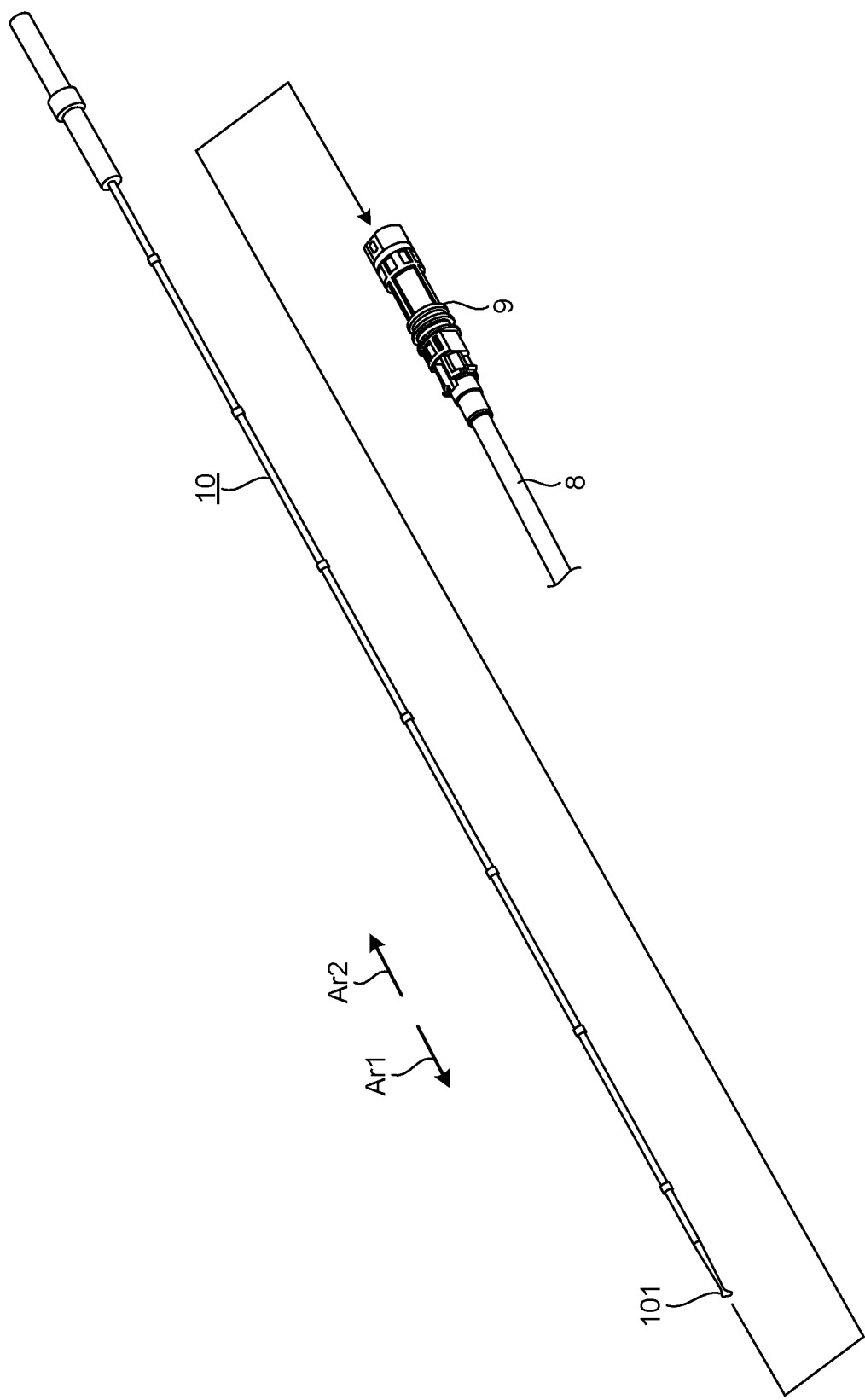
FIG. 11 is a diagram explaining the manufacturing method of the treatment instrument.

After step S1, the operator inserts the end portion of the vibration transmission member 10 on the distal end side Ar1 into the inside of the holding portion 9 and the sheath 8 from the proximal end side Art of the holding portion 9 as illustrated in FIG. 11 (step S2). Thus, the vibration transmission member 10 is attached to the holding portion 9 in a state in which the end effector 101 protrudes out from the distal end side Ar1 of the sheath 8.

After step S2, the operator attaches e cap 11 to the sheath 8 as described below (step S3).

Figure 12:
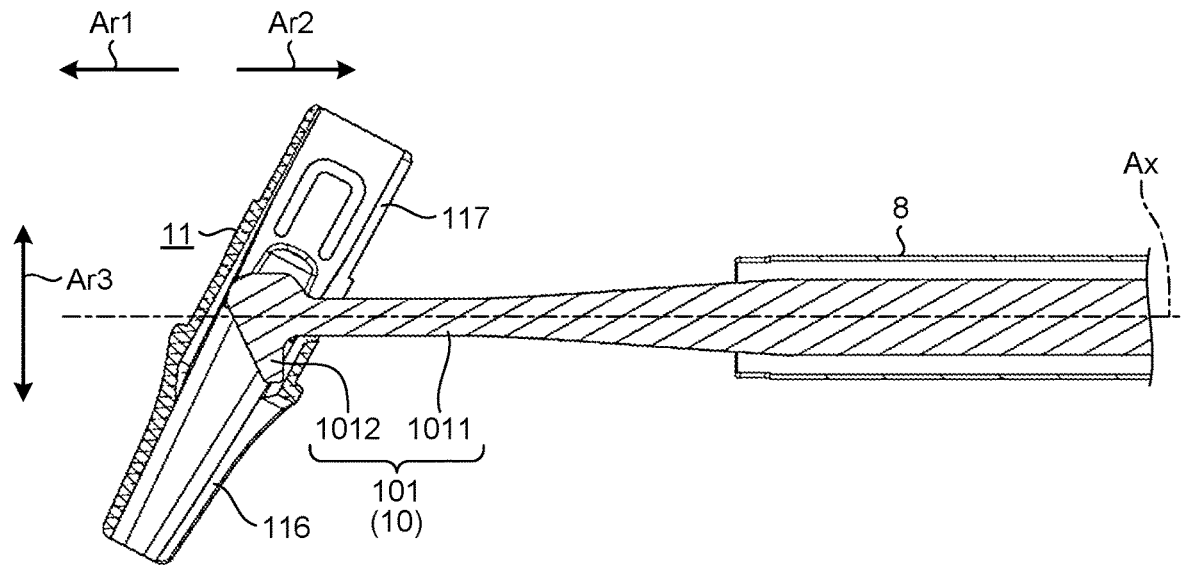
FIG. 12 is a diagram explaining the manufacturing method of the treatment instrument.

First, the operator positions the first and the second slits 116 and 117 on a lower side in FIG. 12 (side of the point of the hook 1012), inclines the cap 11 in such a posture that the distal end side Ar1 is positioned on a lower side in FIG. 12 relative to the proximal end side Ar2. The operator then inserts the hook portion 1012 into the inside of the cap 11 from the second slit 117 of the cap 11 in such a posture.

Figure 13:
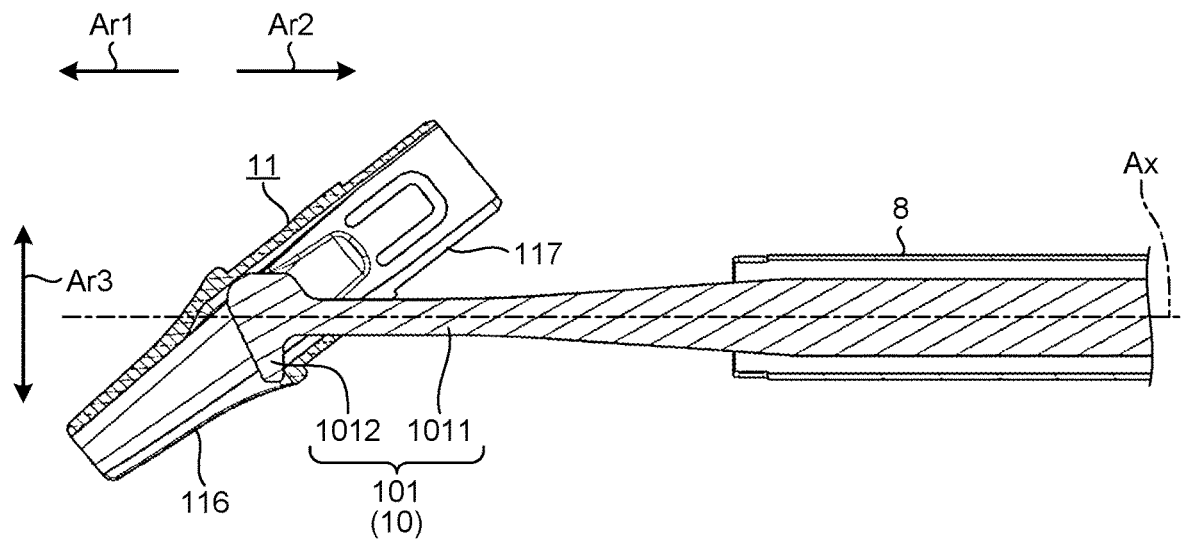
FIG. 13 is a diagram explaining the manufacturing method of the treatment instrument.
Figure 14:
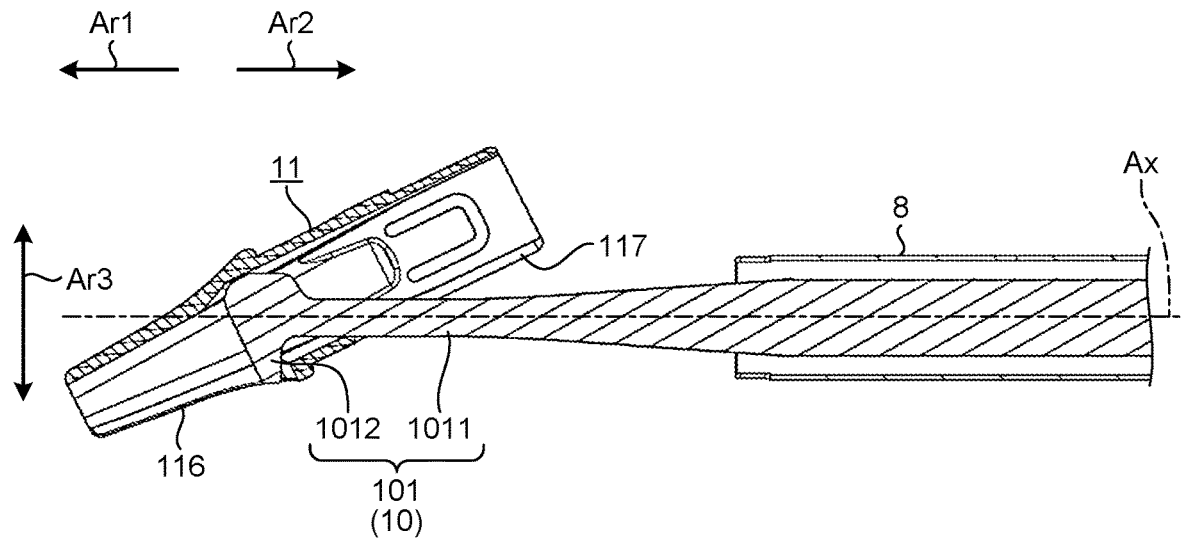
FIG. 14 is a diagram explaining the manufacturing method of the treatment instrument.
Figure 15:
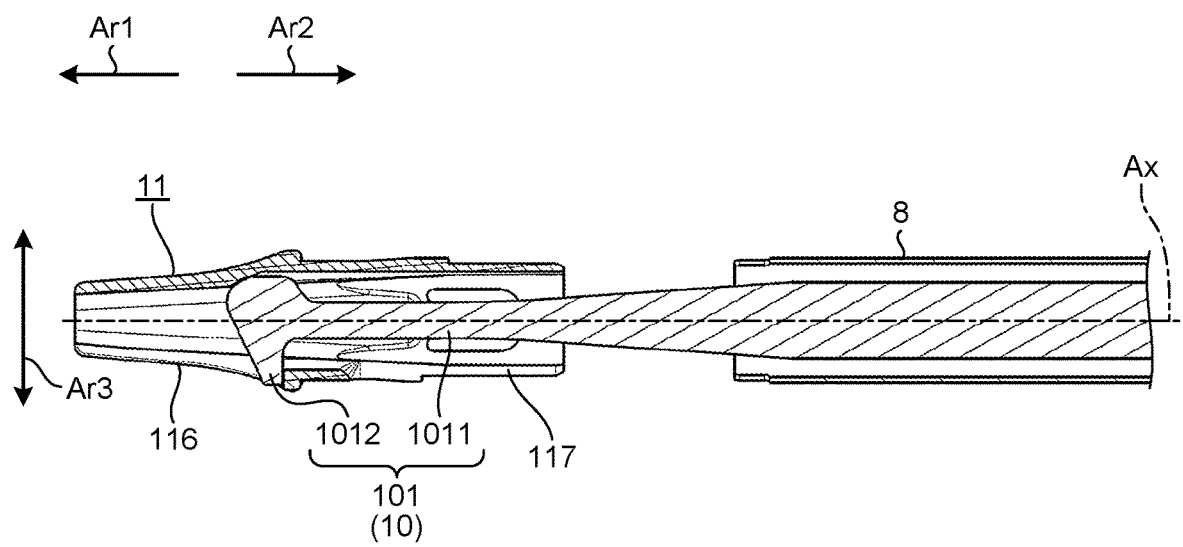
FIG. 15 is a diagram explaining the manufacturing method of the treatment instrument.

Next, the operator rotates the cap 11 as illustrated in FIG. 13, FIG. 14, and FIG. 15, and inserts the pillar portion 1011 into inside of the cap 11 from the second slit 117. Thus, the point in the hook portion 1012 protrudes out to the outside of the cap 11 from the first slit 116. That is, the first and the second slits 116, 117 are slits provided to prevent interference with the end effector 101.

Figure 16:
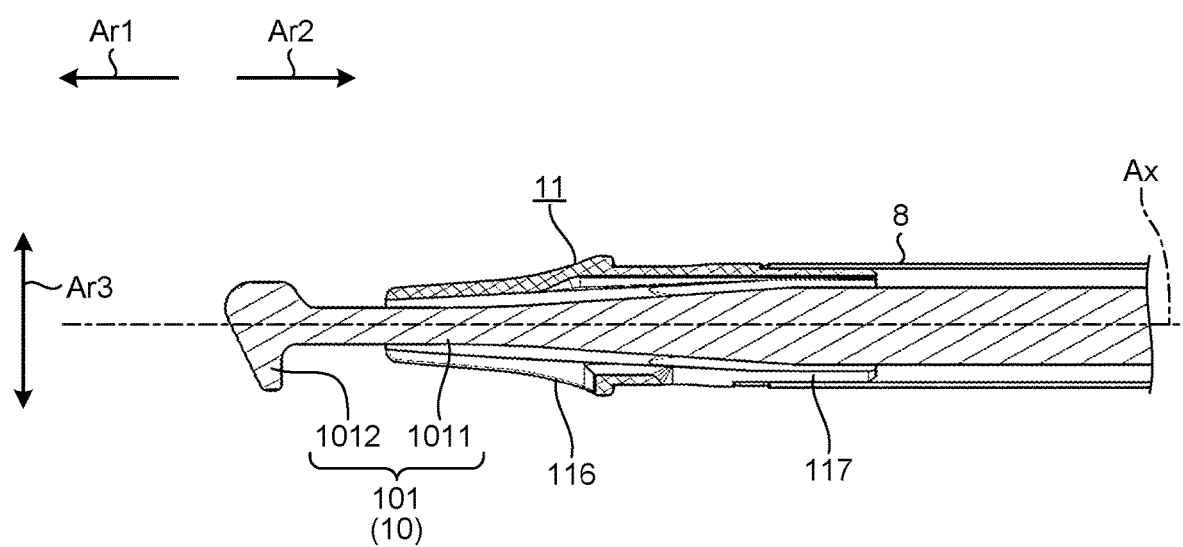
FIG. 16 is a diagram explaining the manufacturing method of the treatment instrument.

Next, the operator moves the cap 11 toward the proximal end side Ar2 as illustrated in FIG. 16, and inserts the engaging portion 111 into the inside of the sheath 8 while inserting the positioning portion 1113 to the positioning notch portion 812. Thus, the hook portion 1012 protrudes toward the distal end side Ar1 from, the cap 11. The cap 11 is attached to the sheath 8 as the claw portion 1112 is engaged with the engagement opening portion 811. That is, the cap 11 is attached to the sheath 8 by a snap-fit mechanism.

After step S3, the operator inserts the end effector 101, the cap 11, the sheath 8, and the end portion of the holding portion 9 on the distal end side Ar1 into the inside of the tube TU from the proximal end side Ar2 of the tube TU. The operator then applies heat to the tube TU to make the tube TU shrink in the direction of diameter dimension of the tube TU (step S4).

A distal end of the tube TU is positioned between the protruded surface 1131 and the first slant surface 1121, that is, on the first distal-end outer-peripheral surface 1122 as illustrated in FIG. 4 or FIG. 5. In the present embodiment, the diameter dimension in the protruded surface 1131 is substantially the same as an outer diameter dimension of the tube TU at the distal end as illustrated in FIG. 4. Moreover, the outer diameter dimension at the protruded surface 1131 may be equal to or smaller than the outer diameter dimension of the tube TU at the distal end, or may be equal to or larger than the outer diameter dimension of the tube TU at the distal end.

Moreover, the proximal end of the tube TU is positioned on an outer peripheral surface of the end portion of the holding portion 9 on the distal end side Ar1 as illustrated in an enlarged view of FIG. 2, That is, gap between th sheath 8 and the holding portion 9 is protected by the tube TU.

As described above, the tube TU is arranged at a position to cover both the outer peripheral surface of the sheath 8 and the outer peripheral surface of the cap 11 straddling a boundary between the sheath 8 and the cap 11. Moreover, in the sheath 8 and the cap 11, the engaging portion 111 and a part of the first slant surface 1121 are an overlap area overlapping in the radial direction. The tube TU covers the overlap area.

According to the present embodiment explained above, following effects are obtained.

In the present embodiment, the cap 11 has the distal end portion 110, an outer diameter dimension of which is smaller than an outer diameter dimension of the engaging portion 111. Moreover, the outer diameter dimension at the distal end portion 110 is smaller than the outer dimension of the hook portion 1012 in the first direction Ar1. Therefore, according to the present embodiment, the distal end portion 110 can be made thin, and a field of view for an operator that uses the treatment-instrument main unit 4 or the like can be acquired.

Furthermore, in the cap 11, the first and the second slits 116, 117 are provided. Therefore, while avoiding interference with the end effector 101, the cap 11 can receive the end effector 101 inserted thereinside.

Particularly, the first and the second slits 116, 117 are not slits piercing through from the distal end to the proximal end of the cap 11. Therefore, it is possible to prevent reduction of strength of the cap 11 more than necessary. Moreover, because it is possible to prevent the cap 11 from being deformed more than necessary, dropping off of the cap 11 due to deformation can be prevented.

Furthermore, the treatment instrument 2 includes the tube TU that is arranged at a position enabling to cover both the outer peripheral surface of the sheath 8 and the outer peripheral surface of the cap 11 straddling the boundary between the sheath 8 and the cap 11, and that shrinks in the direction of diameter perpendicular to the center axis Ax. That is, the cap 11 is in a state of being fastened by the shrinking force of the tube TU. Accordingly, it is possible to prevent dropping off of the cap 11 from the sheath 8.

Moreover, the cap is attached to the sheath 8 by the snap-fit mechanism by the engaging portion 111. Therefore, the cap 11 can be attached to the sheath S easily. The tube TU covers the overlap area, which is a portion corresponding to the engaging portion 111. Therefore, the overlap area is protected by the tube TU, and even when an external force is applied to the overlap area, an engagement state of the cap 11 with respect to the sheath 8 can be favorably maintained. That is, dropping off of the cap 11 from the sheath 8 can be effectively prevented.

Furthermore, the tube TU covers the first slant surface 1121. Therefore, it forms a structure that the first slant surface 1121 is caught by the tube TU, and dropping off of the cap 11 from the sheath 8 can be effectively prevented.

Moreover, the diameter dimension at the protruded surface 1131 is substantially the same as the outer diameter dimension of the tube TU at the distal end. Therefore, a structure in which the outer peripheral surface of the cap 11 and the outer peripheral surface of the tube TU are connected on an identical plane without a gap. That is, dropping off of the cap 11 from the sheath 8 caused because something is caught by the gap does not occur.

Furthermore, the cap 11 is made from a resin material having electric insulation. Therefore, it is not necessary to cover the cap 11 up to the distal end with the tube TU. That is, because the distal end portion is not covered with the tube TU, the distal end portion can be race thin, and a field of view for an operator that uses the treatment-instrument main unit 4 or the like can be provided.

Next, another exemplary embodiment will be explained.

In the following explanation, identical reference symbols are assigned to components identical to those of the embodiment described above, and detailed explanation thereof will be omitted or simplified.

The present embodiment differs from the embodiment described above in a structure of the distal end portion (structures of the sheath 8 and the cap 11) of the treatment-instrument main unit 4.

In the following, for convenience of explanation, the treatment instrument 2 according to the present embodiment will be denoted as treatment instrument 2A. Moreover, the treatment-instrument main unit 4 according to the present embodiment will be denoted as treatment-instrument main unit 4A. Furthermore, the sheath 8 according to the present embodiment will be denoted as sheath 8A. Moreover, the cap 11 according to the present embodiment will be denoted as cap 11A.

The sheath 8A and the cap 11A correspond to a cover member. Moreover, the cap 11A corresponds to a tubular portion.

Figure 17:
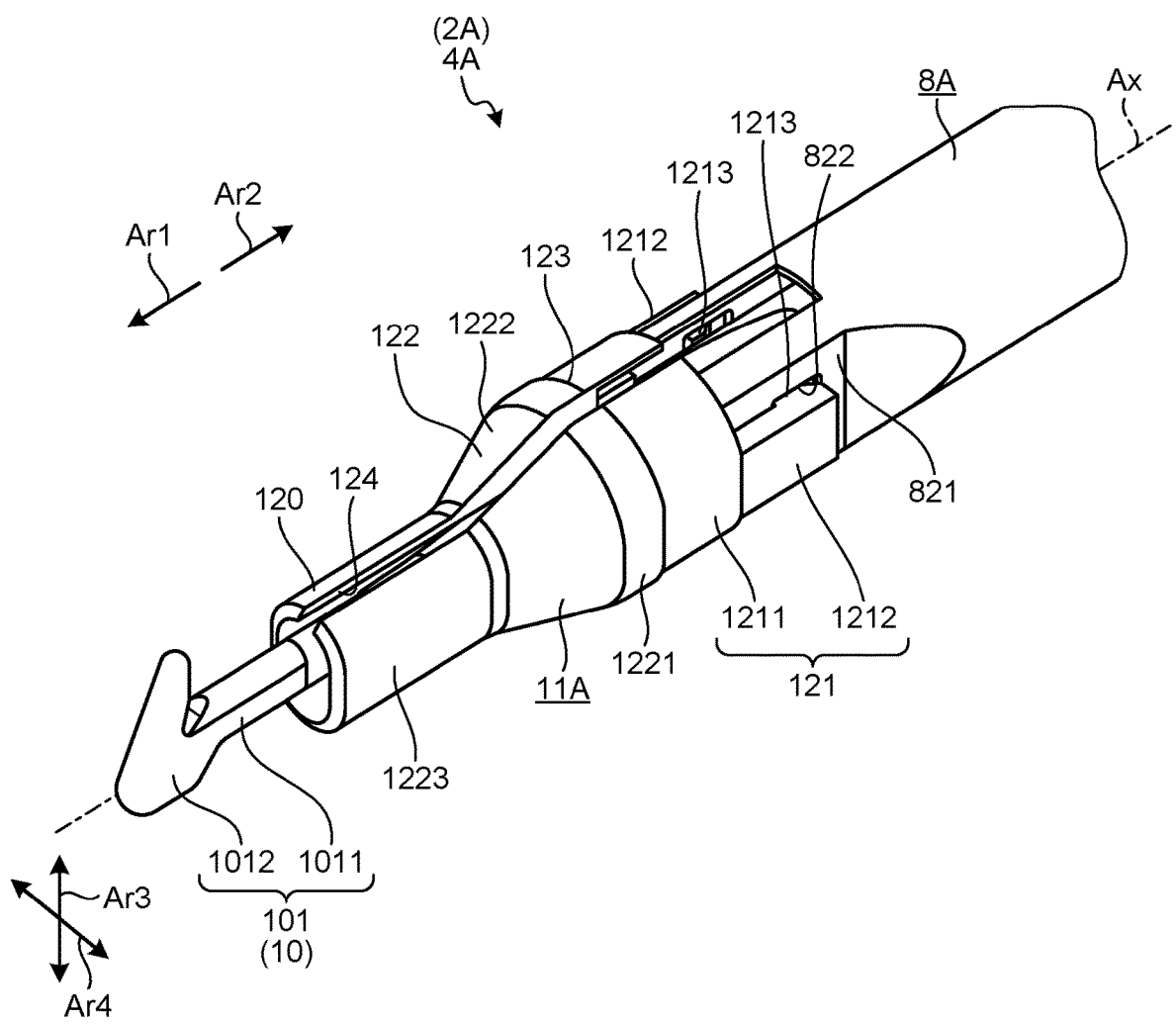
FIG. 17 is a diagram illustrating a distal end portion of a treatment-instrument main unit according to an exemplary embodiment.
Figure 18:
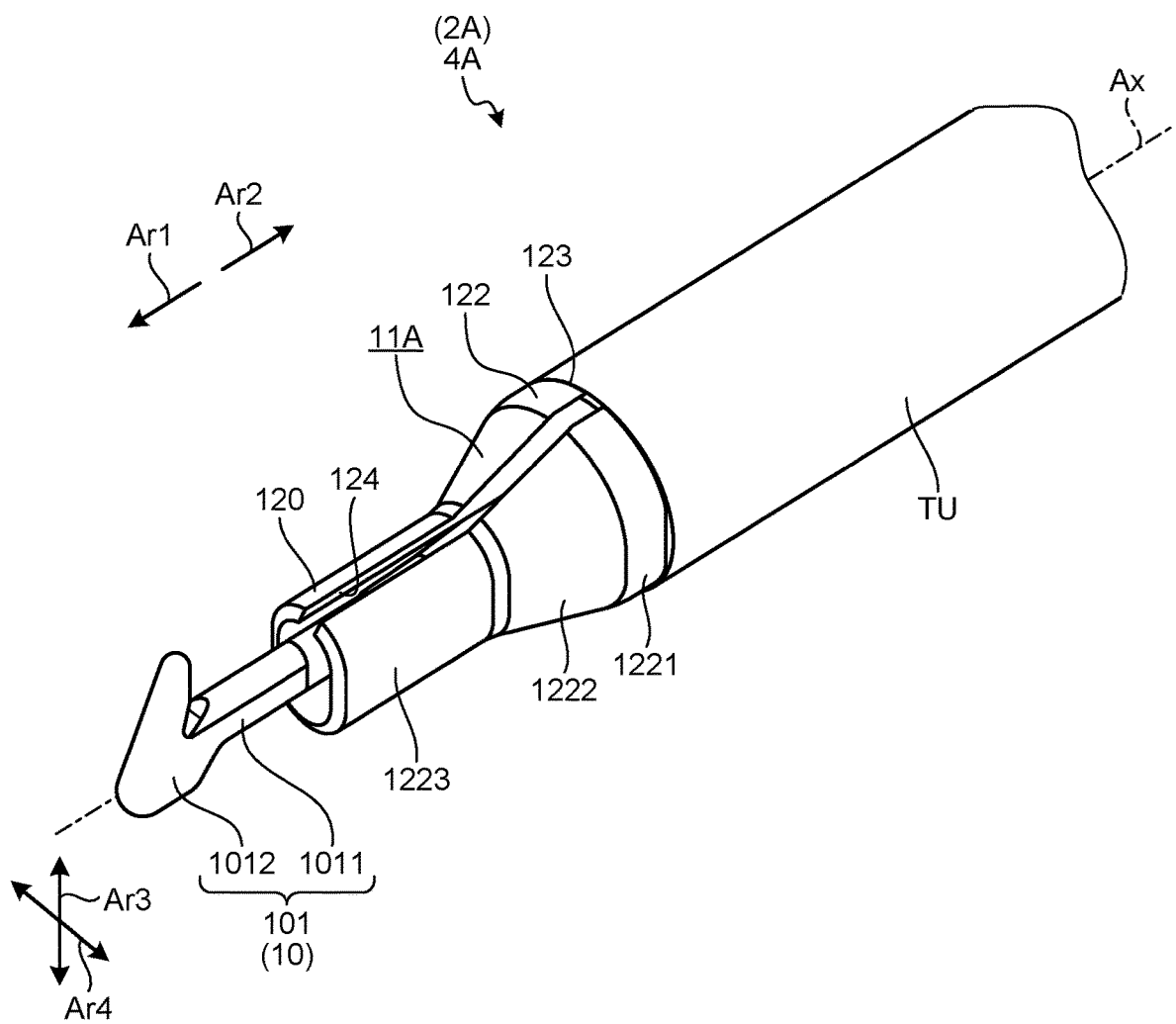
Figure 19:
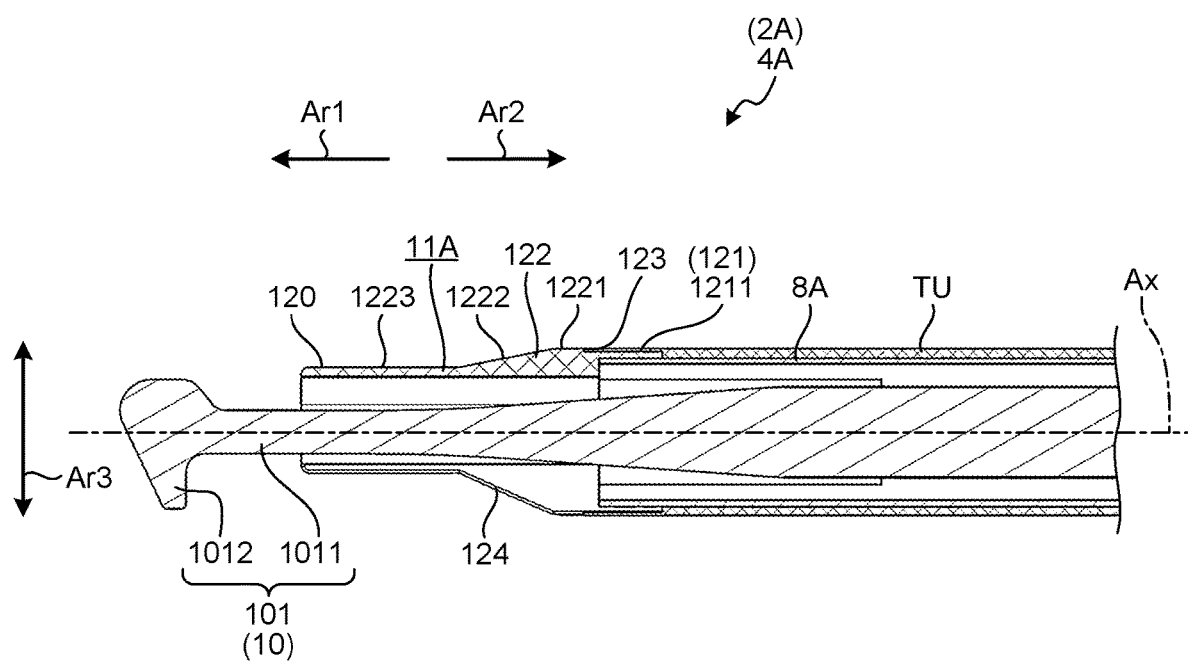
FIG. 19 is a diagram illustrating a distal end portion of the treatment-instrument main unit according to the exemplary embodiment.

FIG. 17 to FIG. 19 are diagrams illustrating a distal end portion of the treatment-instrument main unit 4A according to the present embodiment. Specifically, FIG. 17 and FIG. 18 are diagrams illustrating an external view of the distal end portion of the treatment-instrument main unit 4A. While FIG. 17 illustrates a state in which the tube TU is removed, FIG. 18 illustrates a state in which the tube TU is attached. FIG. 19 is a cross-section of the distal end portion of the treatment-instrument main unit 4A cut along a plane including the point of the hook portion 1012 and the center axis Ax.

The cap 11A is made from a resin material, such as PEEK having electric insulation. This cap 11A includes an engaging portion 121 and an exposed portion 122 as illustrated in FIG. 17 to FIG. 19.

The engaging portion 121 includes an engaging-portion main unit 1211 and a pair of arm portions 1212 as illustrated in FIG. 17 or FIG. 19.

The engaging-portion main unit 1211 has a cylindrical shape coaxial with the center axis Ax. In the present embodiment, an inner diameter dimension of the engaging-portion main unit 1211 is a little larger than an outer diameter dimension of the sheath 8A.

The pair of the arm portions 1212 oppose to each other from a proximal end of the engaging-portion main unit 1211 and protrude toward the proximal end side Ar2, and is capable of elastic deformation in a direction of becoming close to and apart from each other, from a proximal end on the distal end side Ar1 as a base point. In these pair of the arm portions 1212, convex portions 1213 (FIG. 17) are arranged respectively on surfaces opposing to each other on the proximal end side Ar2.

The exposed portion 122 has a substantially cylindrical shape surrounding the center axis Ax, and is arranged at an end portion of the engaging-portion main unit 1211 on the distal end side. In the present embodiment, an inner diameter dimension at the exposed portion 122 is smaller than the outer dimension of the hook portion 1012 in the first direction Ar3. In this exposed portion 122, an end portion on the proximal end side Ar2 connected to the engaging-portion main unit 1211 has a larger outer diameter dimension than the engaging-portion main unit 1211. That is, on the outer peripheral surface of the cap 11A, a step portion 123 (FIG. 17 to FIG. 19) is arranged between the exposed portion 122 and the engaging-portion main unit 1211. Hereinafter, for convenience of explanation, a surface abutting on the step portion 123 on the outer peripheral surface of the exposed portion 122 will be denoted as protruded surface 1221.

Moreover, an outer peripheral surface of the exposed portion 122 is formed by the protruded surface 1221, a slant surface 1222, and a distal-end outer-peripheral surface 1223 continuously arranged from the proximal end side Art toward the distal end side Ar1 as illustrated in FIG. 17 to FIG. 19.

The protruded surface 1221 is a surface that linearly extends from a position abutting on the step portion 123 toward the distal end side Ar1 along the center axis Ax.

The slant surface 1222 is a surface in which a diameter dimension gradually decreases from the position abutting on the protruded surface 1221 toward the distal end side Ar1.

The distal-end outer-peripheral surface 1223 is a surface that linearly extends from a position abutting on the slant surface 1222 toward the distal end side Ar1 along the center axis Ax.

An outer diameter dimension at a distal end portion 120 having the distal-end outer-peripheral surface 1223 (FIG. 17 to FIG. 19) is smaller than an outer diameter dimension at the engaging-portion main unit 1211 corresponding to a proximal end portion. Moreover, an outer diameter dimension at the distal end portion 120 is smaller than an outer dimension of the hook portion 1012 in the first direction Ar3. The distal end portion 120 is made thin, and thereby has a function of providing a field of view for an operator that uses the treatment-instrument main unit 4A or the like.

In the cap 11A explained above, a slit 124 (FIG. 17, FIG. 18) that is cut linearly along the center axis Ax from a distal end to a proximal end is arranged on an end side in the first direction Ar3. This slit 124 corresponds to a first slit.

A width dimension of this slit 124 is a little larger than the outer dimension of the hook portion 1012 in the second direction Ar4.

At an end portion of the sheath 8 on the distal end side Ar1, as illustrated in FIG. 17, a pair of flat portions 821 are arranged by processing a side wall portion.

The pair of the flat portions 821 are flat planar portions that respectively extend toward the proximal end side Ar2 from the distal end in the sheath 8A, and that are parallel to each other. A separation distance between outer surfaces of these flat portions 821 is substantially e same as a separation distance between surfaces opposing to each other in the pair of the arm portions 1212. In these pair of the flat portions 821, a pair of engagement opening portions 822 (FIG. 17) that pierce through from a front surface to a rear surface, and with which the pair of convex portions 1213 are engaged are arranged, respectively.

In a manufacturing method of the treatment instrument 2A according to the present embodiment, step S3 is different from the manufacturing method (FIG. 8) of the treatment instrument 2 explained in the embodiment described above.

At step S3 according to the present embodiment, an operator inserts the end effector 101 into the inside of e cap 11A from the proximal end side Ar2 of the cap 11A in such a state that the point of the hook portion 1012 fits in the slit 124. The operator makes the hook portion 1012 protrudes out from the distal end side Ar1 of the cap 11A. Moreover, the operator moves the cap 11A to the proximal end side Ar2, and slides the pair of the convex portions 1213 on the outer surfaces of the pair of the flat portions 821, to insert the end portion of the sheath 8A on the distal end side Ar1 into the inside of the engaging-portion main unit 1211. The cap 11A is attached to the sheath 8A as the convex portion 1213 engages with the engagement opening portions 822. That is, the cap 11A is attached to the sheath 8A by snap-fit mechanism.

At step S4, in a state in which the tube TU is attached, the distal end of the tube TU is positioned on the outer peripheral surface of the engaging-portion main unit 1211 as illustrated in FIG. 19. In the present embodiment, a diameter dimension at the protruded surface 1221 is substantially the same as an outer diameter dimension of the tube TU at the distal end as illustrated in FIG. 19. Moreover, the diameter dimension at the protruded surface 1221 may be equal to or smaller than the outer diameter dimension of the tube TU at the distal end, or may be equal to or larger than the outer diameter dimension of the tube TU at the distal end.

As described, the tube TU is arranged at a position enabling to cover both the outer peripheral surface of the sheath 8A and the outer peripheral surface of the cap 11A, straddling a boundary between the sheath 8A and the cap 11A. Moreover, in the sheath 8A and the cap 11A, a portion corresponding to the engaging portion 121 is an overlap area that overlaps in a radial direction. The tube TU covers the overlap area.

Also when the treatment-instrument main unit 4A according to the present embodiment explained above is adopted, effects similar to those of the embodiment described above are obtained.

Next, another exemplary embodiment will be explained.

In the following explanation, identical reference symbols are assigned to components identical to those of the embodiments described above, and detailed explanation thereof will be omitted or simplified.

The present embodiment differs from the embodiment described above with respect to FIGS. 1-16 in a structure of the distal end portion of the treatment-instrument main unit 4 (structure of the sheath 8 and the cap 11).

Hereinafter, for convenience of explanation, the treatment instrument 2 according to the present embodiment will be denoted as treatment instrument 2B. Moreover, the treatment-instrument main unit 4 according to the present embodiment will be denoted as treatment-instrument main unit 4B. Furthermore, the sheath 8 according to the present embodiment will be denoted as sheath 8B. Moreover, the cap 11 according to the present embodiment will be denoted as cap 11B.

The sheath 8B and the cap 11B correspond to the cover member. Moreover, the cap 11B corresponds to the tubular portion.

Figure 20:
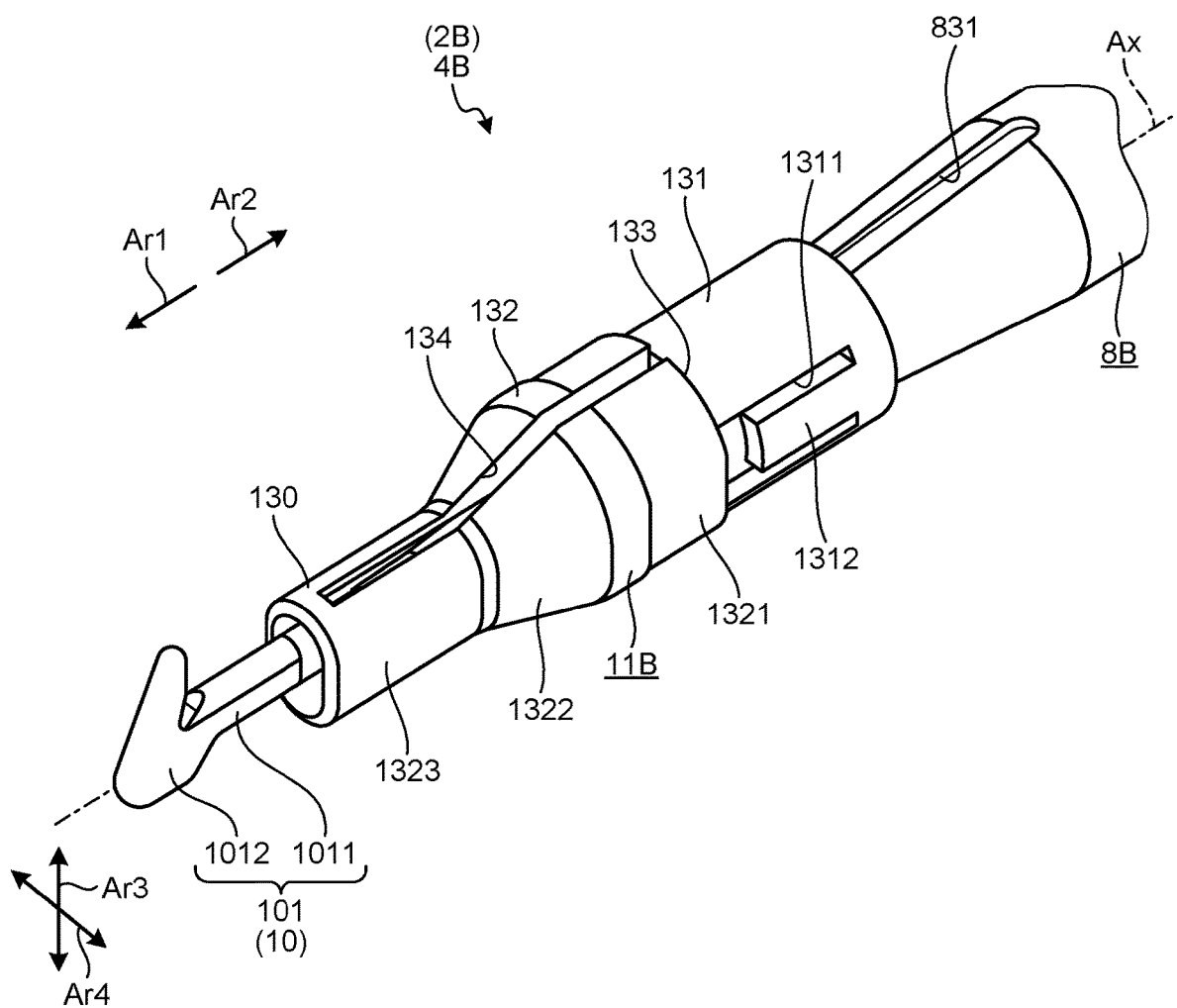
FIG. 20 is a diagram illustrating a distal end portion of a treatment-instrument main unit according to an exemplary embodiment.
Figure 21:
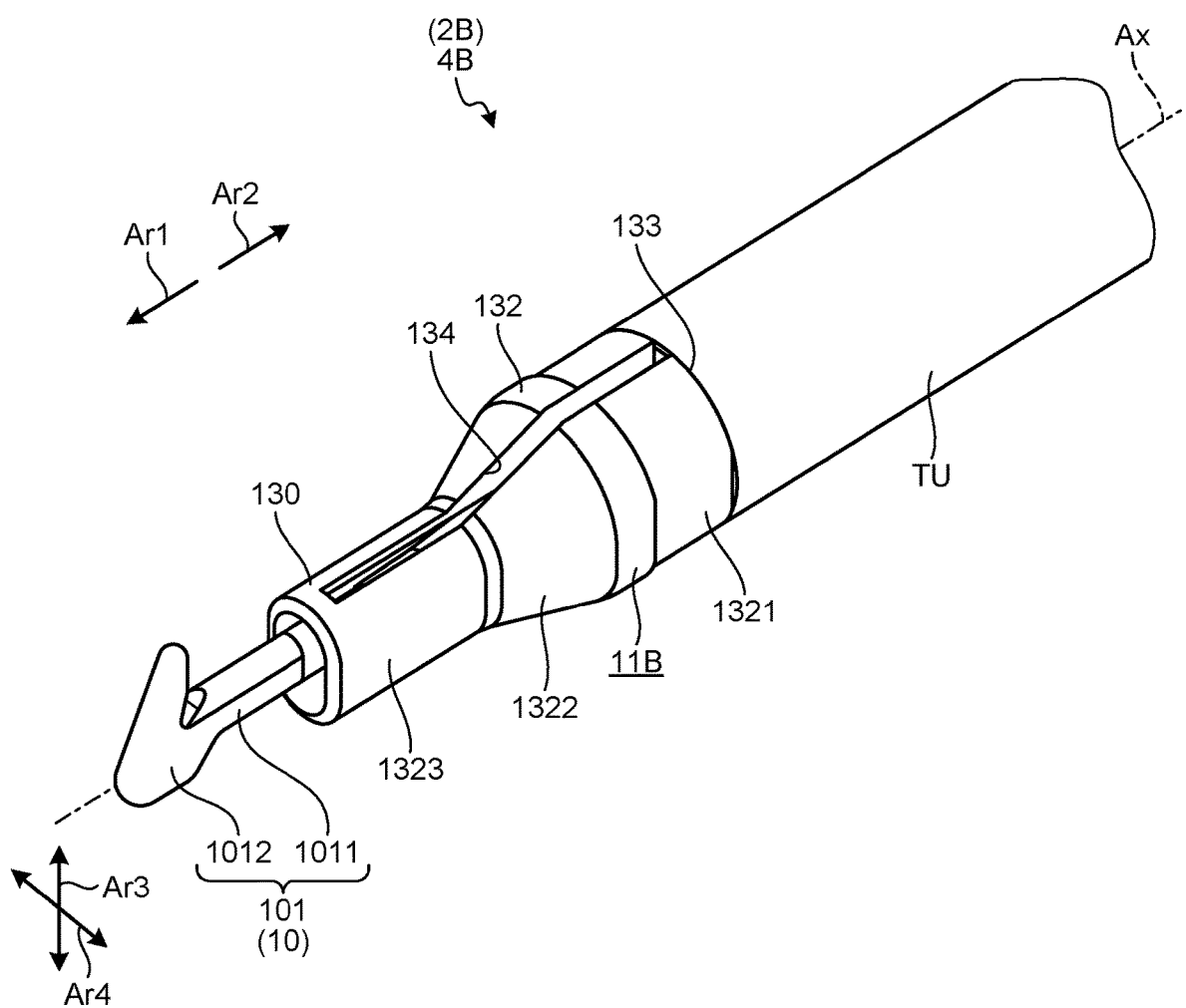
FIG. 21 is a diagram illustrating the distal end portion of the treatment-instrument main unit according to the exemplary embodiment.
Figure 22:
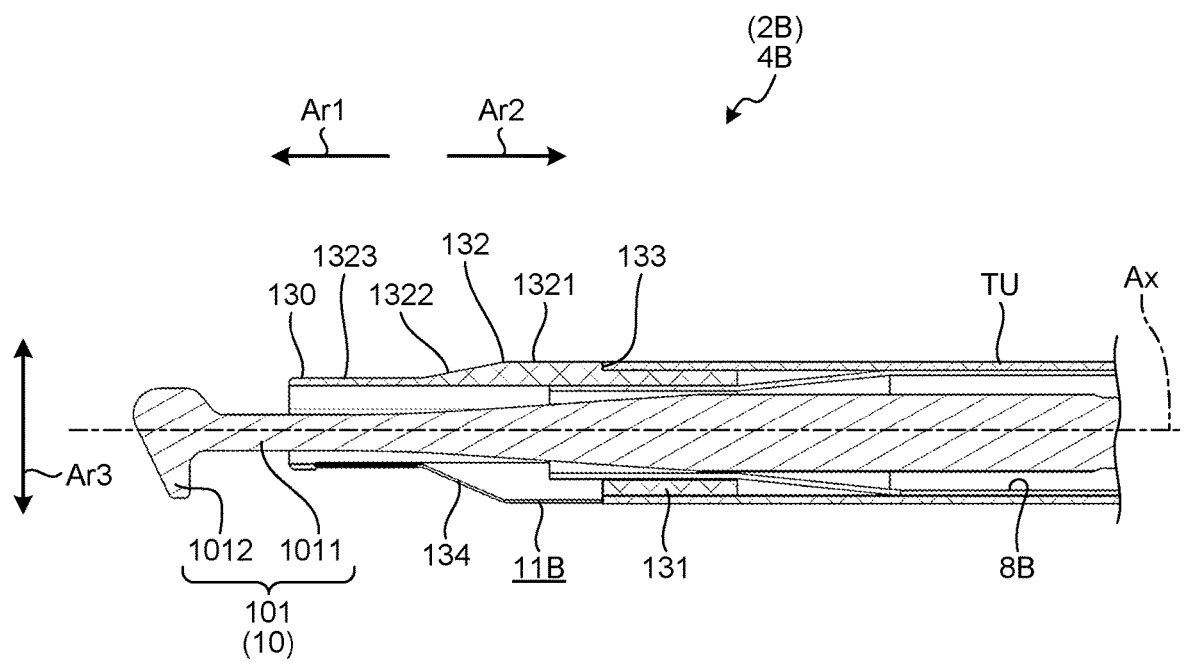
FIG. 22 is a diagram illustrating the distal end portion of the treatment-instrument main unit according to the exemplary embodiment.

FIG. 20 to FIG. 22 are diagrams illustrating a distal end portion of the treatment-instrument main unit. 4B according to the present embodiment. Specifically, FIG. 20 and FIG. 21 are diagrams illustrating an external view of the distal end portion of the treatment-instrument main unit 4B. While FIG. 20 illustrates a state in which the tube TU is removed, FIG. 21 illustrates a state in which the tube TU is attached. FIG. 22 is a cross-section of the distal end portion of the treatment-instrument main unit 4B cut along a plane including the point of the hook portion 1012 and the center axis Ax.

The cap 11B is made from a resin material, such ac polytetrafluoroethylene (PTFE) or tetrafluoroethylene perfluoroalkyl vinyl ether copolymer (PFA) having electric insulation. This cap 11B includes an engaging portion 131 and an exposed portion 132 as illustrated in FIG. 20 to FIG. 22.

The engaging portion 131 has a substantially cylindrical shape coaxial with the center axis Ax. In the present embodiment, an outer diameter dimension of the engaging portion 131 is a little larger than an outer diameter dimension of the end portion of the sheath BB on the distal end side Ar1. Moreover, an inner diameter dimension of the engaging portion 131 is a little larger than an outer dimension of the hook portion 1012 in the first direction Ar3.

In this engaging portion 131, as illustrated in FIG. 20, a pair of notch portions 1311 that pierce through from an outer peripheral surface to an inner peripheral surface are arranged. These pair of the notch portions 1311 respectively have a U-shape. Inside the U-shape of the notch portion 1311, a claw portion 1312 that extends from the proximal end side Ar2 to the distal end side Ar1, and that is capable of elastic deformation in a direction of diameter of the engaging portion 131 from a base portion on the proximal end side Ar2 as a base point is formed. The pair of the notch portions 1311 (pair of the claw portions 1312) are arrange at rotationally symmetric positions by 180° about the center axis Ax.

The exposed position 132 has a substantially cylindrical shape surrounding the center axis Ax, and is arranged at a distal end of the engaging portion 131 on the distal end side Ar1. In this exposed portion 132, an end portion on the proximal end side Ar2 connected to the engaging portion 131 has a larger outer diameter dimension than the engaging portion 131. That is, on an outer peripheral surface of the cap 11B, a step portion 133 (FIG. 20 to FIG. 22) is arranged between the exposed portion 132 and the engaging portion 131. Hereinafter, for convenience of explanation, a surface abutting on the step portion 133 on the outer peripheral surface of the exposed portion 132 will be denoted as protruded surface 1321.

Moreover, the outer peripheral surface of the exposed portion 132 is formed by the protruded surface 1321, a slant surface 1322, and a distal-end outer-peripheral surface 1323 continuously arranged from the proximal end side Ar2 toward the distal end side Ar1 as illustrated in FIG. 20 to FIG. 22.

The protruded surface 1321 is a surface that linearly extends from a position abutting on the step portion 133 toward the distal end side Ar1 along the center axis Ax.

The slant surface 1322 is a surface in which a diameter dimension gradually decreases from the position abutting on the protruded surface 1221 toward the distal end side Ar1.

The distal-end outer-peripheral surface 1323 is a surface linearly extends from a position abutting on the slant surface 1222 toward the distal end side Ar1 along the center axis Ax.

In the present embodiment, an inner diameter dimension of the exposed portion 132 at the end portion on the distal end side Ar1 is smaller than the outer dimension of the hook portion 1012 in the first direction Ar3.

An outer diameter dimension of a distal end portion 130 (FIG. 20 to FIG. 22) having the distal-end outer-peripheral surface 1323 is smaller than an outer diameter dimension of the engaging portion 131 corresponding to a proximal end portion. Moreover, the outer diameter dimension of the distal end portion 130 is smaller than the outer dimension of the hook portion 1012 in the first direction Ar3. The distal end portion 130 is made thin, and thereby acquires a function of "providing" a field of view for an operator that uses the treatment-instrument main unit 4B or the like.

In the cap 11B explained above, a slit 134 (FIG. 20 to FIG. 22) that is linearly cut along the center axis from the proximal end of the exposed portion 132 toward the distal end side Ar1 is arranged on one end side in the first direction Ar3. This slit 134 corresponds to a first slit.

A width dimension of this slit 134 is a little larger an the outer dimension of the hook portion 1012 in the second direction Ar4.

An outer diameter dimension and an inner diameter dimension of the end portion of the sheath 8B on the distal end side Ar1 gradually decrease toward the distal end side Ar1 as illustrated in FIG. 20 or FIG. 22. In the present embodiment, the inner diameter dimension of the end portion on the distal end side Ar1 is smaller than the outer dimension of the hook portion 1012 in the first direction Ar3. In the end portion on the distal end side Ar1, a slit 831 (FIG. 20) that pierces through from the outer peripheral surface to the inner peripheral surface, and that extends from the distal end of the sheath 8B toward the proximal end side Ar2 to avoid interference with the hook portion 1012 when performing step S2 is arranged. Moreover, in the end portion on the distal end side Ar1, a pair of engagement opening portions (not illustrated) that pierce through from the outer peripheral surface to the inner peripheral surface, and with which a pair of claw portions 1312 are engaged are arranged.

In a manufacturing method of the treatment instrument 2B according to the present embodiment, step S3 is different from the manufacturing method (FIG. 8) of the treatment instrument 2 explained in the embodiment described above.

At step S3 according to the present embodiment, an operator inserts the end effector 101 into the inside of the cap 11B from the proximal end side Ar2 of the cap 11B. Because the cap 11B is made from a relatively flexible material, such as PTFE or PFA, the operator makes the hook portion 1012 protrudes out from the distal end side Ar1 of the cap 11B by moving the cap 11B toward the proximal end side Ar2 while deforming the cap 11B. Moreover, the operator inserts the end portion of the sheath 8B on the distal end side Ar1 into the inside of the engaging portion 131. The cap 11B is attached to the sheath 8B as the claw portions 1312 engage with the engagement opening portions (not illustrated) arranged in the sheath 8B. That is, the cap 11B is attached to the sheath 8B by the snap-fit mechanism.

At step S4, in a state in which the tube TU is attached, the distal end of the tube TU is positioned on the outer peripheral surface of the engaging portion 131 as illustrated in FIG. 21 or FIG. 22. In the present embodiment, a diameter dimension at the protruded surface 1321 is substantially the same as an outer diameter dimension of the tube TU at the distal end as illustrated in FIG. 22. Moreover, the diameter dimension at the protruded surface 1321 may be equal to or smaller than the outer diameter dimension of the tube TU at the distal end, or may be equal to or larger than the outer diameter dimension of the tube TU at the distal end.

As described above, the tube TU is arranged at a position enabling to cover both the outer peripheral surface of the sheath 8B and the outer peripheral surface of the cap 11B, straddling a boundary between the sheath 8B and the cap 11B. Moreover, in the sheath 8B and the cap 11B, a portion corresponding to the engaging portion 131 is an overlap area that overlaps in a radial direction. The tube TU covers the overlap area.

Also when the treatment-instrument main unit 4B according to the present embodiment explained above is adopted, effects similar to those of the embodiment described above are obtained.

Next, another exemplary embodiment will be explained.

In the following explanation, identical reference symbols are assigned to components identical to those of the embodiment described above with respect to FIGS. 1-16, and detailed explanation thereof will be omitted or simplified.

The present embodiment differs from the embodiment described above in a shape of the sheath 8.

Hereinafter, for convenience of explanation, the sheath 8 according to the present embodiment will be denoted as sheath 8C.

The sheath 8C and the cap 11 correspond to a cover member.

Figure 23:
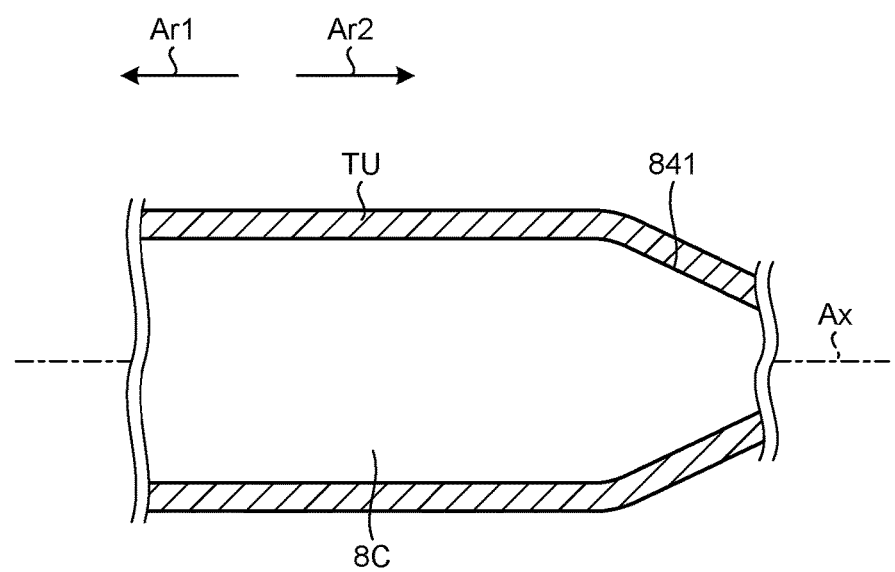
FIG. 23 is a diagram illustrating a shape of a sheath according to an exemplary embodiment.

FIG. 23 is a diagram illustrating a shape of the sheath 8C according to the present embodiment.

In the sheath 8C, a slant surface 841, an outer diameter dimension, of which gradually decreases toward the proximal end side Ar2 is arranged between an end portion on the distal end side Ar1 connected to the cap 11 and an end portion on the proximal end side Ar2 connected to the holding portion 9 as illustrated in FIG. 23.

According to the present embodiment explained above, besides effects similar to those of the embodiment described above, a following effect is obtained.

In the present embodiment, because the slant surface 841 is arranged in the sheath 8C, displacement of the tube TU toward the distal end side relative to the sheath 8C can be prevented.

Next, another exemplary embodiment will be explained.

In the following explanation, identical reference symbols are assigned to components identical to those of the embodiments described above, and detailed explanation thereof will be omitted or simplified.

The present embodiment differs from the embodiment described above with respect to FIGS. 1-16 in a structure of the distal end portion of the treatment-instrument main unit 4 (structure of the sheath 8 and the cap 11).

Hereinafter, for convenience of explanation, the treatment instrument 2 according to the present embodiment will be denoted as treatment instrument 2D. Moreover, the treatment-instrument main unit 4 according to the present embodiment will be denoted as treatment-instrument main unit 4D. Furthermore, the sheath 8 according to the present embodiment will be denoted as sheath 8D. Moreover, the cap 11 according to the present embodiment will be denoted as cap 11D.

The sheath 8D and the cap 11D correspond to a cover member. Moreover, the cap 11D corresponds to a tubular portion.

Figure 24:
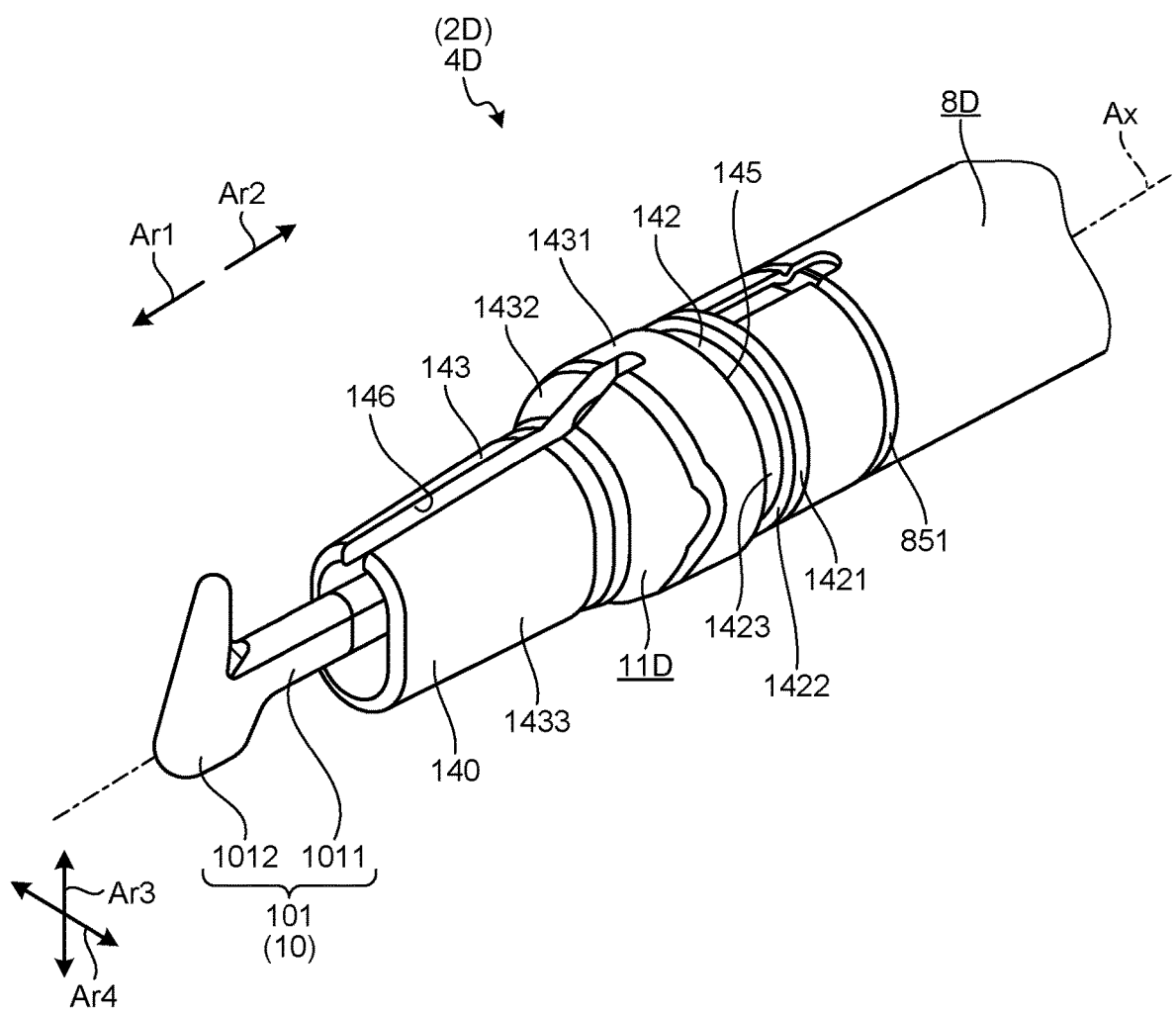
FIG. 24 is a diagram illustrating a distal end portion of a treatment-instrument main unit according to an embodiment.
Figure 25:
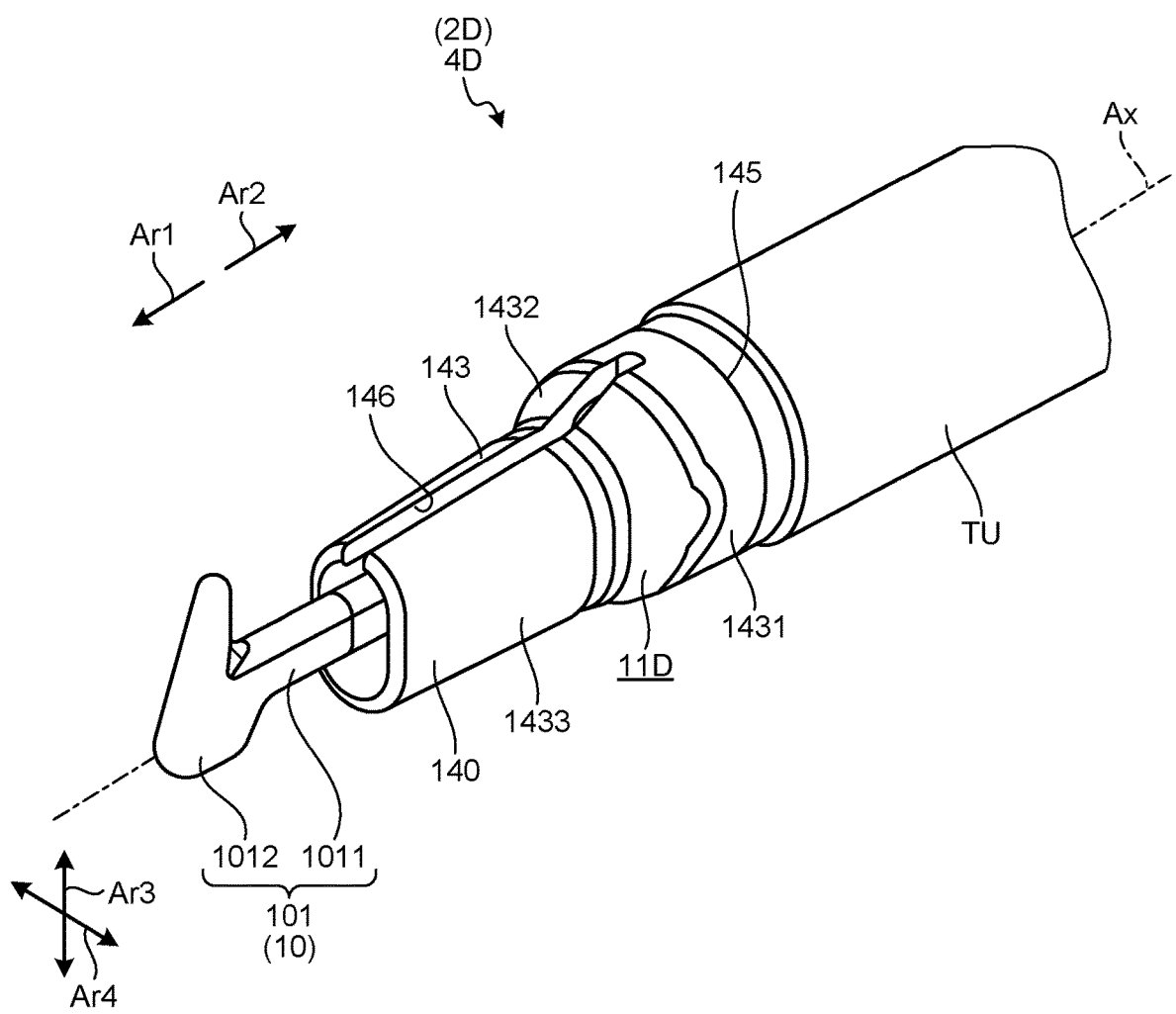
FIG. 25 is a diagram illustrating the distal end portion of the treatment-instrument main unit according to the exemplary embodiment.
Figure 26:
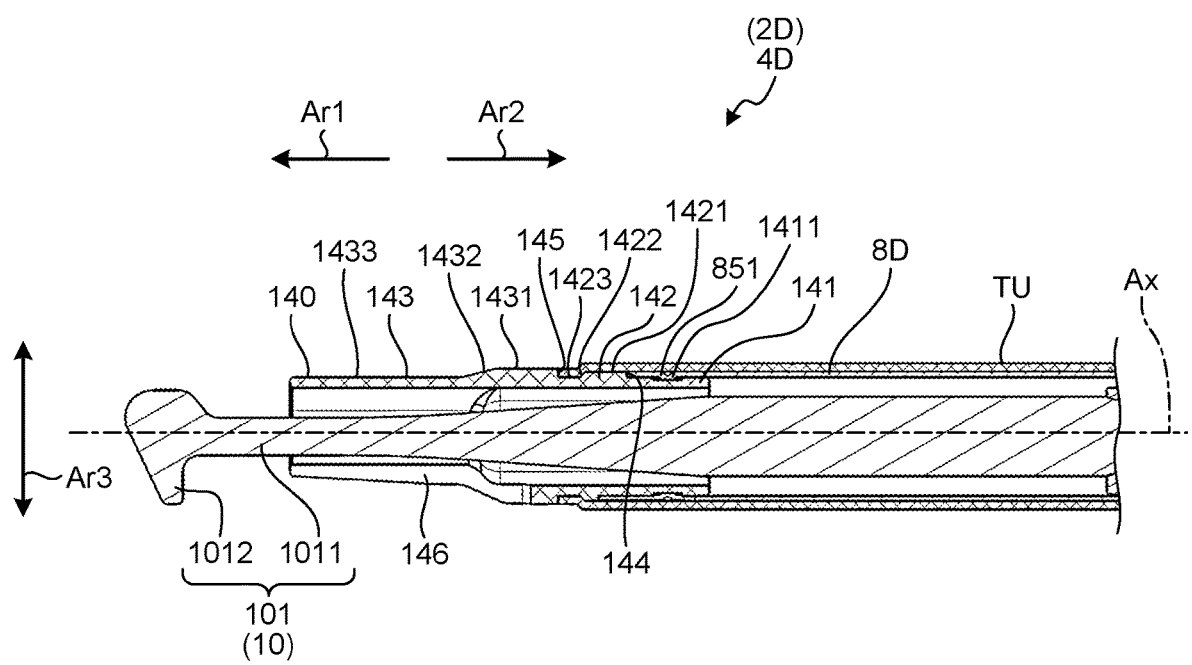
FIG. 26 is a diagram illustrating the distal end portion of the treatment-instrument main unit according to the exemplary embodiment.

FIG. 24 to FIG. 26 are diagrams illustrating an end portion of the treatment-instrument main unit 4D according to the present embodiment. Specifically, FIG. 24 and FIG. 25 are diagrams illustrating an external view of the distal end portion of the treatment-instrument main unit 4D. While FIG. 24 illustrates a state in which the tube TU is removed, FIG. 25 illustrates a state in which the tube TU is attached. FIG. 26 is a cross-section of the distal end portion of the treatment-instrument main unit 4D cut along a plane including the point of the hook portion 1012 and e center axis Ax.

The cap 11D is made from a resin material, such as PEEK having electric insulation. This cap 11D includes an engaging portion 141 (FIG. 26), a connecting portion 142 (FIG. 24, FIG. 26) and an exposed portion 143 as illustrated in FIG. 24 to FIG. 26.

The engaging portion 141 has a substantially cylindrical shape coaxial with the center axis Ax. In the present embodiment, an outer diameter dimension of the engaging portion 141 is a little smaller than an inner diameter dimension of the sheath 8D. Moreover, respective inner diameter dimensions of the engaging portion 141 and e connecting portion 142 are a little larger than an outer dimension of the hook portion 1012 in the first direction Ar3.

On an outer peripheral surface of this engaging portion 141, a ring-shaped concave portion 1411 that his a ring shape about the center axis Ax, and that is recessed toward the center axis Ax is arranged as illustrated in FIG. 26.

The connecting portion 142 is a portion that connects an end portion of the engaging portion 141 on the distal end side Ar1 and an end portion of the exposed portion 143 on the proximal end side Art, and has a substantially cylindrical shape surrounding the center axis Ax. In this connecting portion 142, the end portion on the proximal end side Art connected to the engaging portion 141 has an outer diameter dimension larger than the engaging portion 141. That is, on an outer peripheral surface of the cap 110, a first step portion 144 (FIG. 26) is arranged between the connecting portion 142 and the engaging portion 141.

Moreover, an outer peripheral surface of the connecting portion 142 is formed by a proximal-end outer-peripheral surface 1421, a first slant surface 1422, and a first distal-end outer-peripheral surface 1423 continuously arranged from the proximal end side Ar2 toward the distal end side Ar1 as illustrated in FIG. 26.

The proximal-end outer-peripheral surface 1421 is a surface that linearly extends from a position abutting on the first step portion 144 toward the distal end side Ar1 along the center axis Ax.

The first slant surface 1422 is a surface in which a diameter dimension gradually decreases from the position abutting on the proximal-end outer-peripheral surface 1421 toward the distal end side Ar1.

The first distal-end outer-peripheral surface 1423 is a surface that linearly extends from a position abutting on the first slant surface 1422 toward the distal end side Ar1 along the center axis Ax.

The exposed portion 143 has a substantially cylindrical shape surrounding the center axis Ax, and is arranged at an end portion of the connecting portion 142 on the distal end side Ar1. In this exposed portion 143, an end portion on the proximal end side Ar2 connected to the connecting portion 142 has a larger outer diameter dimension than the first distal-end outer-peripheral surface 1423. That is, on the outer peripheral surface of the cap 11D, a second step portion 145 (FIG. 25, FIG. 26) is arranged between the exposed portion 143 and the connecting portion 142. Hereinafter, for convenience of explanation, a surface abutting on the second step portion 145 on the outer peripheral surface of the exposed portion 143 will be denoted as protruded surface 1431.

Moreover, an outer peripheral surface of the exposed portion 143 is formed by the protruded surface 1431, a second slant surface 1432, and a second distal-end outer-peripheral surface 1433 continuously arranged from the proximal end side Art toward the distal end side Ar1 as illustrated in FIG. 24 to FIG. 26.

The protruded surface 1431 is a surface that linearly extends from a position abutting on the second step portion 145 toward the distal end side Ar1 along the center axis Ax.

The second slant surface 1432 is a surface in which a diameter dimension gradually decreases from the position abutting on the protruded surface 1431 toward the distal end side Ar1.

The second distal-end outer-peripheral surface 1433 is a surface that linearly extends from a position abutting on the second slant surface 1432 toward the distal end side Ar1 along the center axis Ax.

In the present embodiment, an inner diameter dimension of the end portion on the distal end side Ar1 is smaller than the outer dimension of the hook portion 1012 in the first direction Ar3.

An outer diameter dimension at a distal end portion 140 having the second distal-end outer-peripheral surface 1433 (FIG. 24 to FIG. 26) is smaller than an outer diameter dimension at the engaging portion 141 corresponding to a proximal end portion. Moreover, an outer diameter dimension at the distal end portion 140 is smaller than an outer dimension of the hook portion 1012 in the first direction Ar3. The distal end portion 140 is made thin, and thereby acquires a function of providing a field of view for an operator that uses the treatment-instrument main unit 4D or the like.

In the cap 11D explained above, a slit 146 (FIG. 24 to FIG. 26) that is cut linearly along the center axis Ax from a distal end of the exposed portion 143 toward the proximal end side Ar2 is arranged on an end side in the first direction Ar3. This slit 146 corresponds to the first slit.

A width dimension of this slit 146 is a little larger than the outer dimension of the hook portion 1012 in the second direction Ar4.

At an end portion of the sheath 8D on the distal end side Ar1, unlike the sheath 8 explained in the embodiment described above, the pair of engagement opening portions 811 and the positioning notch portion 812 are not provided.

In a manufacturing method of the treatment instrument 2D according to the present embodiment, step S3 is different from the manufacturing method (FIG. 8) of the treatment instrument 2 explained in the embodiment described above.

At step S3 according to the present embodiment, an operator inserts the end effector 101 into the inside of the cap 11D from the proximal end side Ar2 of the cap 11D. The operator makes the hook portion 1012 protrude out from the distal end side Ar1 of the cap 11D by moving the cap 11D toward the proximal end side Ar2 while putting the point of the hook portion 1012 in the slit 146. Moreover, the operator moves the cap 11D to the proximal end side Ar2, and inserts the engaging portion 141 into the inside of the sheath 8D. The operator crimps the sheath 8D to be deformed in a direction of shrinking the diameter of the sheath 8D by using a not illustrated jig, and fits a deformed portion 851 (FIG. 24, FIG. 26) in the ring-shaped concave portion 1411. Thus, the cap 11D is attached to the sheath 8D.

At step S4, in a state in which the tube TU is attached, the distal end of the tube TU is positioned between the protruded surface 1431 and the first slant surface 1422, that is, on the first distal-end outer-peripheral surface 1423 as illustrated in FIG. 26. In the present embodiment, a diameter dimension at the protruded surface 1431 is substantially the same as an outer diameter dimension of the tube TU at the distal end as illustrated in FIG. 26. Moreover, the diameter dimension at the protruded surface 1431 may be equal to or smaller than the outer diameter dimension of the tube TU at the distal end, or may be equal to or larger than the outer diameter dimension of the tube TU at the distal end.

As described above, the tube TU is arranged at a position enabling to cover both the outer peripheral surface of the sheath 8D and the outer peripheral surface of the cap 11D, straddling a boundary between the sheath 8D and the cap 11D. Moreover, in the sheath 8D and the cap 11D, a portion corresponding to the engaging portion 141 and the first slant surface 1422 is an overlap area that overlaps in a radial direction. The tube TU covers the overlap area.

Also when the treatment-instrument main unit 4D according to the present embodiment explained above is adopted, effects similar to those of the embodiment described above are obtained.

Next, another exemplary embodiment will be explained.

In the following explanation, identical reference symbols are assigned to components identical to those of the embodiments described above, and detailed explanation thereof will be omitted or simplified.

The present embodiment differs from the embodiment described above with respect to FIG. 1-16 in a structure of the distal end portion of the treatment-instrument main unit 4 (structure of the sheath 8 and the cap 11).

Hereinafter, for convenience of explanation, the treatment instrument 2 according to the present embodiment will be denoted as treatment instrument 2E. Moreover, the treatment-instrument main unit 4 according to the present embodiment will be denoted as treatment-instrument main unit 4E. Furthermore, the cap 11 according to the present embodiment will be denoted as cap 11E. Because the sheath 8 according to the present embodiment is same as the sheath 8D explained in the embodiment described above with respect to FIGS. 24-26, it will be denoted as sheath 8D.

The sheath 8D and the cap 11E correspond to a cover member. Moreover, the cap 11E corresponds to a tubular portion.

Figure 27:
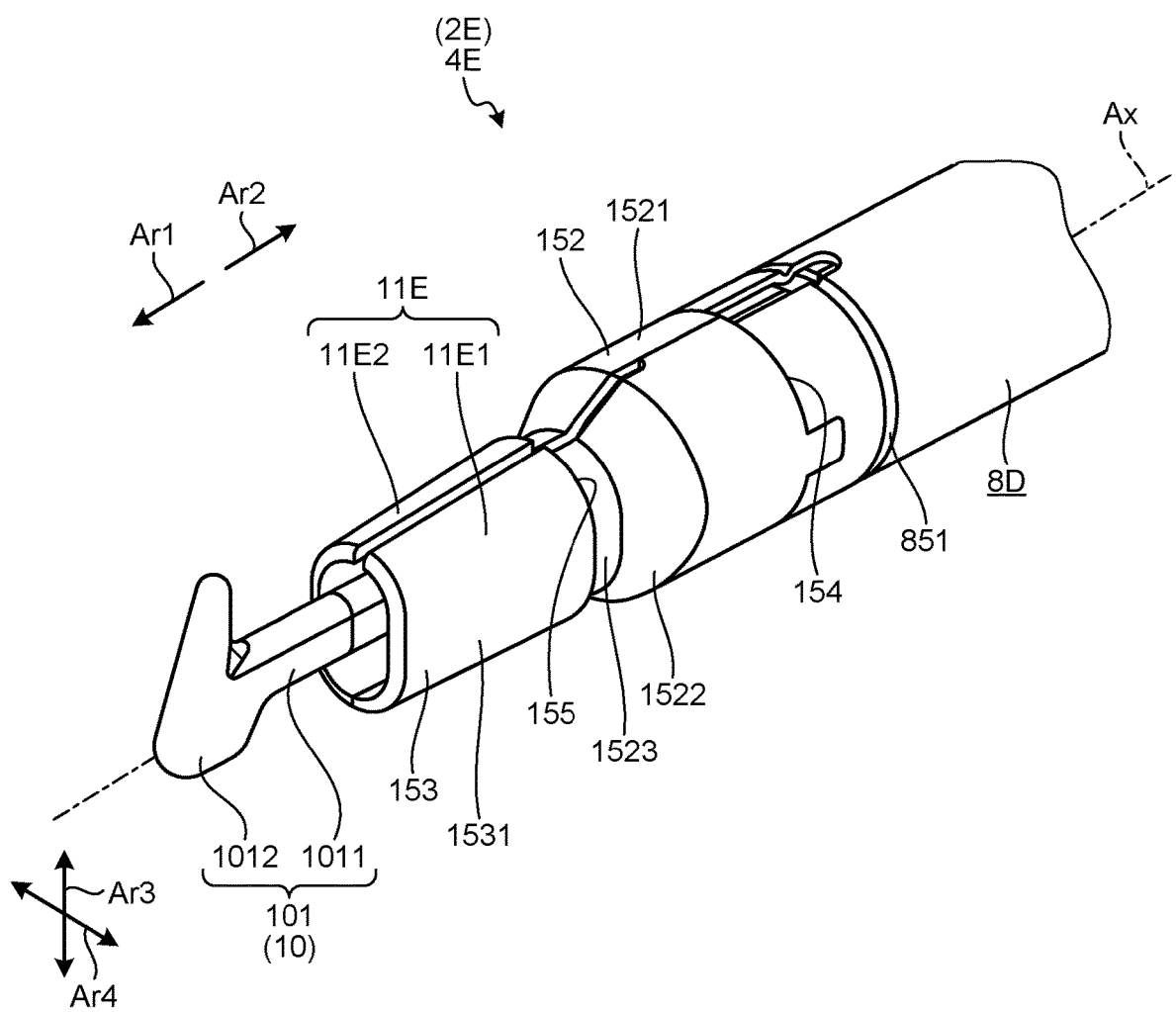
FIG. 27 is a diagram illustrating a distal end portion of a treatment-instrument main unit according to an exemplary embodiment.
Figure 28:
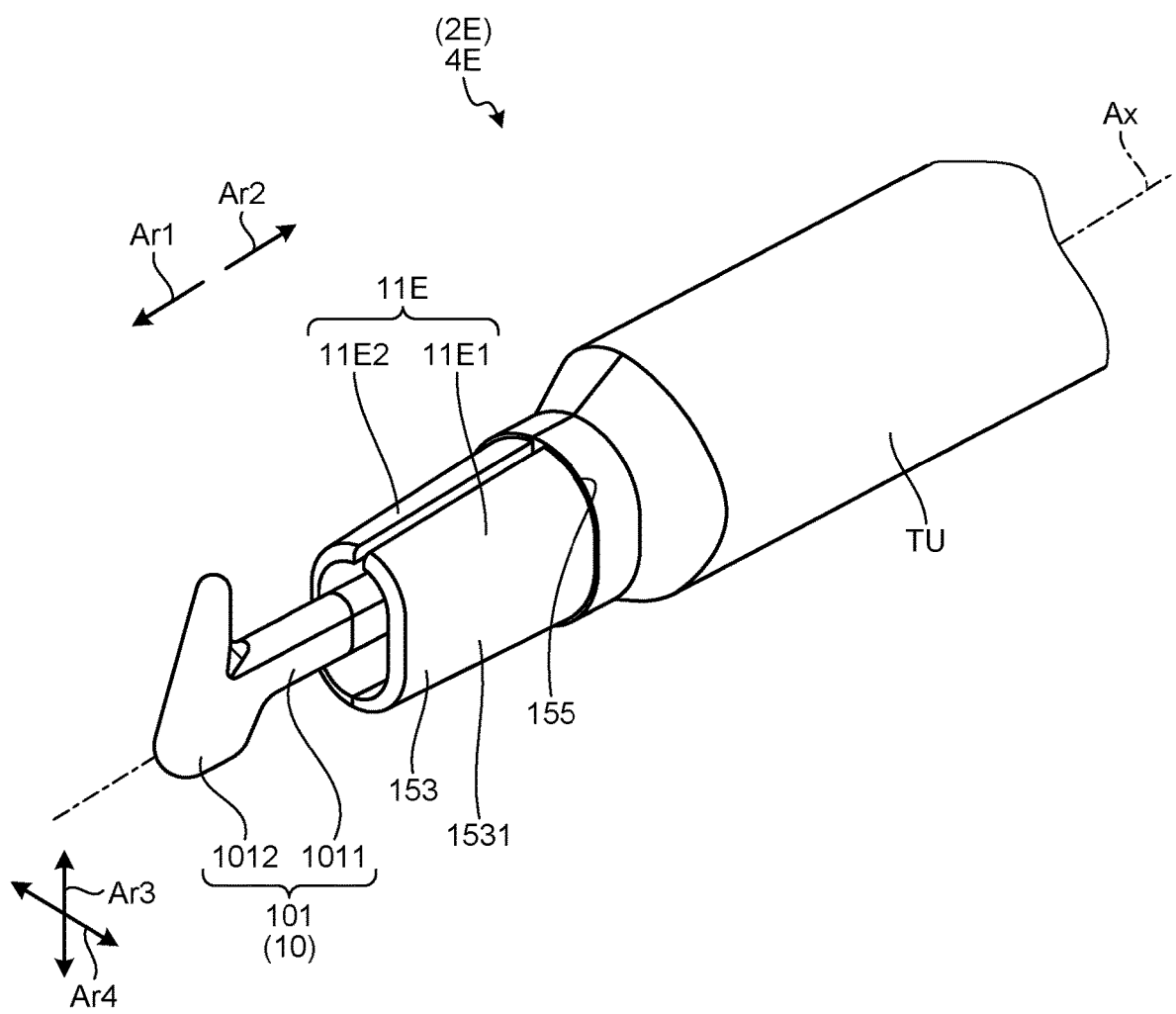
FIG. 28 is a diagram illustrating the distal end portion of the treatment-instrument main unit according to the exemplary embodiment.
Figure 29:
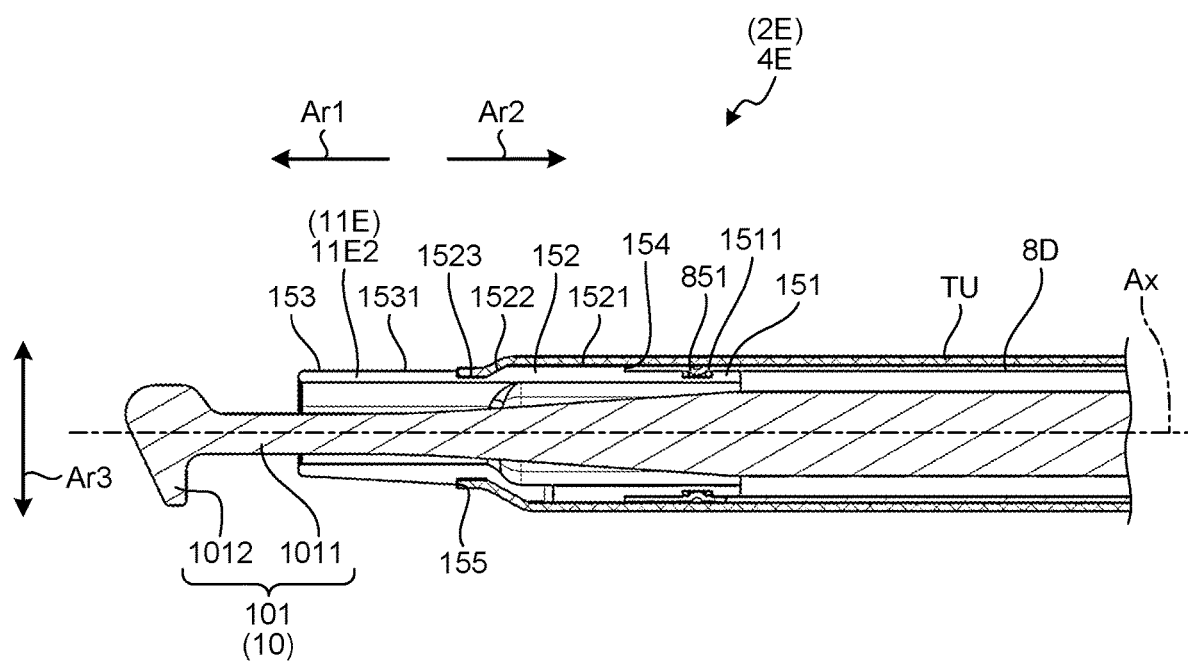
FIG. 29 is a diagram illustrating the distal end portion of the treatment-instrument main unit according to the exemplary embodiment.

FIG. 27 to FIG. 29 are diagrams illustrating a distal end portion of the treatment-instrument main unit 4E according to the present embodiment. Specifically, FIG. 27 and FIG. 28 are diagrams illustrating an external view of the distal end portion of the treatment-instrument main unit 4E. While FIG. 27 illustrates a state in which the tube TU is removed, FIG. 28 illustrates a state in which the tube TU is attached. FIG. 29 is a cross-section of the distal end portion of treatment-instrument main unit 4E cut along a plane including the point of the hook portion 1012 and the center axis Ax.

The cap 11E is made from a resin material, such as PEEK, having electric insulation. This cap 11E is, as illustrated in FIG. 27 or FIG. 28, divided into two pieces, a first and a second caps 11E1 and 11E2, at a plane including the point of the hook portion 1012 and the center axis Ax as a boundary. These first and the second caps 11E1, 11E2 have shapes symmetric about the plane. In a state in which the first and the second caps 11E1 and 11E2 are assembled, the cap 11E includes an engaging portion 151 (FIG. 29), a connecting portion 152 (FIG. 27, FIG. 29), and a distal end portion 153 as illustrated in FIG. 27 to FIG. 29.

The engaging portion 151 has a substantially cylindrical shape coaxial with the center axis Ax. In the present embodiment, an outer diameter dimension of the engaging portion 151 is a little smaller than an inner diameter dimension of the sheath 80.

On an outer peripheral surface of this engaging portion 151, as illustrated in FIG. 29, a ring-shaped concave portion 1511 that has a ring shape about the center axis and that is recessed toward the center axis Ax is arranged.

The connecting portion 152 is a portion connecting an end portion of the engaging portion 151 on the distal end side Ar1 and an end portion of the distal end portion 153 on the proximal end side Ar2, and has a substantially cylindrical shape surrounding the center axis Ax. In the connecting portion 152, the end portion on the proximal end side Ar2 connected to the engaging portion 151 has an outer diameter larger than the engaging portion 151. That is, on an outer peripheral surface of the cap 11E, a first step portion 154 (FIG. 27, FIG. 29) is arranged between the connecting portion 152 and the engaging portion 151.

Moreover, the outer peripheral surface of the connecting portion 152 is formed by a proximal-end outer-peripheral surface 1521, a slant surface 1522, and a distal-end outer-peripheral surface 1523 continuously arranged from the proximal end side Ar2 toward the distal end side Ar1 as illustrated in. FIG. 27 to FIG. 29.

The proximal-end outer-peripheral surface 1521 is a surface that linearly extends toward the distal end side Ar1 along the center axis Ax from a position abutting on the first step portion 154.

The slant surface 1522 is a surface in which a diameter dimension decreases toward the distal end side Ar1 from a position abutting on the proximal-end outer-peripheral surface 1521.

The distal-end outer-peripheral surface 1523 is a surface that linearly extends toward the distal end side Ar1 along the center axis Ax from a position abutting on e slant surface 1522.

The distal end portion 153 has a substantially cylindrical shape surrounding the center axis Ax, and is arranged at an end portion of connecting portion 152 on the distal end side Ar1. This distal end portion 153 has a larger outer diameter dimension than the distal-end outer-peripheral surface 1523. That is, on the outer peripheral surface of the cap 11E, a second step portion 155 (FIG. 27, FIG. 29) is arranged between the distal end portion 153 and the connecting portion 152. Hereinafter, for convenience of explanation, an outer peripheral surface of the distal end portion 153 will be denoted as protruded surface 1531.

The protruded surface 1531 is a surface that substantially linearly extends toward the distal end side Ar1 along the center axis Ax from a position abutting on the second step portion 155.

An outer diameter dimension at the distal end portion 153 is smaller than an outer diameter dimension of the engaging portion 151 corresponding to a proximal end portion. Moreover, an outer diameter dimension at the distal end portion 153 is smaller than an outer dimension of the hook portion 1012 in the first direction Ar3. The distal end portion 153 is made thin, and thereby acquires a function of providing a field of view for an operator that uses the treatment-instrument main unit 4E or the like.

In a manufacturing method of the treatment instrument 2E according to the present embodiment, step S3 is different from the manufacturing method (FIG. 8) of the treatment instrument 2 explained in the embodiment described above.

At step S3 according to the present embodiment, an operator assembles the first and the second caps 11E1 and 11E2 in a state in which the pillar portion 1011 is positioned between the first and the second caps 11E1 and 11E2. In this state, the hook portion 1012 protrudes out from the distal end side Ar1 of the cap 11E in which the first and second caps 11E1 and 11E2 are assembled. The operator then moves the cap 11E toward the proximal end side Ar2, to insert the engaging portion 151 into the inside of the sheath 8D. The operator crimps the sheath 8D to be deformed in a direction of shrinking the diameter of the sheath 8D by using a not illustrated jig, and fits a deformed portion 851 (FIG. 27, FIG. 29) in the ring-shaped concave portion 1511. Thus, the cap 11E is attached to the sheath 8D.

At step S4, in a state in which the tube TU is attached, the distal end of the tube TU is positioned between the protruded surface 1531 and the slant surface 1522, that is, on the distal-end outer-peripheral surface 1523 as illustrated in FIG. 29. In the present embodiment, a diameter dimension at the protruded surface 1531 is substantially the same as an outer diameter dimension of the tube TU at the distal end as illustrated in FIG. 29. Moreover, the diameter dimension at the protruded surface 1531 may be equal to or smaller than the outer diameter dimension of the tube TU at the distal end, or may be equal to or larger than the outer diameter dimension of the tube TU at the distal end.

As described above, the tube TU is arranged at a position enabling to cover both the outer peripheral surface of the sheath 8D and the outer peripheral surface of the cap 11E, straddling a boundary between the sheath 8D and the cap 11E. Moreover, in the sheath 8D and the cap 11E, a portion corresponding to the engaging portion 151 and the slant surface 1522 is an overlap area that overlaps in a radial direction. The tube TU covers the overlap area.

Also when the treatment-instrument main unit 4E according to the present embodiment explained above is adopted, effects similar to those of the embodiment described above are obtained.

Moreover, the cap 11E is constituted of two pieces of parts, the first and the second caps 11E1 and 11E2. Therefore, at step S3, a process of inserting the end effector 101 into the inside of the cap 11E is not necessary, and assembly of the cap 11E can be easily performed.

Next, another exemplary embodiment will be explained.

In the following explanation, identical reference symbols are assigned to components identical to those of the embodiments described above, and detailed explanation thereof will be omitted or simplified.

The present embodiment differs from the embodiment described above with respect to FIGS. 1-16 in a structure of the distal end portion of the treatment-instrument main unit 4 (structure of the sheath 8 and the cap 11).

Hereinafter, for convenience of explanation, the treatment instrument 2 according to the present embodiment will be denoted as treatment instrument 2F, Moreover, the treatment-instrument main unit 4 according to the present embodiment will be denoted as treatment-instrument main unit 4F. The sheath 8 according to the present embodiment will be denoted as sheath 8F. Furthermore, the cap 11 according to the present embodiment will be denoted as cap 11F.

The sheath 8F and the cap 11F correspond to a cover member. Moreover, the cap 11F corresponds to a tubular portion.

Figure 30:
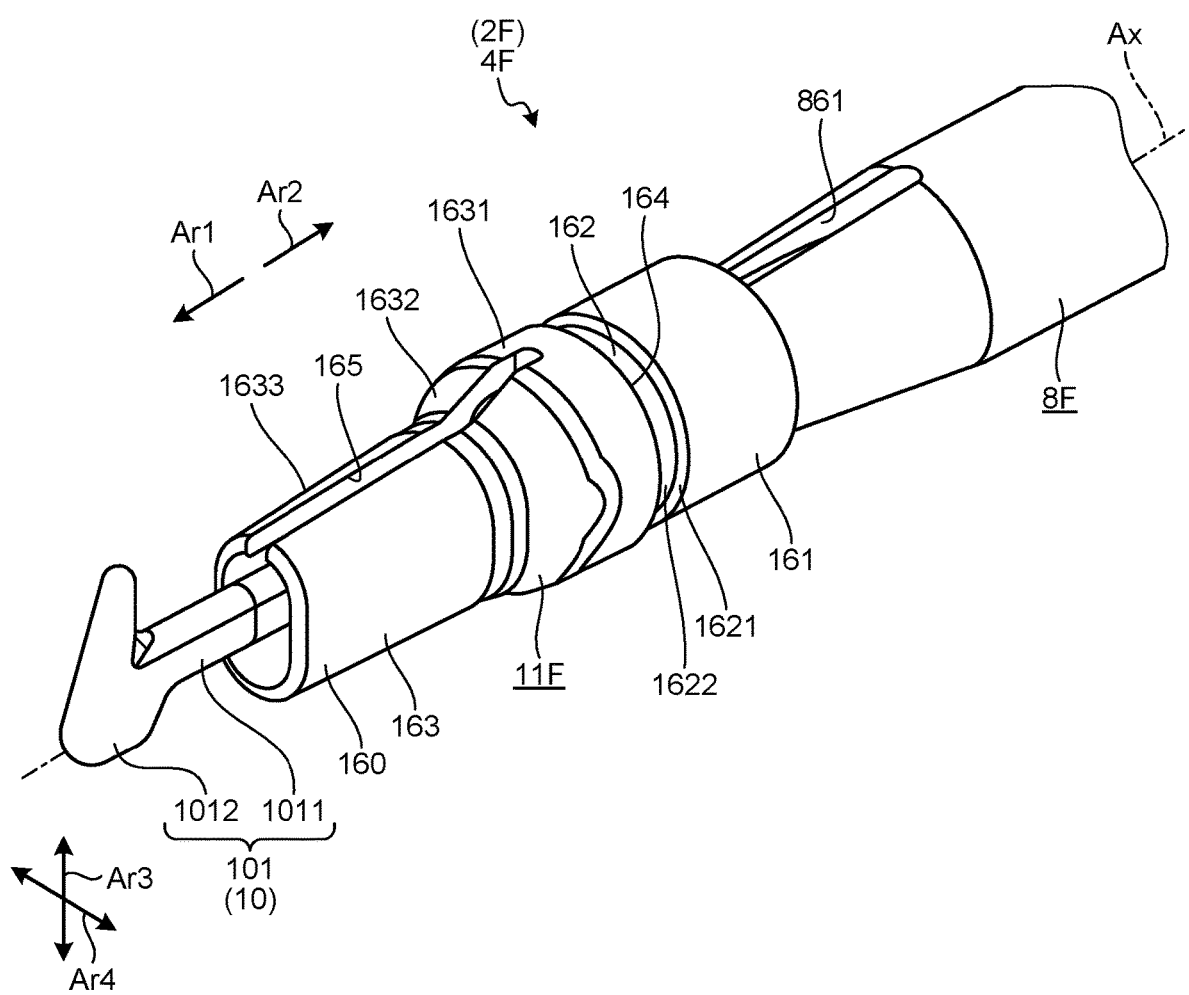
FIG. 30 is a diagram illustrating a distal end portion of a treatment-instrument main unit according to an exemplary embodiment.
Figure 31:
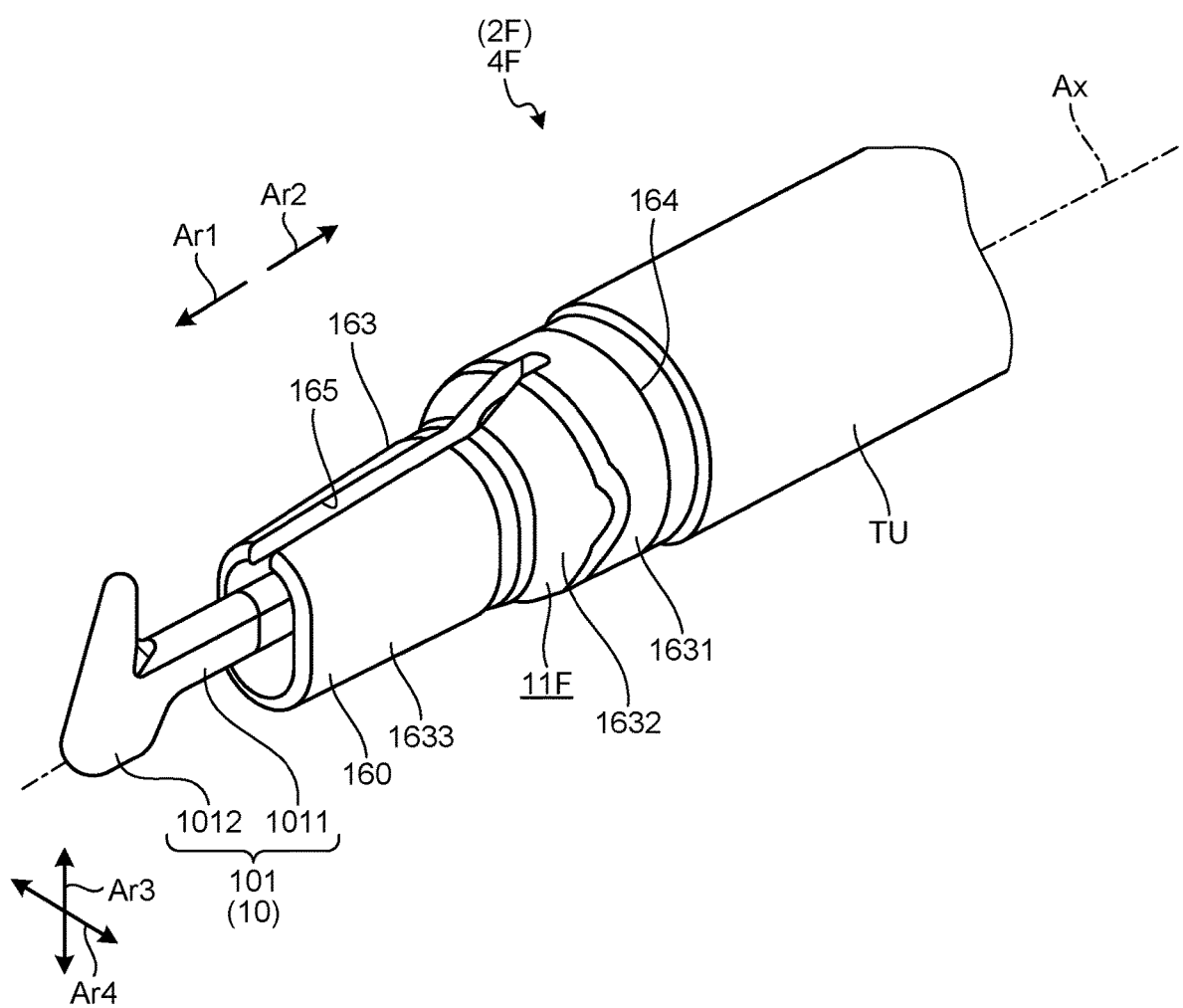
FIG. 31 is a diagram illustrating the distal end portion of the treatment-instrument main unit according to the exemplary embodiment.
Figure 32:
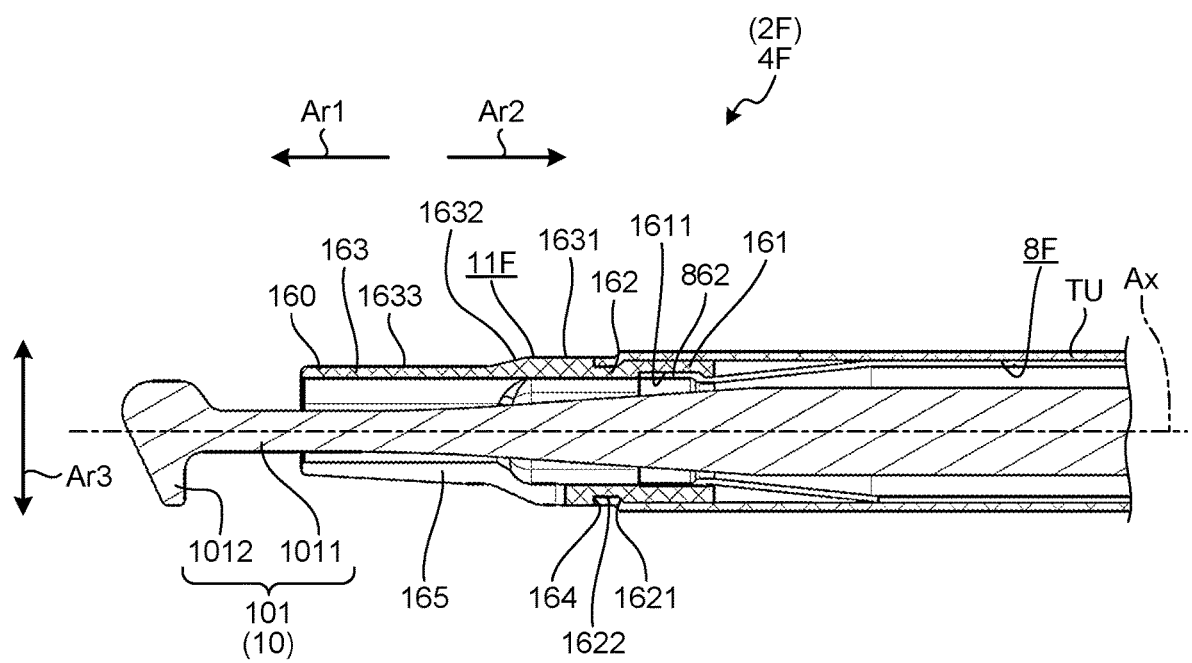
FIG. 32 is a diagram illustrating the distal end portion of the treatment-instrument main unit according to the exemplary embodiment.

FIG. 30 to FIG. 32 are diagrams illustrating a distal end portion of the treatment-instrument main unit 4F according to the present embodiment. Specifically, FIG. 30 and FIG. 31 are diagrams illustrating an external view of the distal end portion of the treatment-instrument main unit 4F. While FIG. 30 illustrates a state in which the tube TU is removed, FIG. 31 illustrates a state in which the tube TU is attached. FIG. 32 is a cross-section of the distal end portion of the treatment-instrument main unit 4F cut along a plane including the point of the hook portion 1012 and the center axis Ax.

The cap 11F is made from a resin material, such as PEEK, having electric insulation. This cap 11E includes an engaging portion 161, a connecting portion 162, and an exposed portion 163 as illustrated in FIG. 30 to FIG. 32.

The engaging portion 161 has a substantially a cylindrical shape coaxial with the center axis Ax. In the present embodiment, an outer diameter dimension of the engaging portion 161 is a little larger than an outer diameter dimension of an end portion of the sheath 8F on the distal end side Ar1. Moreover, an inner diameter dimension of the engaging portion 161 is a little larger than an outer dimension of the hook portion 1012 in the first direction Ar3.

On an inner peripheral surface of this engaging portion 161, as illustrated in FIG. 32, a ring-shaped concave portion 1611 that has a ring shape about the center axis and that is recessed toward a direction away from the center axis Ax is arranged.

The connecting portion 162 is a portion connecting an end portion of the engaging portion 161 on the distal end side Ar1 and an end portion of the exposed portion 163 on the proximal end side Ar2, and has a substantially cylindrical shape surrounding the center axis Ax. In the present embodiment, an inner diameter dimension of the connecting portion 162 and an inner diameter dimension of the engaging portion 161 are substantially the same.

Moreover, the outer peripheral surface of the connecting portion 162 is formed by a first slant surface 1621 and a first distal-end outer-peripheral surface 1622 continuously arranged from the proximal end side Ar2 toward the distal end side Ar1 as illustrated in FIG. 30 or FIG. 32.

The first slant surface 1621 is a surface in which a diameter dimension decreases toward the distal end side Ar1 from a position abutting on the engaging portion 161.

The first distal-end outer-peripheral surface 1622 is a surface that linearly extends toward the distal end side Ar1 along the center axis Ax from a position abutting on the first slant surface 1621.

The exposed portion 163 has a substantially cylindrical shape surrounding the center axis Ax, and is arranged at an end portion of the connecting portion 162 on the distal end side Ar1. In this exposed portion 163, an end portion on the proximal end side Ar2 connected to the connecting portion 162 has a larger outer diameter dimension than the first proximal-end outer-peripheral surface 1622. That is, on the outer peripheral surface of the cap 11F, a step portion 164 (FIG. 30, FIG. 32) is arranged between the exposed portion 163 and the connecting portion 162. Hereinafter, for convenience of explanation, a surface abutting on the step portion 164 on the outer peripheral surface of the exposed portion 163 will be denoted as protruded surface 1631.

Moreover, an outer peripheral surface of the exposed portion 163 is formed by the protruded surface 1631, a second slant surface 1632, and a second distal-end outer-peripheral surface 1633 continuously arranged from the proximal end side Ar2 toward the distal end side Ar1 as illustrated in FIG. 30 to FIG. 32.

The protruded surface 1631 is a surface that linearly extends from a position abutting on the step portion 164 toward the distal end side Ar1 along the center axis Ax.

The second slant surface 1632 is a surface in which a diameter dimension gradually decreases from the position abutting on the protruded surface 1631 toward the distal end side Ar1.

The second distal-end outer-peripheral surface 1633 is a surface that substantially linearly extends from a position abutting on the second slant surface 1632 toward the distal end side Ar1 along the center axis Ax.

In the present embodiment, an inner diameter dimension of an end portion on the distal end side Ar1 in the exposed portion 163 is smaller than the outer dimension of the hook portion 1012 in the first direction Ar3.

An outer diameter dimension at a distal end portion 160 (FIG. 30 to FIG. 32) having the second distal-end outer-peripheral surface 1633 is smaller than an outer diameter dimension of the engaging portion 161 corresponding to a proximal end portion. Moreover, an outer diameter dimension at the distal end portion 160 is smaller than an outer dimension of the hook portion 1012 in the first direction Ar3. The distal end portion 160 is made thin, and thereby acquires a function of providing a field of view for an operator that uses the treatment-instrument main unit 4 or the like.

In the cap 11F explained above, a slit 165 (FIG. 30 to FIG. 32) that is cut linearly along the center axis from a distal end of the exposed portion 163 toward the proximal end side Art is arranged on an end side in the first direction Ar3. This slit 165 corresponds to the first slit.

A width dimension of this slit 165 is a little larger an the outer dimension of the hook portion 1012 in the second direction Ar4.

At an end portion of the sheath 8F on the distal end side Ar1, an outer diameter dimension and an inner diameter dimension gradually decrease toward the distal end side Ar1 as illustrated in FIG. 30 or FIG. 32. In the present embodiment, the inner diameter dimension of the end portion on the distal end side Ar1 is smaller than the outer dimension of the hook portion 1012 in the first direction Ar3. In the end portion on the distal end side Ar1, a slit 861 (FIG. 30) that pierces through from an outer peripheral surface to an inner peripheral surface and extends toward the proximal end side Ar2 from a distal end of the sheath 8F, to avoid interference with the hook portion 1012 when step S2 is performed is arranged.

In a manufacturing method of the treatment instrument 2F according to the present embodiment, step S3 is different from the manufacturing method (FIG. 8) of the treatment instrument 2 explained in the embodiment described above.

At step S3 according to the present embodiment, an operator inserts the end effector 101 into the inside of the cap 11F from the proximal end side Ar2 of the cap 11F. The operator makes the hook portion 1012 protrude out from the distal end side Ar1 of the cap 11F by moving the cap 11F toward the proximal end side Ar2 while putting the point of the hook portion 1012 in the slit 165. Moreover, the operator moves the cap 11F to the proximal end side Ar2, and inserts an end portion of the sheath 8F on the distal end side Ar1 into the inside of the engaging portion 161. The operator crimps the sheath 8F to be deformed in a direction of expanding the diameter of the sheath 8F by using a not illustrated jig, and fits a deformed portion 862 (FIG. 32) in the ring-shaped concave portion 1611. Thus, the cap 11F is attached to the sheath 8F.

At step S4, in a state in which the tube TU is attached, the distal end of the tube TU is positioned between the protruded surface 1631 and the first slant surface 1621, that is, on the first distal-end outer-peripheral surface 1622 as illustrated in FIG. 32. In the present embodiment, a diameter dimension at the protruded surface 1631 is substantially the same as an outer diameter dimension of the tube TU at the distal end as illustrated in FIG. 32. Moreover, the diameter dimension at the protruded surface 1631 may be equal to or smaller than the outer diameter dimension of the tube TU at the distal end, or may be equal to or larger than the outer diameter dimension of the tube TU at the distal end.

As described above, the tube TU is arranged at a position enabling to cover both the outer peripheral surface of the sheath 8F and the outer peripheral surface of the cap 11F, straddling a boundary between the sheath 8F and the cap 11F. Moreover, in the sheath 8F and the cap 11F, a portion corresponding to the engaging portion 161 and the first slant surface 1621 is an overlap area that overlaps in a radial direction. The tube TU covers the overlap area.

Also when the treatment-instrument main unit 4F according to the present embodiment explained above is adopted, effects similar to those of the embodiment described above are obtained.

Next, another exemplary embodiment will be explained.

In the following explanation, identical reference symbols are assigned to components identical to those of the embodiments described above, and detailed explanation thereof will be omitted or simplified.

The present embodiment differs from the embodiment described above with respect to FIGS. 1-16 in a structure of the distal end portion of the treatment-instrument main unit 4 (structure of the sheath 8 and the cap 11).

Hereinafter, for convenience of explanation, the treatment instrument 2 according to the present embodiment will be denoted as treatment instrument 2G. Moreover, the treatment-instrument main unit 4 according to the present embodiment will be denoted as treatment-instrument main unit 4G. Furthermore, the cap 11 according to the present embodiment will be denoted as cap 11G. Because the sheath 8 according to the present embodiment is substantially the same as the sheath 8A explained in the embodiment described above with respect to FIGS. 17-19, it will be denoted as sheath 8A.

The sheath 8A and the cap 11G correspond to a cover member. Moreover, the cap 11G corresponds to a tubular portion.

Figure 33:
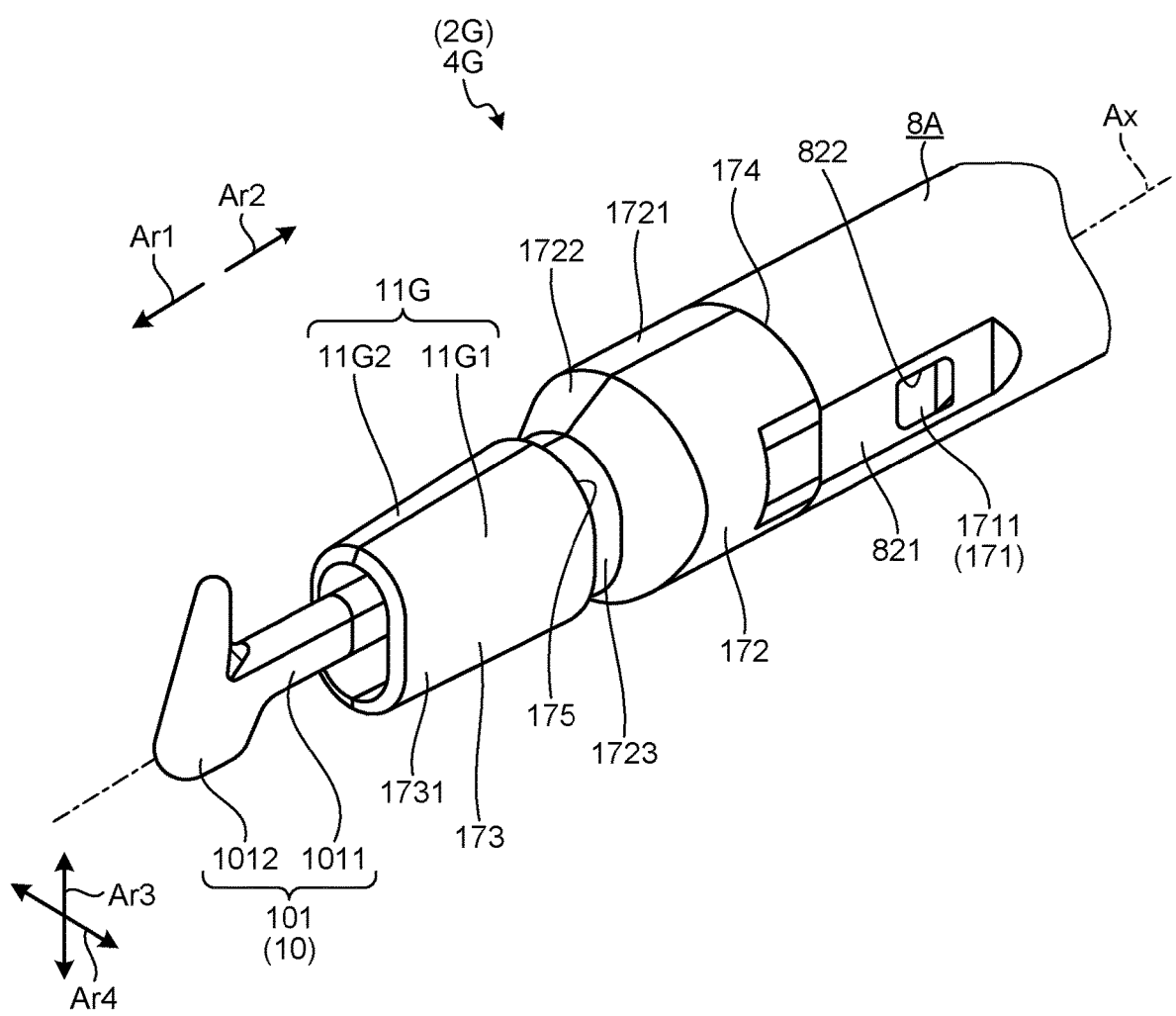
FIG. 33 is a diagram illustrating a distal end portion of a treatment-instrument main unit according to an exemplary embodiment.
Figure 34:
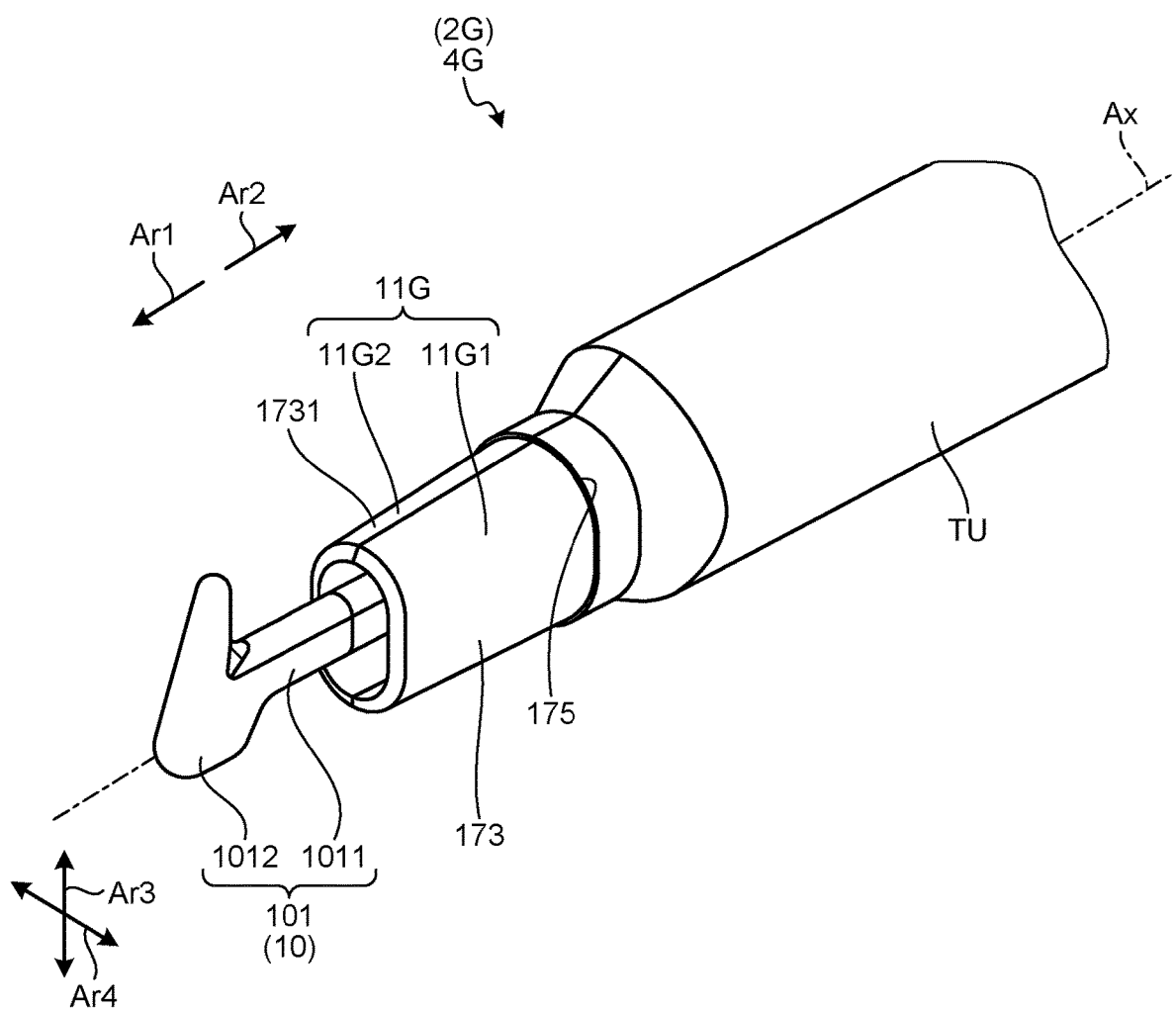
FIG. 34 is a diagram illustrating the distal end portion of the treatment-instrument main unit according to the exemplary embodiment.
Figure 35:
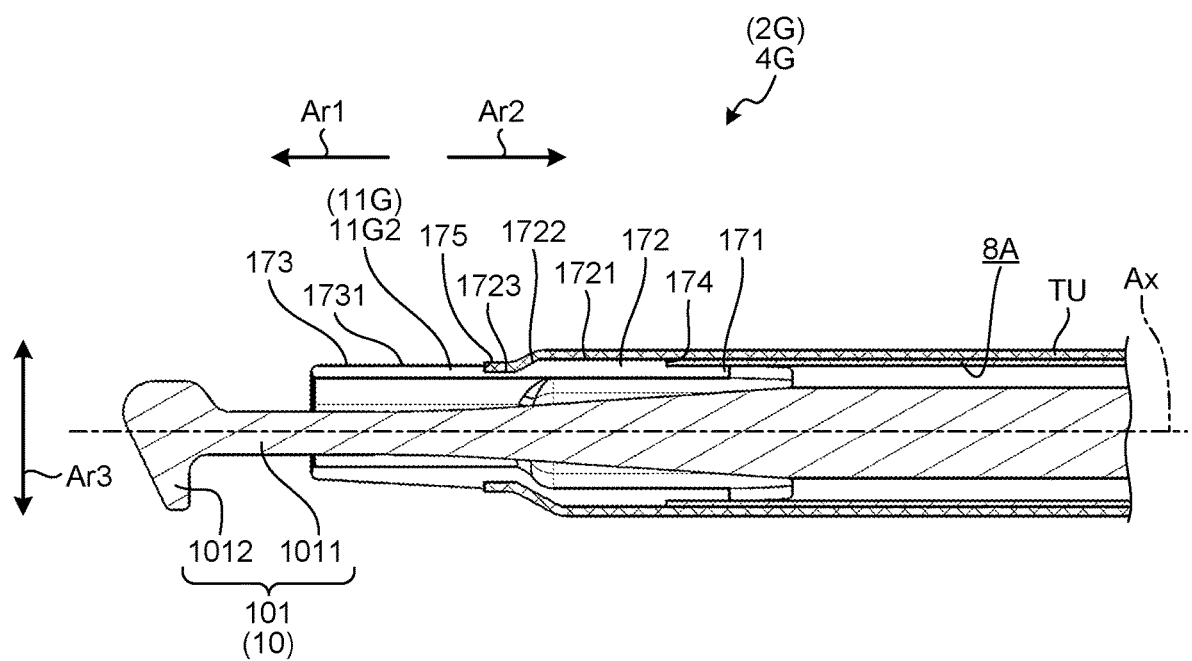
FIG. 35 is a diagram illustrating the distal end portion of the treatment-instrument main unit according to the exemplary embodiment.
Figure 36:
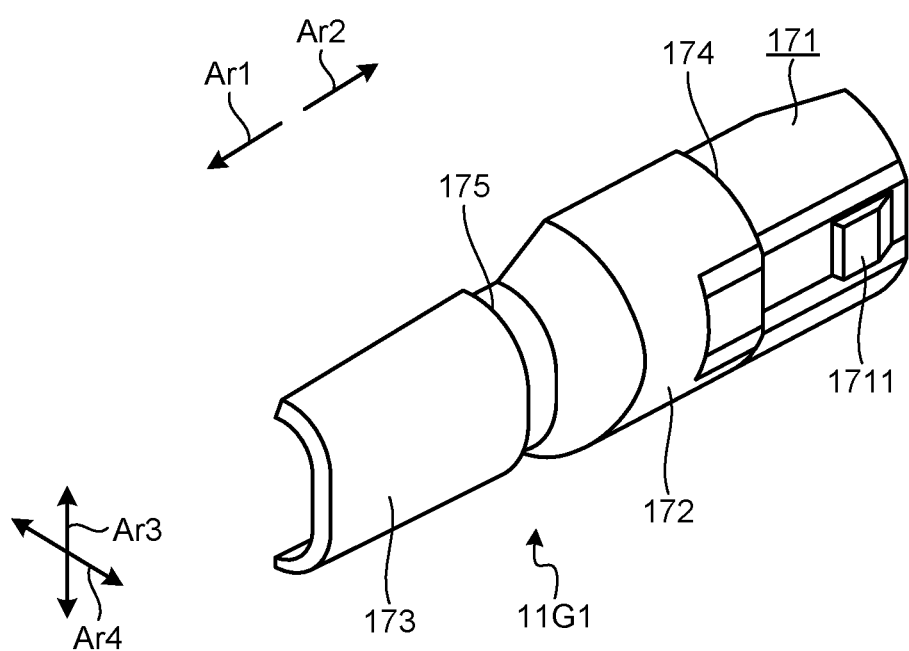
FIG. 36 is a diagram illustrating a first cap.

FIG. 33 to FIG. 35 are diagrams illustrating a distal end portion of the treatment-instrument main unit 4G according to the present embodiment. FIG. 36 is a diagram illustrating a first cap 11G1. Specifically, FIG. 33 and FIG. 34 are diagrams illustrating an external view of the distal end portion of the treatment-instrument main unit 4G. While FIG. 33 illustrates a state in which the tube TU is removed, FIG. 34 illustrates a state in which the tube TU is attached. FIG. 35 is a cross-section of the distal end portion of the treatment-instrument main unit 4G cut along a plane including the point of the hook portion 1012 and the center axis Ax.

The cap 11G is made from a resin material, such as PEEK, having electric insulation. This cap 11G is, as illustrated in FIG. 33, FIG. 34, or FIG. 36, divided into two pieces, a first and a second caps 11G1 and 11G2, at a plane including the point of the hook portion 1012 and the center axis Ax as a boundary. These first and the second caps 11G1, 11G2 have shapes symmetric about the plane. In a state in which the first and the second caps 11G1 and 11G2 are assembled, the cap 11G includes an engaging portion 171 (FIG. 33, FIG. 35, FIG. 36), a connecting portion 172 (FIG. 33, FIG. 35, FIG. 36), and a distal end portion 173 as illustrated in FIG. 33 to FIG. 36.

The engaging portion 171 has a substantially cylindrical shape coaxial with the center axis Ax. In the present embodiment, an outer diameter dimension of the engaging portion 171 is a little smaller than an inner diameter dimension of the sheath 8A.

On an outer peripheral surface of this engaging portion 171, a pair of convex portions 1711 respectively protruding in a direction away from the center axis Ax are arranged as illustrated in FIG. 33 or FIG. 36. These pair of the convex portions 1711 are arranged respectively in the first and the second caps 11G1 and 11G2, and is positioned at rotationally symmetric positions by 180° about the center axis Ax.

The connecting portion 172 is a portion connecting an end portion in the engaging portion 171 on the distal end side Ar1 and an end portion in the distal end portion 153 on the proximal end side Ar2, and has a substantially cylindrical shape surrounding the center axis Ax. In the connecting portion 172, an end portion on the proximal end side Ar2 connected to the engaging portion 171 has an outer diameter dimension larger than the engaging portion 171. That is, on an outer peripheral surface of the cap 11G, a first step portion 174 (FIG. 35, FIG. 36) is arranged between the connecting portion. 172 and the engaging portion 171.

Moreover, the outer peripheral surface of the connecting portion 172 is formed by a proximal-end outer-peripheral surface 1721, a slant surface 1722, and a distal-end outer-peripheral surface 1723 continuously arranged from the proximal end side Ar2 toward the distal end side Ar1 as illustrated in FIG. 35 to FIG. 36.

The proximal-end outer-peripheral surface 1721 is a surface that linearly extends toward the distal end side Ar1 along the center axis from a position abutting on the first step portion 174.

The slant surface 1722 is a surface in which a diameter dimension decreases toward the distal end side Ar1 from a position abutting on the proximal-end outer-peripheral surface 1721.

The distal-end outer-peripheral surface 1723 is a surface that linearly extends toward the distal end side Ar1 along the center axis Ax from a position abutting on the slant surface 1722.

The distal end portion 173 has a substantially cylindrical shape surrounding the center axis Ax, and is arranged at an end portion of the connecting portion 172 on the distal end side Ar1. This distal end portion 173 has a larger outer diameter dimension than the distal-end outer-peripheral surface 1723. That is, on the outer peripheral surface of the cap 11G, a second step portion 175 (FIG. 33, FIG. 35, FIG. 36) is arranged between the distal end portion 173 and the connecting portion 172. Hereinafter, for convenience of explanation, the outer peripheral surface of the distal end portion 173 will be denoted as protruded surface 1731.

The protruded surface 1731 is a surface that substantially linearly extends toward the distal end side Ar1 along the center axis Ax from a position abutting on the second step portion 175.

An outer diameter dimension at the distal end portion 173 is smaller than an outer diameter dimension of the engaging portion 171 corresponding to a proximal end portion. Moreover, the outer diameter dimension at the distal end portion 173 is smaller than the outer dimension of the hook portion 1012 in the first direction Ar3. The distal end portion 173 is made thin, and thereby acquires a function of providing a field of view for an operator that uses the treatment-instrument main unit 4G, or the like.

In a manufacturing method of the treatment instrument 2G according to the present embodiment, step S3 is different from the manufacturing method (FIG. 8) of the treatment instrument 2 explained in the embodiment described above.

At step S3 according to the present embodiment, an operator assembles the first and the second caps 11G1 and 11G2 in a state in which the pillar portion 1011 is positioned between the first and the second caps 11G1 and 11G2. In this state, the hook portion 1012 protrudes out from the distal end side Ar1 of the cap 11G in which the first and the second caps 11G1 and 11G2 are assembled. The operator then moves the cap 11G toward the proximal end side Ar2, to insert the engaging portion 171 into the inside of the sheath 8A. The cap 11G is attached to the sheath 8A as the convex portion 1711 is engaged with the engagement opening portion 822. That is, the cap 11G is attached to the sheath 8A by a snap-fit mechanism.

At step S4, in a state in which the tube TU is attached, the distal end of the tube TU is positioned between the protruded surface 1731 and the slant surface 1722, that is, on the distal-end outer-peripheral surface 1723 as illustrated in FIG. 35. In the present embodiment, a diameter dimension at the protruded surface 1731 is substantially the same as an outer diameter dimension of the tube TU at the distal end as illustrated in FIG. 35. Moreover, the diameter dimension at the protruded surface 1731 may be equal to or smaller than the outer diameter dimension of the tube TU at the distal end, or may be equal to or larger than the outer diameter dimension of the tube TU at the distal end.

As described above, the tube TU is arranged at a position enabling to cover both the outer peripheral surface of the sheath 8A and the outer peripheral surface of the cap 11G, straddling a boundary between the sheath 8A and the cap 11F. Moreover, in the sheath BF and the cap 11G, a portion corresponding to the engaging portion 171 and the slant surface 1722 is an overlap area that overlaps in a radial direction. The tube TU covers the overlap area.

Also when the treatment-instrument main unit 4G according to the present embodiment explained above is adopted, effects similar to those of the embodiments described above with respect to FIGS. 1-29 are obtained.

Next, another exemplary embodiment will be explained.

In the following explanation, identical reference symbols are assigned to components identical to those of the embodiments described above, and detailed explanation thereof will be omitted or simplified.

The present embodiment differs from the embodiment described above with respect to FIGS. 1-16 in a structure of the distal end portion of the treatment-instrument main unit 4 (structure of the sheath 8 and the cap 11).

Hereinafter, for convenience of explanation, the treatment instrument 2 according to the present embodiment will be denoted as treatment instrument 2H, Moreover, the treatment-instrument main unit 4 according to the present embodiment will be denoted as treatment-instrument main unit 4H. Furthermore, the cap 11 according to the present embodiment will be denoted as cap 11H. Because the sheath 8 according to the present embodiment is substantially the same as the sheath 8A explained in the embodiment described above with respect to FIGS. 17-19, it will be denoted as sheath 8A.

The sheath 8A and the cap 11H correspond to a cover member. Moreover, the cap 11H corresponds to a tubular portion.

Figure 37:
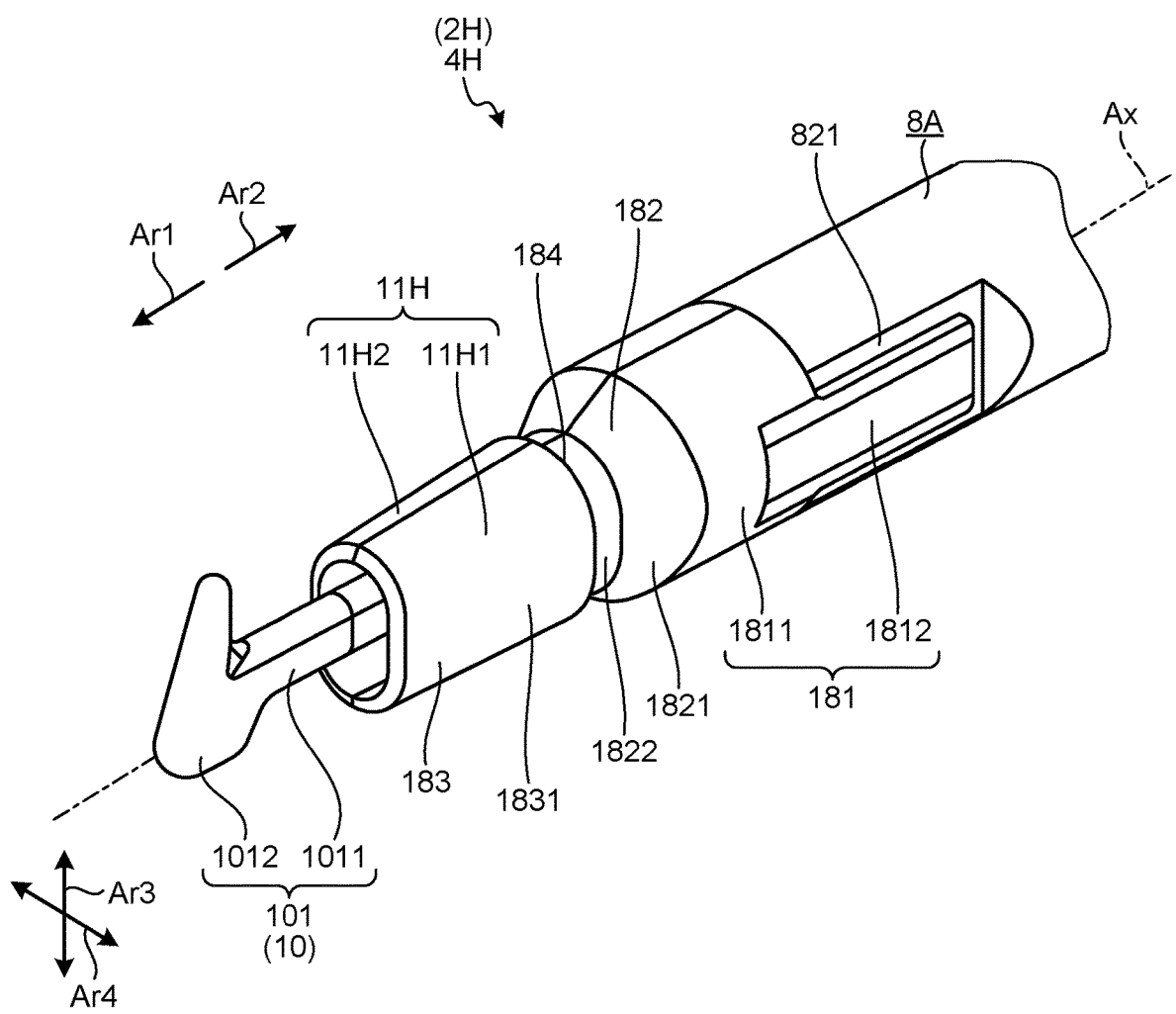
FIG. 37 is a diagram illustrating a distal end portion of a treatment-instrument main unit according to an exemplary embodiment.
Figure 38:
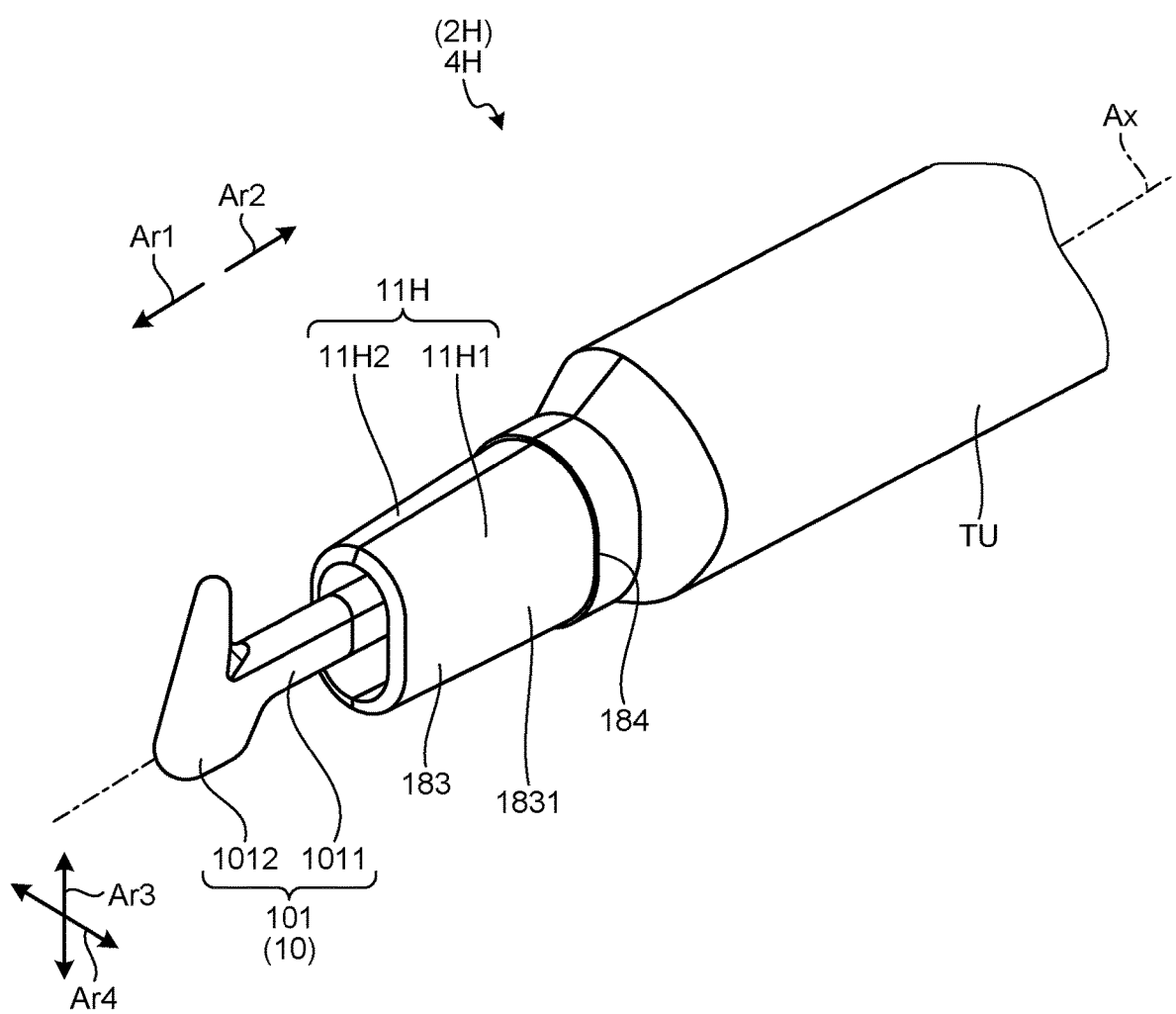
FIG. 38 is a diagram illustrating the distal end portion of the treatment-instrument main unit according to the exemplary embodiment.
Figure 39:
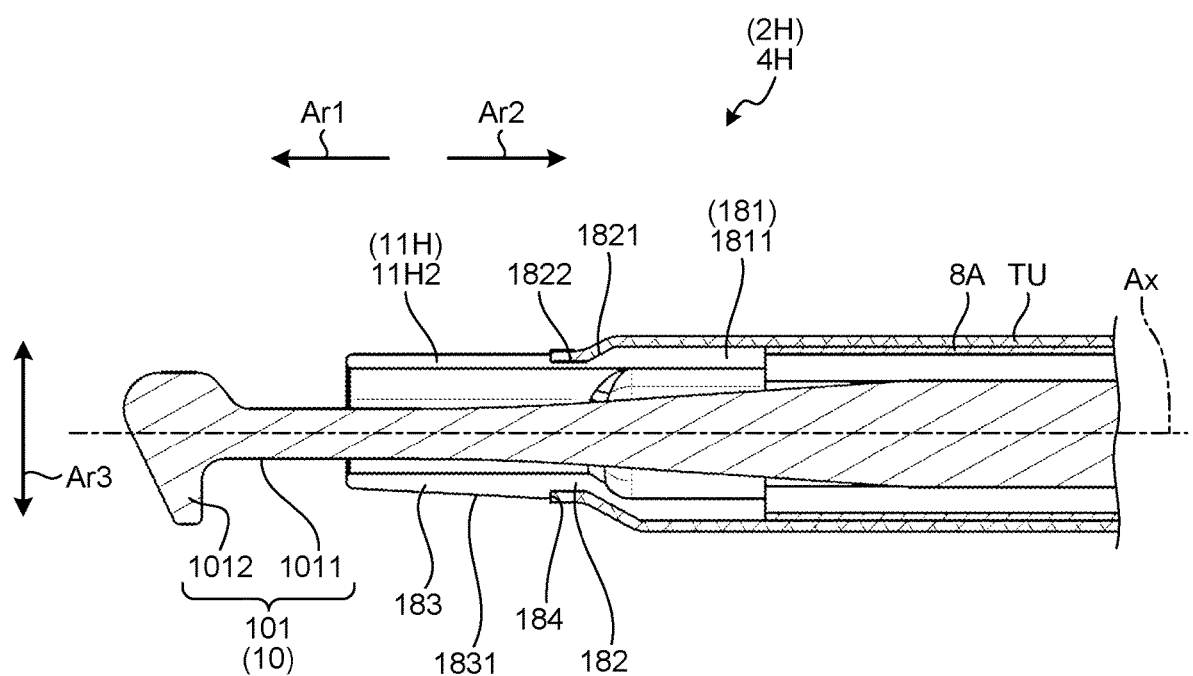
FIG. 39 is a diagram illustrating the distal end portion of the treatment-instrument main unit according to the exemplary embodiment.

FIG. 37 to FIG. 39 are diagrams illustrating a distal end portion of the treatment-instrument main unit 4H according to the present embodiment. Specifically, FIG. 37 and FIG. 38 are diagrams illustrating an external view of the distal end portion of the treatment-instrument main unit 4H. While FIG. 37 illustrates a state in which the tube TU is removed, FIG. 38 illustrates a state in which the tube TU is attached. FIG. 39 is a cross-section of the distal end portion of the treatment-instrument main unit 4H cut along a plane including the point of the hook portion 1012 and the center axis Ax.

The cap 11H is made from a resin material, such as PEEK, having electric insulation. This cap 11H is, as illustrated in FIG. 37 or FIG. 38, divided into two pieces, a first and a second caps 11H1 and 11H2, at a plane including the point of the hook portion 1012 and the center axis Ax as a boundary. These first and the second caps 11H1, 11H2 have shapes symmetric about the plane. In a state in which the first and the second caps 11H1 and 11H2 are assembled, the cap 11H includes an engaging portion 181 (FIG. 37, FIG. 39), a connecting portion 182 (FIG. 37, FIG. 39), and a distal end portion 183 as illustrated in FIG. 37 to FIG. 39.

The engaging portion 181 includes an engaging-portion main unit 1811 and a pair of arm portions 1812.

The engaging-portion main unit 1811 has a substantially cylindrical shape coaxial with the center axis Ax. In the present embodiment, an outer diameter dimension of the engaging-portion main unit 1811 is substantially the same as the outer diameter dimension of the sheath 8A.

The pair of the arm portions 1812 are arranged respectively in the first and the second caps 11H1 and 11H2, and are positioned at rotationally symmetric positions about the center axis Ax by 180°. More specifically, the pair of the arm portions 1812 oppose to each other from a proximal end of the engaging-portion main unit 1811 and protrude toward the proximal end side Ar2, and is capable of elastic deformation in a direction of becoming close to and apart from each other, from a proximal end on the distal end side Ar1 as a base point. A separation distance between surfaces opposing to each other in these in these pair of the arm portions 1812 is substantially the same as a separation distance between outer surfaces of the pair of the flat portions 821 in the sheath 8A. In these pair of the arm portions 1812, convex portions (not illustrated) are arranged respectively on surfaces opposing to each other on the proximal end side Ar2.

The connecting portion 182 is a portion connecting an end portion in the engaging portion 181 on the distal end side Ar1 and an end portion in the distal end portion 183 on the proximal end side Ar2, and has a substantially cylindrical shape surrounding the center axis Ax.

Moreover, the outer peripheral surface of the connecting portion 182 is formed by a slant surface 1821 and a distal-end outer-peripheral surface 1822 continuously arranged from the proximal end side Ar2 toward the distal end side Ar1 as illustrated in FIG. 37 to FIG. 39.

The slant surface 1821 is a surface in which a diameter dimension decreases toward the distal end side Ar1 from a position abutting on the engaging portion 181.

The distal-end outer-peripheral surface 1822 is a surface that linearly extends toward the distal end side Ar1 along the center axis Ax from a position abutting on the slant surface 1321.

The distal end portion 183 has a substantially cylindrical shape surrounding the center axis Ax, and is arranged at an end portion of the connecting portion 182 on the distal end side Ar1. This distal end portion 183 has a larger outer diameter dimension than the distal-end outer-peripheral surface 1822. That is, on the outer peripheral surface of the cap 11H, a step portion 184 (FIG. 37 to FIG. 39) is arranged between the distal end portion 183 and the connecting portion 182. Hereinafter, for convenience of explanation, the outer peripheral surface of the distal end portion 183 will be denoted as protruded surface 1831.

The protruded surface 1831 is a surface that substantially linearly extends toward the distal end side Ar1 along the center axis Ax from a position abutting on the step portion 184.

An outer diameter dimension at the distal end portion 183 is smaller than an outer diameter dimension at the engaging-portion main unit 1811 corresponding to a proximal end portion. Moreover, the outer diameter dimension at the distal end portion 183 is smaller than the outer dimension of the hook portion 1012 in the first direction Ar3. The distal end portion 183 is made thin, and thereby acquires a function of providing a field of view for an operator that uses the treatment-instrument main unit 4H, or the like.

In a manufacturing method of the treatment instrument 2H according to the present embodiment, step S3 is different from the manufacturing method (FIG. 8) of the treatment instrument 2 explained in the embodiment described above.

At step S9 according to the present embodiment, an operator assembles the first and the second caps 11H1 and 11H2 in a state in which the pillar portion 1011 and the sheath 8A are positioned between the first and the second caps 11H1 and 11H2, and engages respective convex portions (not illustrated) in the pair of the arm portions 1812 with the engagement opening portion 822. The cap 11H is attached to the sheath 8A as the tube TU is attached by step S4.

At step S4, in a state in which the tube TU is attached, the distal end of the tube TU is positioned between the protruded surface 1831 and the slant surface 1821, that is, on the distal-end outer-peripheral surface 1822 as illustrated in FIG. 38 or FIG. 39. In the present embodiment, a diameter dimension at the protruded surface 1831 is substantially the same as an outer diameter dimension of the tube TU at the distal end as illustrated in FIG. 39. Moreover, the diameter dimension at the protruded surface 1831 may be equal to or smaller than the outer diameter dimension of the tube TU at the distal end, or may be equal to or larger than the outer diameter dimension of the tube TU at the distal end.

As described above, the tube TU is arranged at a position enabling to cover both the outer peripheral surface of the sheath 8A and the outer peripheral surface of the cap 11H, straddling a boundary between the sheath 8A and the cap 11F. Moreover, in the sheath 8A and the cap 11H, a portion corresponding to the pair of the arm portions 1812 and the slant surface 1821 is an overlap area that overlaps in a radial direction. The tube TU covers the overlap area.

Also when the treatment-instrument main unit 4H according to the present embodiment explained above is adopted, effects similar to those of the embodiments described above with respect to FIGS. 1-29 are obtained.

Next, another exemplary embodiment will be explained.

In the following explanation, identical reference symbols are assigned to components identical to those of the embodiments described above, and detailed explanation thereof will be omitted or simplified.

The present embodiment differs from the embodiment described above with respect to FIGS. 1-16 in a structure of the distal end portion of the treatment-instrument main unit 4 (structure of the sheath 8 and the cap 11).

Hereinafter, for convenience of explanation, the treatment instrument 2 according to the present embodiment will be denoted as treatment instrument 2I. Moreover, the treatment-instrument main unit 4 according to the present embodiment will be denoted as treatment-instrument main unit 4I. Furthermore, the sheath 8 according to the present embodiment will be denoted as sheath 8I. Moreover, the cap 11 according to the present embodiment will be denoted as cap 11I.

The sheath 8I and the cap 11I correspond to a cover member. Moreover, the cap 11I corresponds to a tubular portion.

Figure 40:
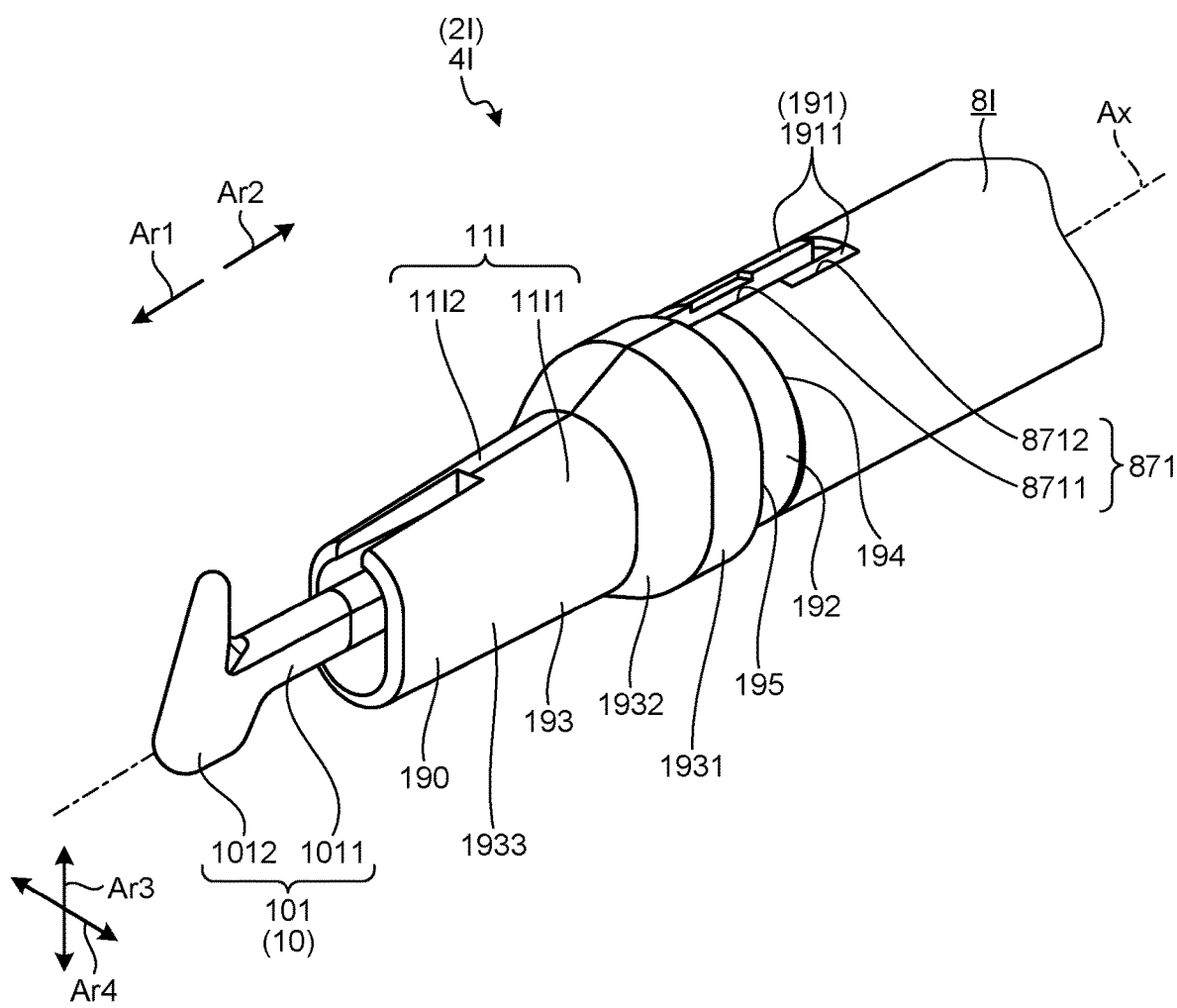
FIG. 40 is a diagram illustrating a distal end portion of a treatment-instrument main unit according to an exemplary embodiment.
Figure 41:
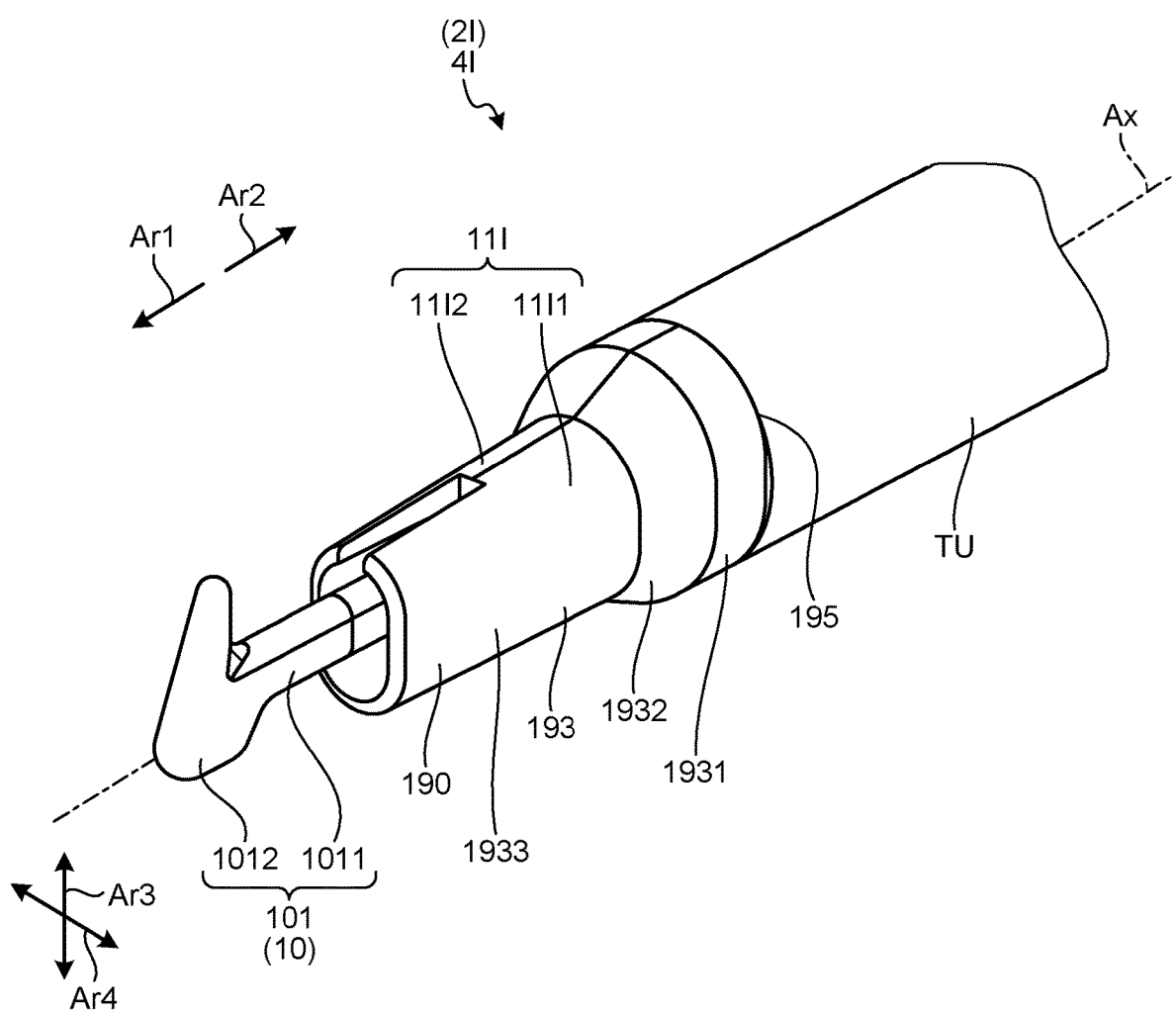
FIG. 41 is a diagram illustrating the distal end portion of the treatment-instrument main unit according to the exemplary embodiment.
Figure 42:
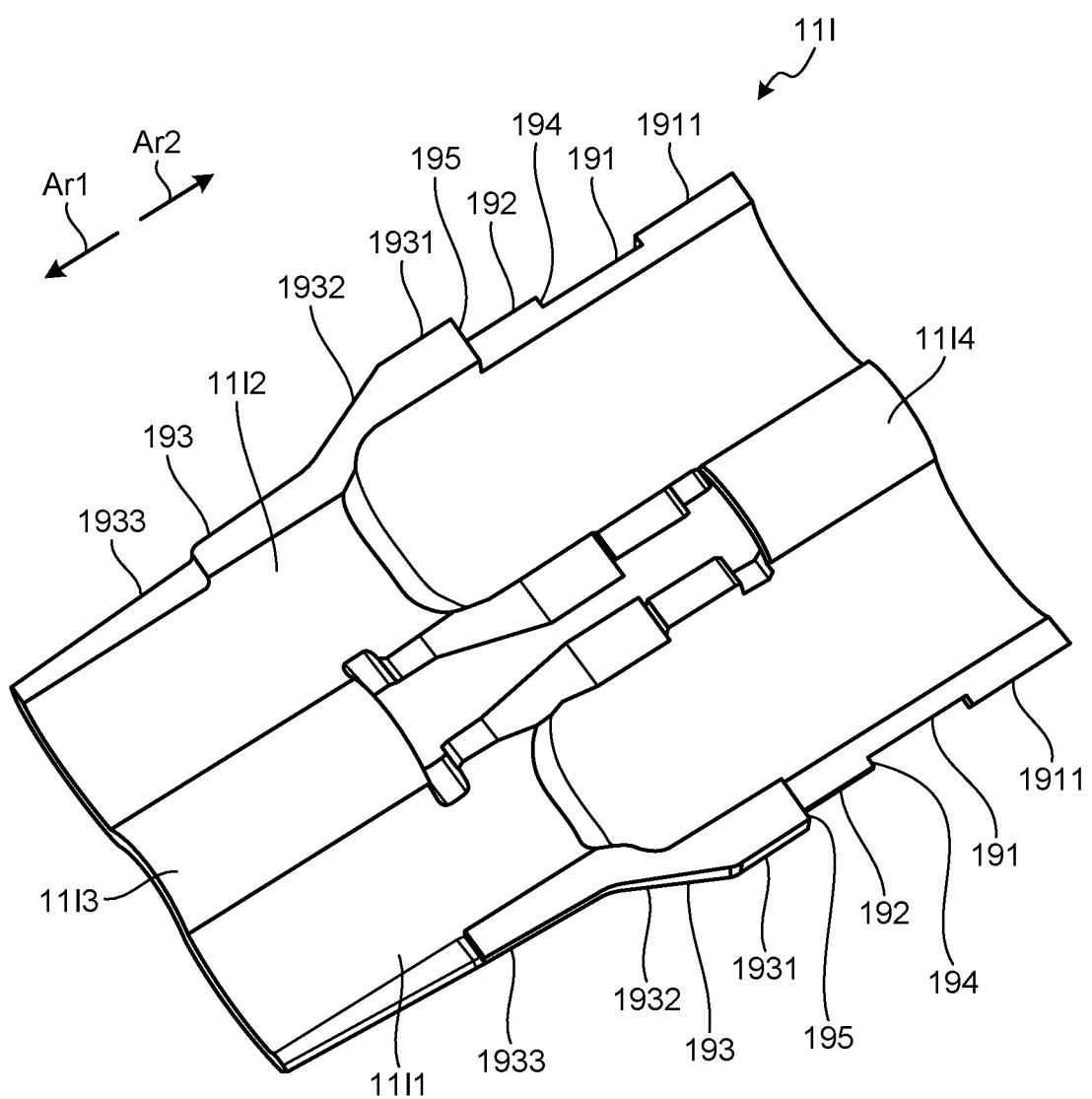
FIG. 42 is a diagram illustrating a cap.
Figure 43:
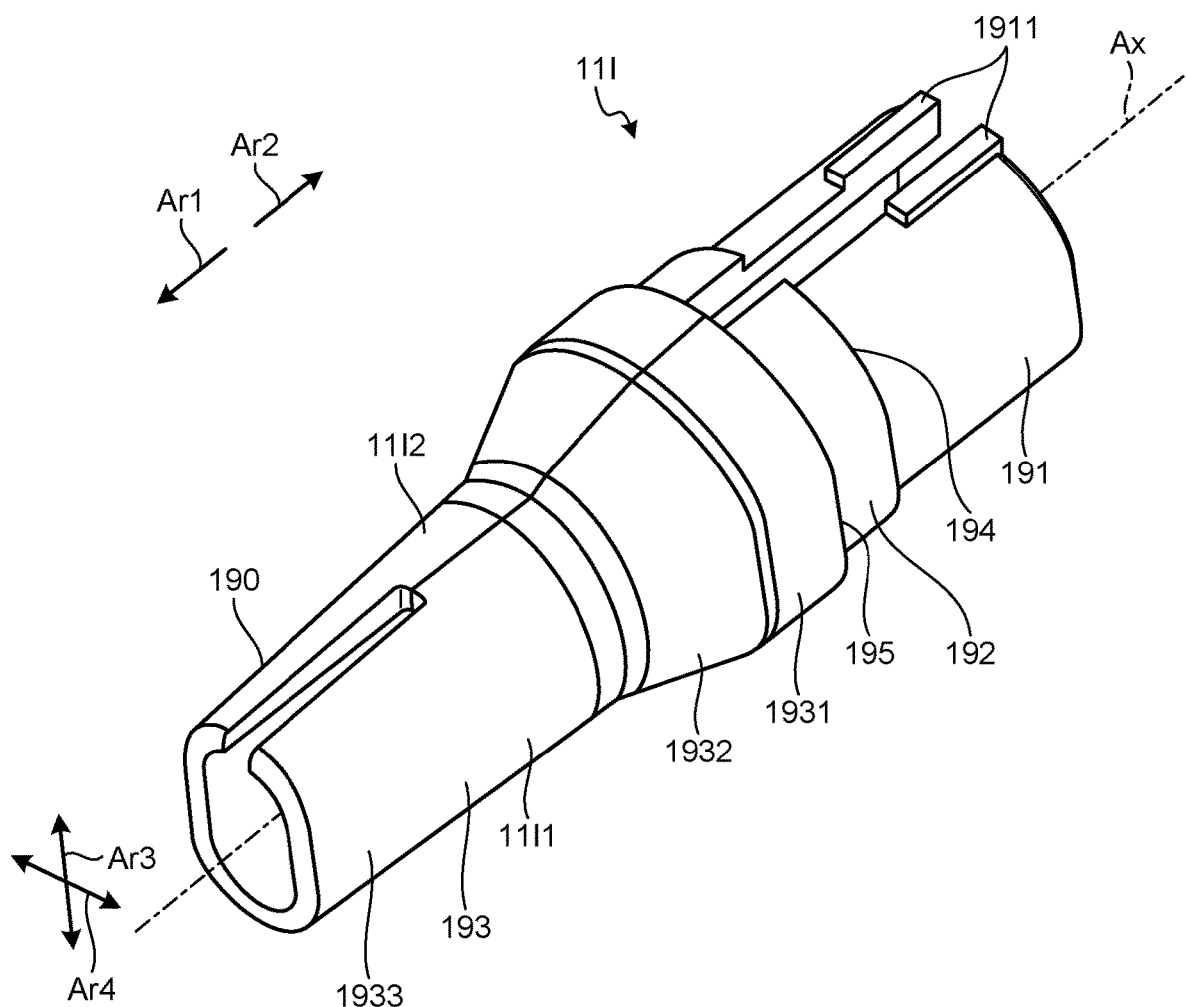
FIG. 43 is a diagram illustrating the cap

FIG. 40 to FIG. 41 are diagrams illustrating a distal end portion of the treatment-instrument main unit 4I according to the present embodiment. FIG. 42 and FIG. 43 are diagrams illustrating the cap 11I1. Specifically, FIG. 40 and FIG. 41 are diagrams illustrating an external view of the distal end portion of the treatment-instrument main unit 4I. While FIG. 40 illustrates a state in which the tube TU is removed, FIG. 41 illustrates a state in which the tube TU is attached. FIG. 42 is a diagram illustrating the cap 11I before a pair of living hinges 11I3, 11I4 are bent. FIG. 43 is a diagram illustrating the cap 11I after the pair of the living hinges 11I3, 11I4 are bent.

The cap 11I is made from a resin material, such as PEEK, having electric insulation. This cap 11I includes a first and a second caps 11I1, 11I2 that are joined by the pair of living hinges 11I3, 11I4 as illustrated in FIG. 42. These first and the second caps 11I1, 11I2 have shapes symmetric about the plane including the point of the hook portion 1012 and the center axis Ax as a boundary. In a state in which the first and the second caps 11I1 and 11I2 are assembled, the cap 11I includes an engaging portion 191 (FIG. 40, FIG. 42, FIG. 43), a connecting portion 192 (FIG. 40, FIG. 42, FIG. 43), and an exposed portion 193 as illustrated in FIG. 40 to FIG. 43.

The engaging portion 191 has a substantially cylindrical shape coaxial with the center axis Ax. In the present embodiment, an outer diameter dimension of the engaging portion 191 is a little smaller than an inner diameter dimension of the sheath 8I. On an outer peripheral surface of the engaging portion 191, a pair of engagement protrusions 1911 are arranged as illustrated in FIG. 40 FIG. 42, or FIG. 43.

The pair of the engagement protrusions 1911 are arranged respectively in the first and the second caps 11I1 and 11I2. More specifically, the pair of the engagement protrusions 1911 respectively protrude in a direction away from the center axis Ax from the outer peripheral surface of the engaging portion 191, and linearly extend toward the distal end side Ar1 from a proximal end of the engaging portion 191 while opposing to each other.

The connecting portion 192 is a portion connecting an end portion in the engaging portion 191 on the distal end side Ar1 and an end portion in the exposed portion 193 on the proximal end side Ar2, and has a substantially cylindrical shape surrounding the center axis Ax. In the connecting portion 192, an outer diameter dimension is larger than the engaging portion 191. That is, on an outer peripheral surface of the cap 11I, a first step portion 194 (FIG. 40, FIG. 42, FIG. 43) is arranged between the connecting portion 192 and the engaging portion 191.

The exposed portion 193 has a substantially cylindrical shape surrounding the center axis and is arranged at an end portion of the connecting portion 192 on the distal end side Ar1. In this exposed portion 193, an end portion on the proximal end side Ar2 connected to the connecting portion 192 has a larger outer diameter dimension than the connecting portion 192. That is, on the outer peripheral surface of the cap 11I, a second step portion 195 (FIG. 40 to FIG. 43) is arranged between the exposed portion 193 and the connecting portion 192. Hereinafter, for convenience of explanation, a surface abutting on the second step portion 195 on the outer peripheral surface of the exposed portion 193 will be denoted as protruded surface 1931.

Moreover, the outer peripheral surface of the exposed portion 193 is formed, as illustrated in FIG. 40 to FIG. 43, by the protruded surface 1931, a slant surface 1932, and a distal-end outer-peripheral surface 1933 arranged continuously from the proximal end side Ar2 toward the distal end side Ar1.

The protruded surface 1931 is a surface that linearly extends toward the distal end side Ar1 along the center axis Ax from a position abutting on the second step portion 195.

The slant surface 1932 is a surface in which a diameter dimension decreases toward the distal end side Ar1 from a position abutting on the protruded surface 1931.

The distal-end outer-peripheral surface 1933 is a surface that substantially linearly extends toward the distal end side Ar1 along the center axis Ax from a position abutting on the slant surface 1932.

An outer diameter dimension of a distal end portion 190 (FIG. 40, FIG. 41, FIG. 43) having the distal-end outer-peripheral surface 1933 is smaller than an outer diameter dimension n the engaging portion 191 corresponding to a proximal end portion. Moreover, the outer diameter dimension in the distal end portion 190 is smaller than an outer dimension of the hook portion 1012 in the first direction Ar3. The distal end portion 190 is made thin, and thereby acquires a function of providing a field of view for an operator that uses the treatment-instrument main unit 4I, or the like.

In an end portion of the sheath 8I on the distal end side Ar1, as illustrated in FIG. 40, a pair of engagement notch portions 871 linearly cut along the center axis Ax from the distal end toward the proximal end side Ar2, and with which the pair of the engagement protrusions 1911 are engaged are arranged. This engagement notch portion 871 includes a narrow portion 8711 that is positioned on the distal end side Ar1, and a wide portion 8712 that is positioned on the proximal end side Ar2, and that has a larger width than the narrow portion 8711.

In a manufacturing method of the treatment instrument 21 according to the present embodiment, step S3 is different from the manufacturing method (FIG. 8) of the treatment instrument 2 explained in the embodiment described above.

At step S3 according to the present embodiment, an operator bends a pair of living hinges 11E3, 11E4, to assemble the first and the second caps 11I1 and 11I2 in a state in which the pillar portion 1011 is positioned inside the cap 11I (upper side in FIG. 42). In this state, the hook portion 1012 protrudes out from the distal end side Ar1 of the cap 11I in which the first and the second caps 11I1, 11I2 are assembled. The operator moves the cap 11I to the proximal end side Ar2, and inserts the engaging portion 191 into the inside of the sheath 8I while putting the pair of the engagement protrusions 1911 in the engagement notch portions 871. The cap 11I is attached to the sheath 8I as the pair of the engagement protrusions 1911 are engaged with the wide portions 8712 in the engagement notch portions 871.

At step S4, in a state in which the tube TU is attached, the distal end of the tube TU is positioned on the outer peripheral surface of the connecting portion 192, In the present embodiment, a diameter dimension at the protruded surface 1931 is substantially the same as an outer diameter dimension of the tube TU at the distal end. Moreover, the diameter dimension at the protruded surface 1931 may be equal to or smaller than the outer diameter dimension of the tube TU at the distal end, or may be equal to or larger than the outer diameter dimension of the tube TU at the distal end.

As described above, the tube TU is arranged at a position enabling to cover both the outer peripheral surface of the sheath 8I and the outer peripheral surface of the cap 11I, straddling a boundary between the sheath 8I and the cap 11I. Moreover, in the sheath 8I and the cap 11I, a portion corresponding to the engaging portion 191 is an overlap area that overlaps in a radial direction. The tube TU covers the overlap area.

Also when the treatment-instrument main unit 4I according to the present embodiment explained above is adopted, effects similar to those of the embodiments described above with respect to FIGS. 1-29 are obtained.

Next, another exemplary embodiment will be explained.

In the following explanation, identical reference symbols are assigned to components identical to those of the embodiments described above, and detailed explanation thereof will be omitted or simplified.

The present embodiment differs from the embodiment described above in a structure of the distal end portion of the treatment-instrument main unit 4 (structure of the vibration transmission member 10 and the cap 11).

Hereinafter, for convenience of explanation, the treatment instrument 2 according to the present embodiment will be denoted as treatment instrument 2J. Moreover, the treatment-instrument main unit 4 according to the present embodiment will be denoted as treatment-instrument main unit 4J. Furthermore, the vibration transmission member 10 according to the present embodiment will be denoted as vibration transmission member 10J. Moreover, the cap 11 according to the present embodiment will be denoted as cap 11J.

The sheath 8 and tie cap 11J correspond to a cover member. Moreover, the cap 11J corresponds to a tubular portion.

Figure 44:
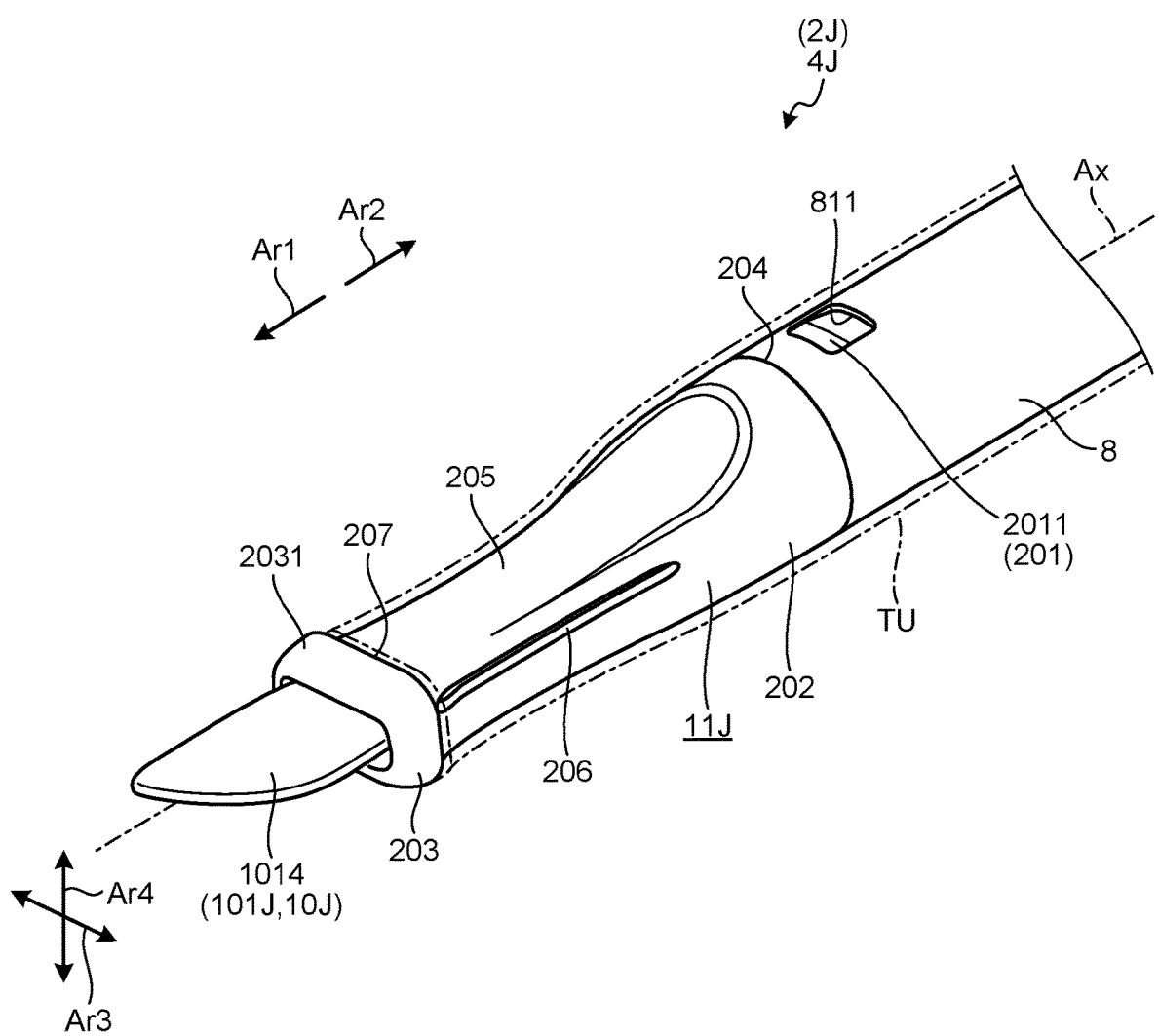
FIG. 44 is a diagram illustrating a distal end portion of a treatment-instrument main unit according to an exemplary embodiment.
Figure 45:
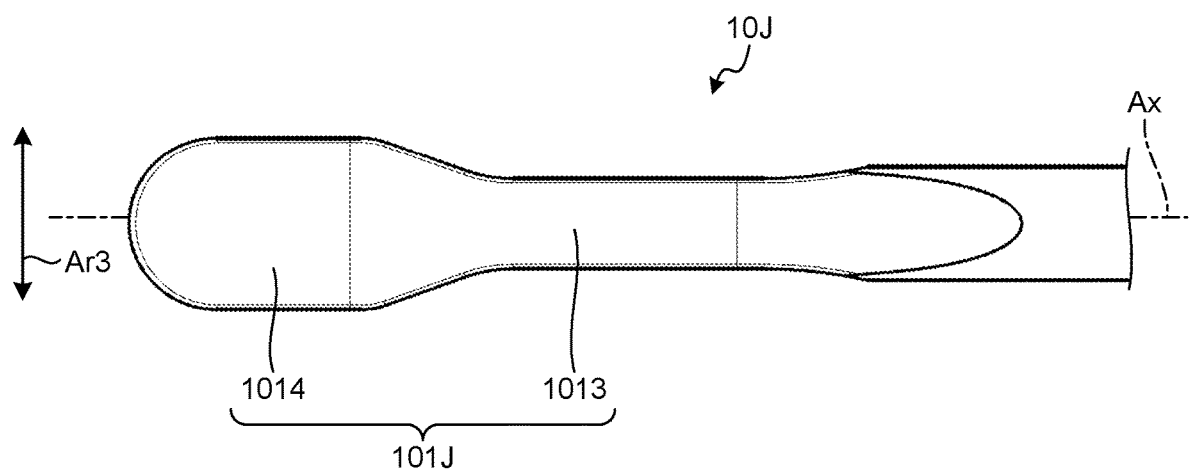
FIG. 45 is a diagram illustrating a distal end portion of a vibration transmission member.
Figure 46:
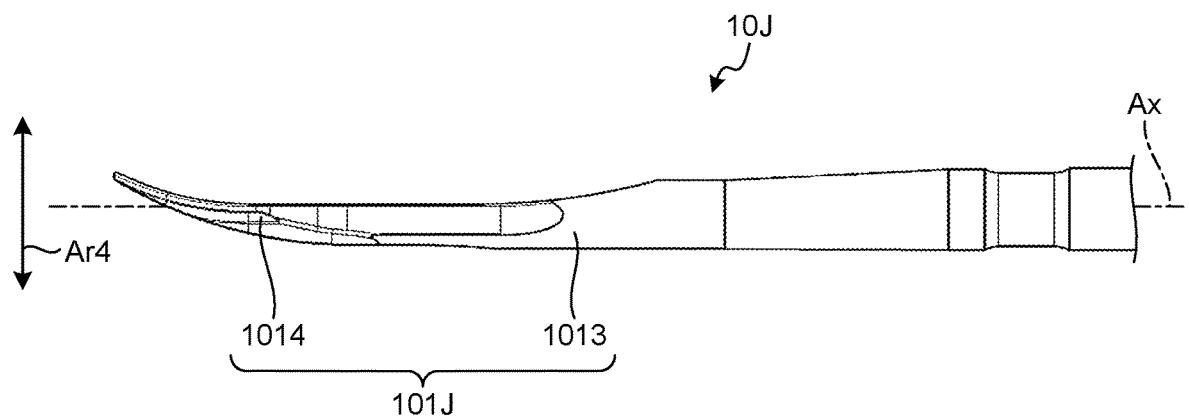
FIG. 46 is a diagram illustrating the distal end portion of the vibration transmission member.

FIG. 44 is a diagram illustrating a distal end portion of the treatment-instrument main unit 4J according to the present embodiment. FIG. 44, for convenience of explanation, the tube TU is illustrated with an alternate long and short dash line. FIG. 45 and FIG. 46 are diagrams illustrating a distal end portion of the vibration transmission member 10J. Specifically, FIG. 45 illustrates the vibration transmission member 10J viewed along the second direction Ar4. FIG. 46 illustrates the vibration transmission member 10J along the first direction Ar3.

The vibration transmission member 10J differs from the vibration transmission member 10 explained in the embodiment described above in a shape of the end effector 101. Hereinafter, for convenience of explanation, the end effector according to the present embodiment will be denoted as end effector 101J.

The end effector 101J includes, as illustrated in FIG. 44 to FIG. 46, a pillar portion 1013 that extends along the center axis Ax and a spatula portion 1014 that is arranged at an end portion of the pillar portion 1013 on the distal end side Ar1.

The spatula portion 1014 has a larger width dimension than a width dimension (outer dimension in the first direction Ar3) of the pillar portion 1013, and is curved along the second direction Ar4 as it approaches the distal end Ar1.

The cap 11J is made from a resin material, such as PEEK, PTFE, and PEA, having electric insulation. This cap 11J includes, as illustrated in FIG. 44, an engaging portion 201, a connecting portion 202, and a distal end portion 203.

The engaging portion 201 has a shape similar to the engaging portion 111 explained in the embodiment described above. That is, the engaging portion 201 includes a pair of claw portions 2011 (FIG. 44) similar to the pair of the claw portions 1112 explained in the embodiment described above. In the present embodiment, an inner diameter dimension of the engaging portion 201 is a little larger than a width dimension of the spatula portion 1014.

The connecting portion 202 is a portion connecting an end portion of the engaging portion 201 on the distal end side Ar1 and an end portion of the distal end portion 203 on the proximal end side Ar2, and has a substantially cylindrical shape surrounding the center axis Ax in the connecting portion. 202, the end portion on the proximal end side Ar2 connected to the engaging portion 201 has an outer diameter larger than the enraging portion 201. That is, on an outer peripheral surface of the cap 11J, a first step portion 204 (FIG. 44) is arranged between the connecting portion 202 and the engaging portion 201.

In this connecting portion 202, a substantially center portion in the direction toward the center axis Ax is smaller in outer dimension (thickness dimension) in the second direction Ar4 than other portions. The thickness dimension of the connecting portion 202 gradually increases from the substantially center portion toward the distal end side Ar1 and the proximal end side Ar2, Moreover, in the connecting portion 202, the substantially center portion has an outer dimension in the first direction Ar3 (width dimension) smaller than other portions. The width dimension of the connecting portion 202 gradually increases from the substantially the center portion toward the distal end side Ar1 and the proximal end side Ar2.

Hereinafter, the substantially center portion, the outer dimensions in the first and the second directions Ar3, Ar4 of which are smallest in the connecting portion 202 will be denoted as intermediate portion 205 (FIG. 44).

The outer dimension in the first direction Ar1 in the intermediate portion 205 is smaller than the outer dimension in the first direction Ar3 in other portions in the cap 11J, and is smaller than the width dimension of the spatula portion 1014. The intermediate portion 205 is made thin, and thereby acquires a function of providing a field of view for an operator that uses the treatment-instrument main unit 4J, or the like.

In the present embodiment, an inner dimension of the intermediate portion 205 is as follows.

Namely, the inner dimension in the first direction Ar3 in the intermediate portion 205 is smaller than the width dimension of the spatula portion 1014. Moreover, the inner dimension in the second direction Ar4 in the intermediate portion 205 is larger than the thickness dimension (outer dimension in the second direction Ar4) of the spatula portion 1014.

On the other hand, in the connecting portion 202, portions other than the intermediate portion 205 has an inner dimension enabling insertion of the spatula portion 1014.

In the connecting portion 202 explained above, a slit 206 (FIG. 44) that is arranged over the intermediate portion 205, and that linearly extends along the center axis Ax is arranged on both end sides in the first direction Ar3. This slit 206 corresponds to the first slit.

A width dimension of this slit 206 is a little larger than the thickness dimension of the spatula portion 1014.

The distal end portion 203 has a cylindrical shape surrounding the center axis Ax, and is arranged at an end portion of the connecting portion 202 on the distal end side Ar1. This distal end portion 203 has respective outer diameter dimensions in the first and the second directions Ar3, Ar4 larger than the distal end portion of the connecting portion 202 on the distal end side Ar1. That is, on the outer peripheral surface of the cap 11J, a second step portion 207 (FIG. 44) is arranged between the distal end portion 203 and the connecting portion 202. Hereinafter, for convenience of explanation, an outer peripheral surface of the distal end portion 203 will be denoted as protruded surface 2031.

In the present embodiment, the distal end portion 203 has an inner dimension enabling insertion of the spatula portion 1014.

The outer dimension of the distal end portion. 203 in the second direction Ar4 is smaller than an outer dimension of the engaging portion 201 corresponding to a proximal end portion. The distal end portion 203 is made thin together with the intermediate portion 205, and thereby acquires a function of providing a field of view for an operator that uses the treatment-instrument main unit 4J.

In a manufacturing method of the treatment instrument 2J according to the present embodiment, step S3 is different from the manufacturing method (FIG. 8) of the treatment instrument 2 explained in the embodiment described above.

At step S3 according to the present embodiment, an operator inserts the end effector 101J into the inside of the cap 11J from the proximal end side Ar2 of the cap 11. The operator moves the cap 11J to the proximal end side Ar2 while putting an end portion of the spatula portion 1014 on the first direction Ar2 in the slit 206, to make the spatula portion 1014 protrude out from the distal end side Ar1 of the cap 11J. Moreover, the operator moves the cap 11J to the proximal end side Ar2, to insert the engaging portion 201 into the inside of the sheath 8. The cap 11J is attached to the sheath 6 as the claw portion 2011 engages with the engagement opening portion 811. That is, the cap 11J is attached to the sheath 8 by a snap-fit mechanism.

At step S4, in a state in which the tube TU is attached, the distal end of the tube TU is positioned on the outer peripheral surface of the connecting portion 202. In the present embodiment, respective diameter dimensions of the protruded surface 2031 in the first and the second directions Ar3, Ar4 are substantially the same as respective outer diameter dimensions of the tube TU at the distal end in the first and the second directions Ar3, Ar4. Moreover, the respective diameter dimensions of the protruded surface 2031 in the first and the second directions Ar3, Ar4 may be equal to or smaller than the respective outer diameter dimensions of the tube TU in the first and the second directions Ar3, Ar4 at the distal end, or may be equal to or larger than the respective outer diameter dimensions of the tube TU in the first and the second directions Ar3, Ar4 at distal end.

As described above, the tube TU is arranged at a position enabling to cover both the outer peripheral surface of the sheath 8 and the outer peripheral surface of the cap 11J, straddling a boundary between the sheath 8 and the cap 11J. Moreover, in the sheath 8 and the cap 11J, a portion corresponding to the engaging portion 201 is an overlap area that overlaps in a radial direction. The tube TU covers the overlap area.

Also when the treatment-instrument main unit 4J according to the embodiment explained above is adopted, effects similar to those of the embodiment described above with respect to FIGS. 1-16 are obtained.

Next, another exemplary embodiment will be explained.

In the following explanation, identical reference symbols are assigned to components identical to those of the embodiments described above, and detailed explanation thereof will be omitted or simplified.

The present embodiment differs from the embodiment described above with respect to FIGS. 1-16 in a structure of the distal end portion of the treatment-instrument main unit 4 (structure of the vibration transmission member 10 and the cap 11).

Hereinafter, for convenience of explanation, the treatment instrument 2 according to the present embodiment will be denoted as treatment instrument 2K. Moreover, the treatment-instrument main unit 4 according to the present embodiment will be denoted as treatment-instrument main unit 4K. Furthermore, the cap 11 according to the present embodiment will be denoted as cap 11K. Because the vibration transmission member 10 according to present embodiment has a shape similar to that of the vibration transmission member 10J explained in the embodiment described above with respect to FIGS. 44-46, it will be denoted as vibration transmission member 10J.

The sheath 8 and the cap 11K correspond to a cover member. Moreover, the cap 11K corresponds to a tubular portion.

Figure 47:
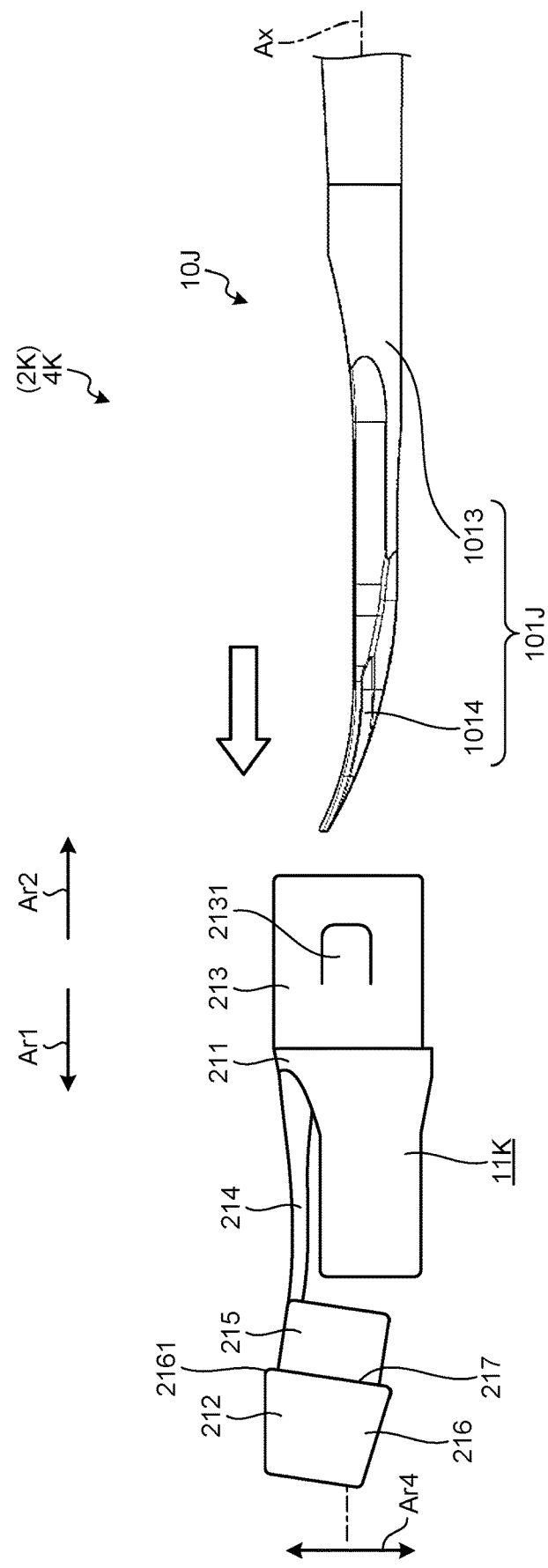
FIG. 47 is a diagram illustrating a distal end portion of a treatment-instrument main unit according to an exemplary embodiment.
Figure 48:
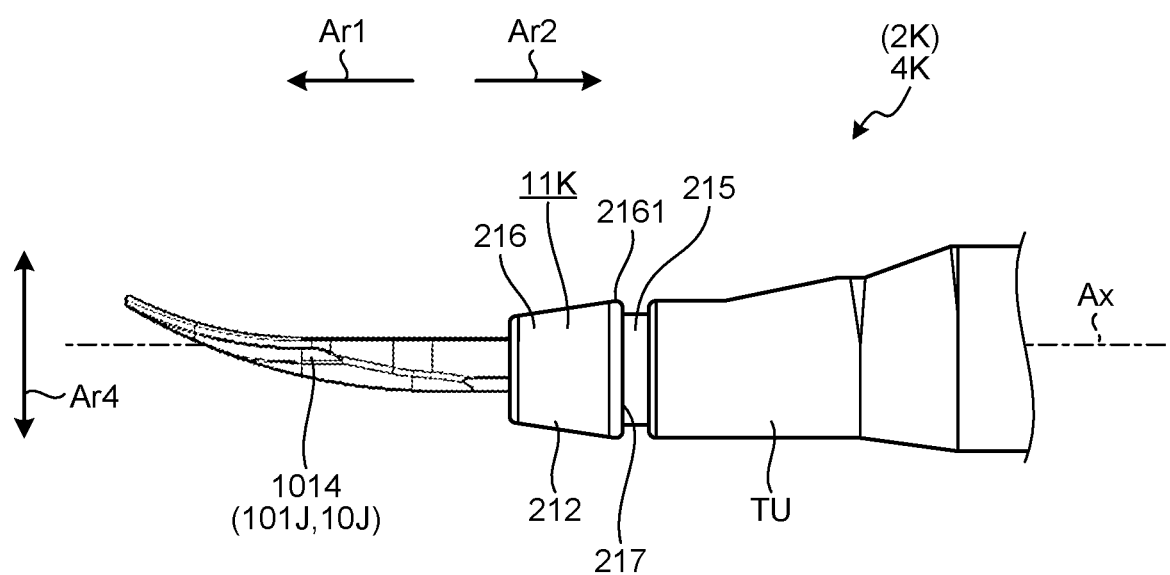
FIG. 48 is a diagram illustrating the distal end portion of the treatment-instrument main unit according to the exemplary embodiment.

FIG. 47 and FIG. 48 are diagrams illustrating a distal end portion of the treatment-instrument main unit 4K according to the present embodiment. Specifically, FIG. 47 is a diagram illustrating a state in which the spatula portion 1014 is inserted into inside of the cap 11K. FIG. 48 is a diagram illustrating an external view of the treatment-instrument main unit 4K.

The cap 11K is made from a resin material, such as PTFE or PFA, having electric insulation. This cap 11K includes, as illustrated in FIG. 47 or FIG. 48, a first member 211 and a second member 212.

The first member 211 is arranged on the proximal end side Ar2 relative to the second member 212. This first member 211 includes an engaging portion 213 having a shape similar to the engaging portion 201 explained in the embodiment described above with respect to FIGS. 44-46. That is, the engaging portion 213 includes a pair of claw portions 2131 similar to the pair of the claw portions 2011 explained in the embodiment described above.

The second member 212 is joined to the first member 211 swingably along the second direction Ar4 by a joint portion 214 (FIG. 47) that extends toward the distal end side Ar1 from an end portion of the engaging portion 213 on the distal end side Ar1. This second member 212 includes a connecting portion 215 and a distal end portion 216 as illustrated in FIG. 47.

The connecting portion 215 has a cylindrical shape coaxial with the center axis and is connected to an end portion of the joint portion 214 on the distal end side Ar1. In the present embodiment, an inner diameter dimension of the connecting portion 215 is smaller than the width dimension of the spatula portion 1014.

The distal end portion 216 has a substantially cylindrical shape coaxial with the center axis Ax, and is arranged at an end portion of the connecting portion 215 on the distal end side Ar1. This distal end portion 216 has a larger outer diameter dimension than the connecting portion 215. That is, on an outer peripheral surface of the second member 212, a step portion 217 (FIG. 47, FIG. 48) is arranged between the distal end portion 216 and the connecting portion. 215, Hereinafter, for convenience of explanation, an outer peripheral surface of the distal end portion 216 will be denoted as protruded surface 2161.

In the present embodiment, an inner diameter dimension of the distal end portion 216 is smaller than the width dimension of the spatula portion 1014.

An outer diameter dimension of the distal end portion 216 is smaller than an outer diameter dimension of the engaging portion 213 corresponding to the proximal end portion. An outer dimension of the distal end portion 216 in the first direction Ar3 is smaller than the width dimension of the spatula portion 1014. The distal end portion 216 is made thin, and thereby acquires a function of providing a field of view for an operator that uses the treatment-instrument main unit 4K, or the lik.

In a manufacturing method of e treatment instrument 2K according to the present embodiment, step S3 is different from the manufacturing method (FIG. 8) of the treatment instrument 2 explained in the embodiment described above.

At step S3 according to the present embodiment, an operator inserts the end effector 101J into the inside of the engaging portion 213 from the proximal end side Art of the engaging portion 213 as illustrated in FIG. 47. Moreover, because the cap 11K is made from a relatively flexible material, such as PTFE or PFA, the operator inserts the end effector 101J into the inside of the connecting portion 215 from the proximal end side of the connecting portion 215 while deforming the cap 11K. Thus, the spatula portion 1014 protrudes from the distal end side Ar1 of the distal end portion 216. As the end effector 101J is inserted thereinside, the second member 212 moves until a center axis of the second member 212 coincides with the center axis Ax from an upper side to a lower side in FIG. 47, following a curved shape of the spatula portion 1014. The cap 11K is attached to the sheath 8 as the claw portion 2131 engages with the engagement opening portion 811. That is, the cap 11K is attached to the sheath 8 by a snap-fit mechanism.

At step S4, in a state in which the tube TU is attached, the distal end of the tube TU is positioned on an outer-peripheral surface of the connecting portion 215 as illustrated in FIG. 48. In the present embodiment, a diameter dimension at the protruded surface 2161 is substantially the same as an outer diameter dimension of the tube TU at the distal end. Moreover, the diameter dimension at the protruded surface 2161 may be equal to or smaller than the outer diameter dimension of the tube TU at the distal end, or may be equal to or larger than the outer diameter dimension of the tube TU at the distal end.

As described above, the tube TU is arranged at a position enabling to cover both the outer peripheral surface of the sheath 8 and the outer peripheral surface of the cap 11K, straddling a boundary between the sheath 8 and the cap 11K. Moreover, in the sheath 8 and the cap 11K, a portion corresponding to the engaging portion 213 is an overlap area that overlaps in a radial direction. The tube TU covers the overlap area.

Also when the treatment-instrument main unit 4K according to the present embodiment explained above is adopted, effects similar to those of the embodiment described above are obtained.

Embodiments to implement the disclosure have so far been explained, but the disclosure is not to be limited only to the embodiments described above.

In the embodiments described above, a treatment instrument according to the disclosure is configured to apply both an ultrasonic energy and a hi frequency energy to a target site, but it is not limited thereto, and may be configured to apply at least either energy out of an ultrasonic energy, a high frequency energy, and a thermal energy. "Applying a thermal energy to a target site" means that propagating heat generated by a heater or the like to a target site.

In the embodiments described above, the caps 11, 11A, 11B, and 11D to 11K are adopted as a tubular portion, but not limited thereto, a sheath may be adopted. That is, without using the caps 11, 11A, 11B, and 11D to 11K, a distal end portion of a sheath may be formed in a shape similar to the caps 11, 11A, 11B, and 11D to 11K.

In the embodiments described above, step S2 and step S3 may be performed in the inverse order.

In the embodiment described above with respect to FIGS. 1-16, the cap 11 is structured without arranging the first and the second slits 116, 117, and the cap 11 is constituted of an elastic member. At step S3, the end effector 101 is inserted into the inside of the cap 11 while deforming the cap 11, and makes the end effector 101 protrude out from the distal end side Ar1 of the cap 11.

According to the cover member and the treatment instrument according to the disclosure, a field of view can be acquired.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

It should be noted that the present technology can have the following configurations.

(Appendix 1)

A treatment instrument including:

a tubular sheath that extends from a distal end to a proximal end to determine a longitudinal axis direction;

a tubular cap that is attached to a distal end of the sheath;

an end effector that protrudes from a distal end of the cap, the end effector being configured to perform treatment on a living tissue; and a tube that is arranged at a position at which the tube covers both of an outer peripheral surface of the sheath and an outer peripheral surface of the cap across a boundary between the sheath and the cap, the tube being configured to contract in a radial direction perpendicular to the longitudinal axis direction.

(Appendix 2)

The treatment tool according to Appendix 1, in which the sheath and the cap include overlap regions where the sheath and the cap overlap with each other in the radial direction, and the tube is configured to cover the overlap regions.

(Appendix 3)

The treatment instrument according to Appendix 2, in which the outer peripheral surface of the cap includes a reduced diameter portion whose dimension in the radial direction decreases toward a distal end of the cap in the overlap region, and the tube covers the reduced diameter portion.

(Appendix 4)

The treatment instrument according to Appendix 3, in which the outer peripheral surface of the cap includes a protruded portion that is arranged between the distal end of the cap and the reduced diameter portion, the protruded portion jutting out outward in the radial direction, and the distal end of the cap is located between the protruded portion and the reduced diameter portion.

(Appendix 5)
The treatment instrument according to Appendix 4, in which
a dimension of the protruded portion in the radial direction is equal to or less than a dimension of an outer peripheral surface of a distal end of the tube in the radial direction.

(Appendix 6)
The treatment instrument according to Appendix 4, in which
a dimension of the protruded portion in the radial direction is equal to or larger than a dimension of an outer peripheral surface of a distal end of the tube in the radial direction.

(Appendix 7)
The treatment instrument according to Appendix 2, in which
the cap is detachably attached to the sheath.

(Appendix 8)
The treatment instrument according to Appendix 1, in which
the cap is made of an electrically insulating resin material.

(Appendix 9)
The treatment instrument according to Appendix 4, in which
the outer peripheral surface of the cap has a dimension in the radial direction that decreases from the protruded portion toward the distal end of the cap.

(Appendix 10)
The treatment instrument according to Appendix 1, in which
the cap includes a slit for preventing interference with the end effector.

(Appendix 11)
The treatment instrument according to Appendix 1, further including:
a vibration transmission member inserted into the sheath and the cap and transmitting ultrasonic vibration along the longitudinal axis direction, the end effector being arranged at a distal end of the vibration transmission member.

(Appendix 12)
A tubular cap used for a treatment instrument including an end effector configured to treat a living tissue, the cap including:
an engaging portion configured to engage with a distal end of a tubular sheath extending from a distal end toward a proximal end to define a longitudinal axis direction,
an outer peripheral surface of the cap including a reduced diameter portion whose dimension in a radial direction perpendicular to the longitudinal axis direction decreases from the engaging portion toward a distal end of the cap,
an outer surface of the engaging portion and the reduced diameter portion being arranged at positions straddling a boundary between the sheath and the cap and being covered together with an outer peripheral surface of the sheath by a tube configured to contract in the radial direction.

(Appendix 13)
The cap according to Appendix 12, in which the engaging portion is a region that overlaps the sheath in the radial direction.

(Appendix 14)
The cap according to Appendix 13, in which the outer peripheral surface of the cap includes a protruded portion that is arranged between the distal end of the cap and the reduced diameter portion, the protruded portion jutting out outward in the radial direction, and
the distal end of the cap is located between the protruded portion and the reduced diameter portion.

(Appendix 15)
The cap according to Appendix 14, in which
a dimension of the protruded portion in the radial direction is equal to or less than a dimension of an outer peripheral surface of a distal end of the tube in the radial direction.

(Appendix 16)
The cap according to Appendix 14, in which a dimension of the protruded portion in the radial direction is equal to or larger than a dimension of an outer peripheral surface of a distal end of the tube in the radial direction.

(Appendix 17)
The cap according to Appendix 12, in which
the cap is made of an electrically insulating resin material.

(Appendix 18)
The cap according to Appendix 14, in which
the outer peripheral surface of the cap has a dimension in the radial direction that decreases from the protruded portion toward the distal end of the cap.

(Appendix 19)
The cap according to Appendix 12, further including
a slit for preventing interference with the end effector.

(Appendix 20)
A method of manufacturing a treatment instrument, the method including:
inserting a shaft into a tubular sheath that extends from a distal end to a proximal end to determine a longitudinal axis direction, the shaft being provided with an end effector at a distal end of the shaft, the end effector being configured to treat a living tissue;
attaching the tubular cap to a distal end of the sheath;
arranging a tube at a position at which the tube covers both of an outer peripheral surface of the sheath and an outer peripheral surface of the cap across a boundary between the sheath and the cap; and
contracting the tube in a radial direction perpendicular to the longitudinal axis direction.

What is claimed is:
1. A cover member that extends in a longitudinal axis direction from a distal end toward a proximal end, a shaft being inserted into the cover member, the shaft including an end effector at a distal end of the shaft, the end effector being configured to treat a living tissue, the cover member comprising:
a sheath that is formed in a cylindrical shape, the shaft being inserted in the sheath; and
a tubular portion that is attached to a distal end of the sheath,
wherein:
a direction perpendicular to the longitudinal axis direction is a first direction, and a direction perpendicular to both of the longitudinal axis direction and the first direction is a second direction,
one or both of (i) and (ii) is satisfied:
(i) the tubular portion is formed such that an outer dimension of a distal end portion of the tubular portion in the first direction is smaller than an outer dimension of a proximal end portion of the tubular portion in the first direction, and
(ii) an outer dimension of the distal end portion in the second direction is smaller than an outer dimension of the proximal end portion in the second direction, and the tubular portion includes:
- a protruded portion that is arranged between the distal end portion and the proximal end portion, the protruded portion jutting out outward in a radial direction perpendicular to the longitudinal axis direction, and
- a first slit cut out from a distal end of the distal end portion to a distal end of the protruded portion.

2. The cover member according to claim 1, wherein
an outer dimension of the end effector in the first direction is larger than an outer dimension of the end effector in the second direction, and
the first slit extends in the longitudinal axis direction at one or both end sides of the tubular portion in the first direction.

3. The cover member according to claim 2, wherein
the outer dimension of the distal end portion in the first direction is smaller than the outer dimension of the end effector in the first direction.

4. The cover member according to claim 1, wherein
the tubular portion includes a second slit capable of receiving the end effector for insertion into an inside of the tubular portion, and
the second slit is arranged on an identical side to the first slit in the first direction, extends in the longitudinal axis direction, and is cut out from a proximal end of the proximal end portion toward a distal end side of the tubular portion.

5. The cover member according to claim 2, wherein
the tubular portion includes a connecting portion configured to connect the distal end portion and the proximal end portion,
the connecting portion includes an intermediate portion, and
an outer dimension of the intermediate portion in the first direction is smaller than: (i) the outer dimension of the end effector in the first direction, (ii) the outer dimension of the distal end portion in the first direction, and (iii) the outer dimension of the proximal end portion in the first direction.

6. The cover member according to claim 5, wherein
the first slit is arranged in the connecting portion, on both end sides of the intermediate portion in the first direction.

7. The cover member according to claim 1, wherein
the tubular portion is constituted of a first member and a second member that are joined to each other.

8. The cover member according to claim 1, wherein
the tubular portion is constituted of an elastic member.

9. The cover member according to claim 1, wherein the first slit is configured to receive the end effector to avoid interference with the end effector when the end effector is inserted in the tubular portion.

10. A treatment instrument comprising:
a shaft including an end effector at a distal end of the shaft, the end effector being configured to treat a living tissue; and
a cover member including a tubular portion that extends along a longitudinal axis direction from a distal end portion toward a proximal end portion of the tubular portion,
wherein:
the shaft is inserted into an inside of the tubular portion in a state in which the end effector protrudes out from a distal end of the tubular portion,
a direction perpendicular to the longitudinal axis direction is a first direction, and a direction perpendicular to both of the longitudinal axis direction and the first direction is a second direction,
one or both of (i) and (ii) is satisfied:
- (i) the tubular portion is formed such that an outer dimension of the distal end portion in the first direction is smaller than an outer dimension of the proximal end portion in the first direction, and
- (ii) an outer dimension of the distal end portion in the second direction is smaller than an outer dimension of the proximal end portion in the second direction, and the tubular portion includes:
- a protruded portion that is arranged between the distal end portion and the proximal end portion, the protruded portion jutting out outward in a radial direction perpendicular to the longitudinal axis direction, and
- a first slit cut out from a distal end of the distal end portion to a distal end of the protruded portion.

11. The treatment instrument according to claim 10, wherein
an outer dimension of the end effector in the first direction is larger than an outer dimension of the end effector in the second direction, and
the first slit extends in the longitudinal axis direction at one or both end sides of the tubular portion in the first direction.

12. The treatment instrument according to claim 10, wherein
an outer dimension of the end effector in the first direction is larger than an outer dimension of the end effector in the second direction, and
the outer dimension of the distal end portion in the first direction is smaller than the outer dimension of the end effector in the first direction.

* * * * *